US009664677B2

(12) United States Patent
Strano et al.

(10) Patent No.: US 9,664,677 B2
(45) Date of Patent: May 30, 2017

(54) POLYMER-NANOSTRUCTURE COMPOSITION FOR SELECTIVE MOLECULAR RECOGNITION

(75) Inventors: Michael S. Strano, Lexington, MA (US); Jingqing Zhang, Cambridge, MA (US); Paul Walter Barone, Allston, MA (US); Daniel A. Heller, Rye Brook, NY (US); Jong-Ho Kim, Ansan (KR)

(73) Assignee: MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 782 days.

(21) Appl. No.: 13/090,199

(22) Filed: Apr. 19, 2011

(65) Prior Publication Data
US 2011/0257033 A1    Oct. 20, 2011

Related U.S. Application Data

(60) Provisional application No. 61/325,599, filed on Apr. 19, 2010.

(51) Int. Cl.
*G01N 33/542* (2006.01)
*B82Y 30/00* (2011.01)

(52) U.S. Cl.
CPC ............ *G01N 33/542* (2013.01); *B82Y 30/00* (2013.01)

(58) Field of Classification Search
None
See application file for complete search history.

(56) References Cited

U.S. PATENT DOCUMENTS

| | | | |
|---|---|---|---|
| 4,080,442 A * | 3/1978 | Mizutani | C07H 13/12 514/53 |
| 2002/0157120 A1 | 10/2002 | Tsien et al. | |
| 2003/0198573 A1 | 10/2003 | Forood et al. | |
| 2004/0254419 A1 | 12/2004 | Wang et al. | |
| 2005/0282244 A1* | 12/2005 | Fleming et al. | 435/34 |
| 2007/0020691 A1 | 1/2007 | Kanter et al. | |
| 2007/0191932 A1* | 8/2007 | Kutryk | A61F 2/82 623/1.38 |
| 2007/0231790 A1 | 10/2007 | Su | |
| 2007/0292896 A1* | 12/2007 | Strano | B82Y 15/00 435/7.9 |
| 2008/0009002 A1 | 1/2008 | Gruner et al. | |
| 2008/0193956 A1 | 8/2008 | Kricka et al. | |
| 2008/0242854 A1 | 10/2008 | Mizu et al. | |
| 2008/0257015 A1 | 10/2008 | Lukehart et al. | |
| 2009/0057650 A1 | 3/2009 | Lieber et al. | |
| 2009/0087493 A1* | 4/2009 | Dai et al. | 424/490 |
| 2009/0155170 A1* | 6/2009 | Reutelingsperger et al. | 424/1.69 |

(Continued)

OTHER PUBLICATIONS

Chacko (2003) Mol Immunol 39: 933-939.*

(Continued)

*Primary Examiner* — Mark Shibuya
*Assistant Examiner* — Richard Moerschell
(74) *Attorney, Agent, or Firm* — Steptoe & Johnson LLP

(57) ABSTRACT

A composition can include a complex, where the complex includes a photoluminescent nanostructure and a polymer free from selective binding to an analyte, the polymer adsorbed on the photoluminescent nanostructure, and a selective binding site associated with the complex.

6 Claims, 105 Drawing Sheets

(56) References Cited

U.S. PATENT DOCUMENTS

2010/0044230 A1  2/2010  Papadimitrakopoulos et al.

OTHER PUBLICATIONS

Galaev (1994) J Chrom, 684:45-54.*
International Preliminary Report on Patentability dated Nov. 1, 2012 for PCT/US2011/033116.
International Search Report and Written Opinion, PCT/US11/33116, mailed Jun. 1, 2011.

* cited by examiner

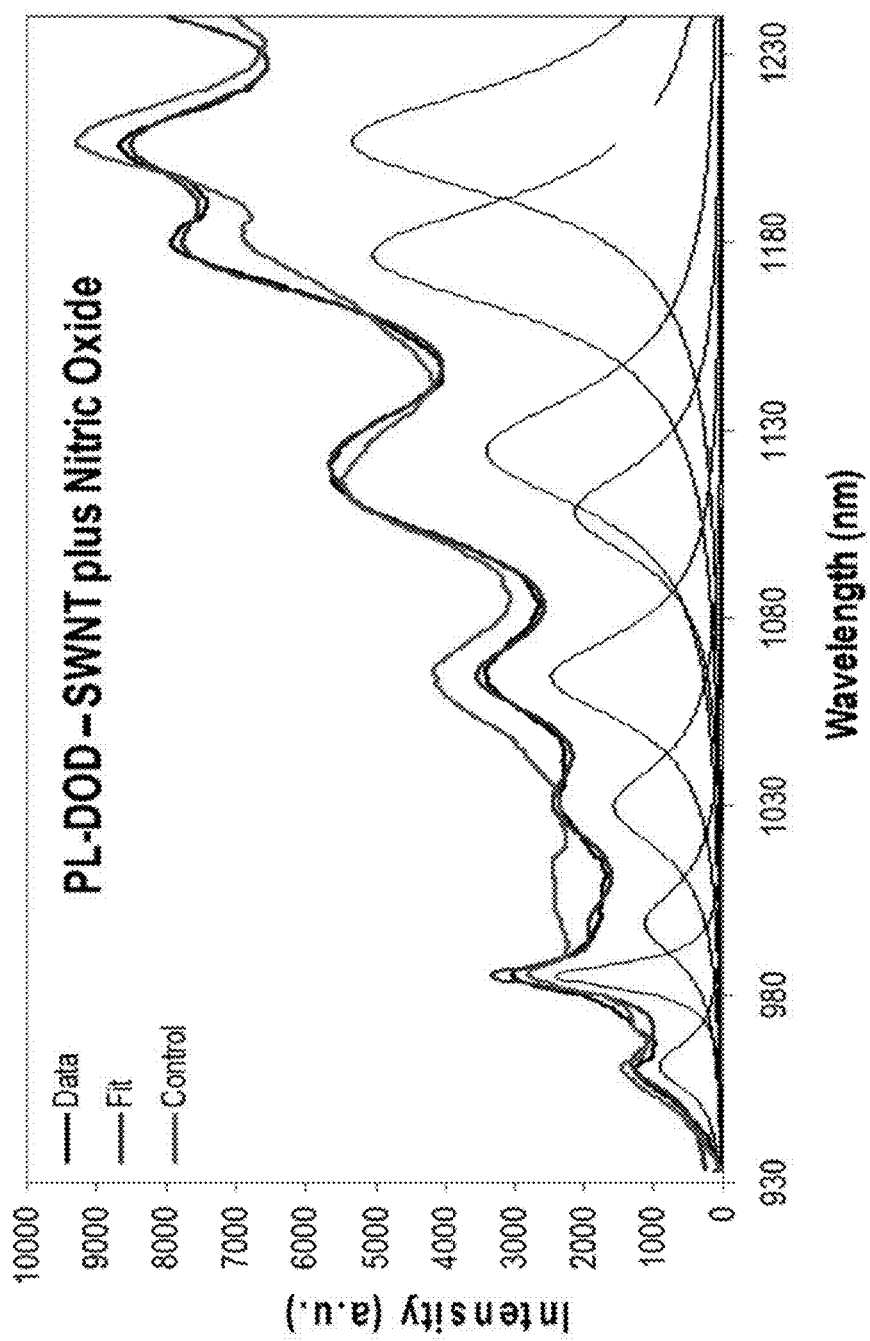

POLYMER-NANOSTRUCTURE COMPOSITION FOR SELECTIVE MOLECULAR RECOGNITION

CLAIM OF PRIORITY

This application claims priority to provisional U.S. Patent Application No. 61/325,599, filed Apr. 19, 2010, which is incorporated by reference in its entirety.

FEDERALLY SPONSORED RESEARCH OR DEVELOPMENT

This invention was made with government support under grant number NSF0753020 awarded by the National Science Foundation. The government has certain rights in this invention.

TECHNICAL FIELD

Systems and methods related to a polymer-nanostructure composition for selective molecular recognition are generally described.

BACKGROUND

Molecular recognition and signal transduction are two of the main challenges in sensor design. Molecular recognition can occur when a folded and constrained heteropolymer, orientated in three dimensional space creates a binding pocket or surface that can be identified by a specific counterpart. Nature generally offers few ways to enable molecular recognition, including antibodies and aptamers. Scientists and engineers can borrow from nature to gain analyte specificity and sensitivity, using natural antibodies as vital components of the sensor. However, antibodies can be expensive, fragile, and unstable, easily losing biological activity upon modification, such as immobilization, and exhibit batch-dependent variation. These characteristics can limit their use in widespread applications. Moreover, certain molecules of interest do not have a naturally existing antibody, including toxins, drugs and explosives.

Even with a solution for molecular recognition, measuring the analyte binding event can remain a challenge. For fluorescence-based sensors, a common method has been through Forster resonance energy transfer (FRET) between acceptor and donor fluorophores; however, such sensors usually require labeling. In certain circumstances, fluorescence based sensors can utilize fluorophores that photobleach over time, significantly limiting their capability for long-term continuous monitoring. Consequently, improved systems and methods for molecular recognition and detection are needed.

SUMMARY

In one aspect, a composition can include a complex, where the complex can include a nanostructure and a polymer, the polymer adsorbed on the nanostructure and the polymer being free from selective binding to an analyte in the absence of being adsorbed on the nanostructure, and a selective binding site associated with the complex.

In another aspect, a method for analyzing a sample for an analyte can include providing a composition which can include a complex, where the complex can include a nanostructure and a polymer, the polymer adsorbed on the nanostructure and the polymer being free from selective binding to an analyte in the absence of being adsorbed on the nanostructure, and a selective binding site associated with the complex, exposing the composition to a sample, monitoring a property of the composition, and determining a presence of an analyte in the sample based on the property.

In another aspect, a system can include a composition which can include a complex, where the complex can include a nanostructure and a polymer, the polymer adsorbed on the nanostructure and the polymer being free from selective binding to an analyte in the absence of being adsorbed on the nanostructure, and a selective binding site associated with the complex, an electromagnetic radiation source having an excitation wavelength directed at the composition, and a detector configured to receive an emission wavelength from the composition.

In some embodiments, the nanostructure can be a photoluminescent nanostructure. In some embodiments, the nanostructure can be a quantum dot, a nanowire, a nanotube, a carbon nanotube or a single-walled carbon nanotube.

In some embodiments, the polymer can be a polysaccharide. The polysaccharide can include peptidoglycans, lipopolysaccharides, amylase, chitin, chitosan, glycogen, cellulose, dextran, functionalized dextran, phenoxy functionalized dextran or boronic acid functionalized phenoxy dextran.

In some embodiments, the polymer can be a polynucleotide. The polynucleotide can be DNA or RNA. The polynucleotide can be single stranded or double stranded. The polynucleotide can be single stranded in one section and double stranded in another section. RNA can include mRNA, siRNA or shRNA.

The polynucleotide can form a structure. Exemplary nucleic acid structures can include an A-form double helix, a B-form double helix, a Z-form double helix, a hairpin, a loop or a stem loop.

The polynucleotide can have less than 100,000, less than 50,000, less than 25,000, less than 10,000, less than 5,000, less than 1,000, less than 500, less than 250, less than 100, less than 75, less than 50, less than 30, less than 25, less than 20, 15, 12, 10, 8, 6 or 4 nucleotides.

The polynucleotide can have a random sequence. The polynucleotide can have an ordered sequence. The ordered sequence can be a predetermined sequence. The ordered sequence can be a repeating sequence. The repeat sequence can include less than 500, less than 400, less than 300, less than 200, less than 100, less than 50, less than 30, less than 25, less than 20, 15, 14, 13, 12, 11, 10, 9, 8, 7, 6, 5, 4, 3 or 2 nucleotides. The polynucleotide can be poly(AT), poly(GT), poly(CT), poly(AG), poly(CG), or poly(AC). The polynucleotide can have a content. The content can be a percentage of a unique nucleotide present in the sequence.

In some embodiments, the polymer can be a polypeptide. In some embodiments, the number of amino acids including the polypeptide can fall within a specific range. For example, the polypeptide can include between 5 and about 50 amino acid residues, or between 5 and about 30 amino acid residues. In other embodiments, the polypeptide can fall within a specific molar mass range. For example, the polypeptide can have a molecular weight of between 400 g/mol and about 10,000 g/mol, or between 400 g/mol and about 6,000 g/mol. The polypeptide can be a protein, having greater than about 50 amino acid residues. The polypeptide can be a fragment of a protein. In some embodiments, the polypeptide can be expressed in a disease state. In other embodiments, the polypeptide can be modified. In some circumstances, the polypeptide can be modified by attaching functional groups. In other circumstances, the polypeptide can be ubiquinated, biotinylated, glycosylated, PEGylated or SUMOylated. The polypeptide can be a biomarker, an enzyme, a receptor, a ligand, a peptide hormone, a neuropeptide, a vasoactive intestinal peptide, a chaperone or an antibody.

In some embodiments, the polypeptide can, in some instances, include a peptide sequence observed in the venom of an animal or a derivative thereof. In some embodiments, the polypeptide can be a member the Mastoparan or Bombolitin families of polypeptides, or derivatives of those polypeptides. The polypeptide can include a mastoparan, mastoparan 7 or mastoparan X.

In some embodiments, the polymer can be a conjugate including a dye moiety. The dye moiety can be located at a terminus of a polymer. The dye moiety can include, for example, a fluorescent dye such as perylene derivatives, anthracene derivatives, indigoid and thioindigoid derivatives, imidazole derivatives, naphthalimide derivatives, xanthene derivatives, thioxanthene derivatives, coumarin derivatives, rhodamine derivatives, thiophene derivatives, fluorescein derivatives, tetracene derivatives, quinacridone derivatives, stilbene derivatives, distyryl arylene derivatives, tristyryl arylene derivatives, anthracene derivatives, berylline derivatives, coronene derivatives, dicyanomethylene pyran derivatives, dicyanomethylene thiopyran derivatives, cyanine derivatives or oxadine derivatives.

In some embodiments, the polymer can be a polylipid. The polylipid can include a phospholipid. The phospholipid can be a palmitoyl phospholipid. The palmitoyl phospholipid can be, for example, 1,2-dipalmitoyl-sn-glycero-3-phosphoethanolamine-N-(lauroyl).

In some embodiments, the polymer can be polyvinylpyrrolidone, a poly(ethylene oxide), a poly(ethylene oxide)-poly(propylene oxide)-poly (ethylene oxide) block co-polymer, poly (N-isopropyl acrylamide), polyethyleneimine, polyacrylamide, polyvinyl alcohol or collagen.

In some embodiments, the analyte can be a small molecule, protein, biomolecule, explosive, drug, biologic, or a metabolite thereof. For example, the analyte can be a monosaccharide, a polysaccharide, an amino acid, a nucleotide, an oligonucleotide, a lipid, a polylipid or a steroid. In other embodiments, the analyte can be a peptide or a protein. In some embodiments, the analyte can be riboflavin or nitric oxide. In some embodiments, the analyte can be $17$-$\alpha$-estradiol, 2,4-dinitrophenol, acetylcholine chloride, $\alpha$-tocopherol, adenosine, adenosine-5'-triphosphate, cyclic adenosine monophosphate, creatinine, cytidine, D-aspartic acid, D-fructose, D-galactose, D-glucose, D-mannose, dopamine, glycine, guanosine, histamine, L-ascorbic acid, L-citrulline, L-histidine, L-thyroxine, melatonin, NADH, quinine, salicylic acid, serotonin, sodium azide, sodium pyruvate, sucrose, thymidine, tryptophan, tyramin or urea. In some embodiments, the analyte can be a DNA sequence, a RNA sequence or a siRNA sequence.

In some embodiments, the composition can further include an amount of the analyte. In some embodiments, the analyte can be a therapeutic.

In some embodiments, the sample can include a gas, a liquid or a solid. In some embodiments, the sample can be a biological fluid.

In some embodiments, the property can be an emission. In some embodiments, the property can be an emission intensity or an emission wavelength.

In some embodiments, exposing the composition to a sample can include inserting the composition into an animal. In some embodiments, the animal can be a human. In other embodiments exposing the composition to a sample can include inserting the composition into a plant or fungus. In some embodiments, exposing the composition to a sample can include incubating the composition with a microorganism or a virus. In some embodiments, exposing the composition to a sample can include incubating the composition with a cell line. In other embodiments, exposing the composition to a sample can include incubating the composition with an in vitro model system.

In some embodiments, determining the presence of an analyte can include determining the absence of the analyte. In other embodiments, determining the presence of an analyte can include determining the concentration of the analyte, determining the purity of an analyte or determining a quantity of an analyte.

In some embodiments, the method for analyzing a sample for an analyte can further include obtaining a sample. In other embodiments, the method for analyzing a sample for an analyte can further include obtaining a sample from an animal. In some embodiments, the animal can be a human. In some embodiments, the method for analyzing a sample for an analyte can further include obtaining a sample from a microorganism or virus. In some embodiments, the method for analyzing a sample for an analyte can further include obtaining a sample from a plant or fungus. In other embodiments, the method for analyzing a sample for an analyte can further include obtaining a sample from a cell line.

In some embodiments, the method for analyzing a sample for an analyte can further include coating a glass slide with the composition.

In another aspect, a method can include providing a composition which can include a complex, where the complex can include a nanostructure and a polymer, the polymer adsorbed on the nanostructure and the polymer being free from selective binding to an analyte in the absence of being adsorbed on the nanostructure, and a selective binding site associated with the complex, exposing the composition to a mixture containing the analyte, and separating the composition from the mixture, thereby removing the analyte from the mixture.

In some embodiments, the nanostructure can be a photoluminescent nanostructure.

In another aspect, a method can include providing a composition which can include a complex, where the complex can include a nanostructure and a polymer, the polymer adsorbed on the nanostructure and the polymer being free from selective binding to an analyte in the absence of being adsorbed on the nanostructure, and a selective binding site associated with the complex and an amount of the analyte, where the analyte can be a therapeutic, and administering the composition to an animal.

In some embodiments, the nanostructure can be a photoluminescent nanostructure.

In some embodiments, the method can further include monitoring a property of the composition and determining the presence of the therapeutic in the composition based on the property.

In some embodiments, monitoring a property of the composition can be performed using a high-throughput system. In other embodiments, the composition can be exposed to a sample in a well in a well plate array.

In another aspect, a method for analyzing samples in a high-throughput system, can include providing an array of compositions, wherein each composition includes a complex, wherein the complex includes a nanostructure, and a polymer, the polymer adsorbed on the nanostructure and the polymer being free from selective binding to an analyte in the absence of being adsorbed on the nanostructure; and a selective binding site associated with the complex; exposing each composition to at least one sample; monitoring a property of each composition; and determining the presence of an analyte in the sample based on the property.

In another aspect, a method can include providing a composition which can include a complex, where the complex can include a nanostructure and a polymer, the polymer adsorbed on the nanostructure and the polymer being free from selective binding to an analyte in the absence of being adsorbed on the nanostructure, and a selective binding site associated with the complex and an amount of the analyte, and exposing the composition to a catalyst.

In some embodiments, the nanostructure can be a photoluminescent nanostructure.

In some embodiments, the method can further include monitoring a property of the composition and determining modification of the analyte based on the property.

Other embodiments are within the claims.

DETAILED DESCRIPTION

Figure 1:
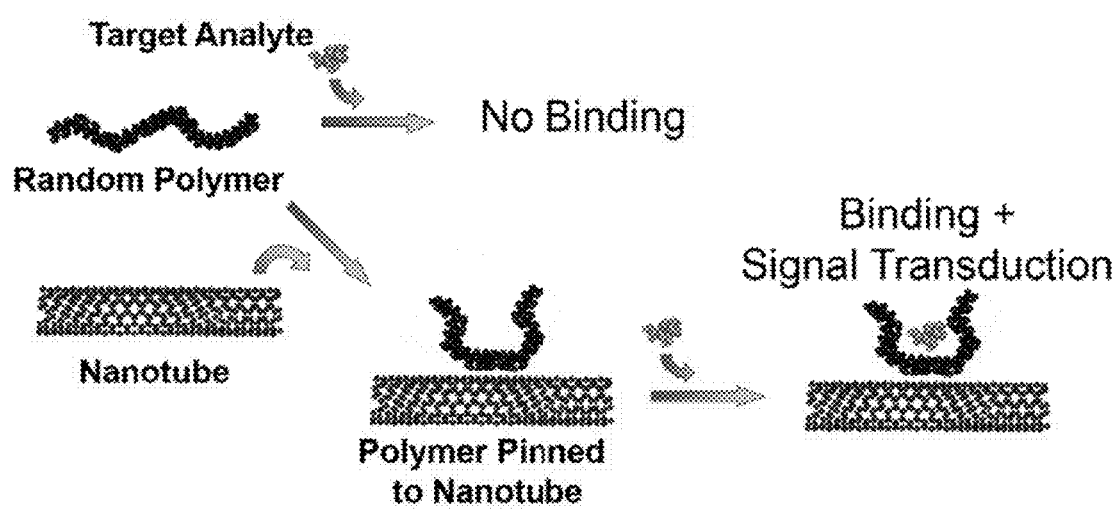
FIG. 1 is a schematic of the composition as a sensor.

Single-walled carbon nanotubes (SWNTs) can be cylindrical graphene layers. SWNTs can have nanometer-sized diameters and aspect ratios on the order of 1,000 to 1,000,000. SWNTs can possess band-gap photoluminescence in the near infrared (nIR). (O'Connell, M. J., et al., Band gap fluorescence from individual single-walled carbon nanotubes. *Science* 297, 593 (2002); Li, Q. et al., Sustained Growth of Ultralong Carbon Nanotube Arrays for Fiber Spinning *Adv. Mater* 18, 3160-3163 (2006); Heller, D. A., et al., Single-walled carbon nanotube spectroscopy in live cells: Towards long-term labels and optical sensors. *Advanced Materials* 17, 2793-2798 (2005), which are incorporated by reference in their entirety). SWNT photoluminescence has been used for the detection of β-D-glucose, DNA, divalent metal cations, genotoxins, reactive oxygen species, pH and the protein avidin. (O'Connell, M. J., et al., (2002); Barone, P. W., et al., Near-infrared optical sensors based on single-walled carbon nanotubes. *Nature Materials* 4, 86-92 (2005); Kim, J., et al., The rational design of nitric oxide selectivity in single-walled carbon nanotube near-infrared fluorescence sensors for biological detection. *Nature Chemistry* (2009); Satishkumar, B. C., et al., Reversible fluorescence quenching in carbon nanotubes for biomolecular sensing. *Nature Nanotechnology* 2, 560-564 (2007); Heller, D. A., et al., Optical detection of DNA conformational polymorphism on single-walled carbon nanotubes. *Science* 311, 508 (2006); Jeng, E. S., et al., Detection of DNA hybridization using the near-infrared band-gap fluorescence of single-walled carbon nanotubes. *Nano Letters* 6, 371-375 (2006); Cognet, L., et al., Stepwise quenching of exciton fluorescence in carbon nanotubes by single-molecule reactions. *Science* 316, 1465 (2007); Heller, D. A., et al., Multimodal optical sensing and analyte specificity using single-walled carbon nanotubes. *Nature Nanotechnology* (2008), which are incorporated by reference in their entirety). These sensor responses can use the sensitivity of SWNT photoluminescence to the adsorption of small molecule electron-donating or electron-withdrawing groups, which can result in a photoluminescence increase or decrease, respectively. (Barone, P. W. et al., (2005); Kim, J. et al., (2009); Satishkumar, B. C. et al., (2007)). Similarly, SWNT photoluminescence can also be sensitive to changes in local dielectric screening as polymer wrappings are functionalized or change conformation, which can cause either a red- or blue-shift in emission energy. (Heller, D. A. et al., (2006); Perebeinos, V., et al., Scaling of excitons in carbon nanotubes. *Physical Review Letters* 92, 257402 (2004); Walsh, A. G., et al., Screening of excitons in single, suspended carbon nanotubes. *Nano Lett* 7, 1485-1488 (2007), which are incorporated by reference in their entirety). Because a photobleaching threshold has not been observed with SWNTs, it is possible that sensors utilizing SWNTs could operate indefinitely allowing the continuous analyte monitoring that has previously been impossible.

The aforementioned SWNT photoluminescence based sensors took advantage of well-known interactions between the target analyte and the polymer or protein adsorbed on the SWNT surface. While this approach has been successful, it necessarily limits sensor design to well-known analyte-binding partner interactions and even then a method for detecting the molecular recognition event cannot be guaranteed.

As an alternative, a polymer, with little or no affinity for the target analyte, can adopt a specific conformation when adsorbed to the nanotube via non-covalent interactions. In this approach, the polymer can be pinned in place such that a selective binding site can be created that recognizes the target molecule, and the binding event can lead to changes in the photoluminescence emitted (FIG. 1). The polymer-nanotube composition can act as a binding partner for the analyte, which results in a detectable change in photoluminescence. No labeling is needed in this technique; however, labeling can be performed. For example, one or more fluorescent dyes can be conjugated to the polymer through covalent reaction with a functionality along the polymer backbone or at a polymer terminus.

A systematic design of polymers for understanding molecular structures of polymers that are capable of complexing or interacting with a nanostructure can include adjusting the hydrophilic and hydrophobic regions of the polymer. Each of the fluorescent moiety and the polymer backbone moiety can be selected to have a length of a hydrophilic region and length of a hydrophobic region configured to interact in with a nanostructure. Selecting can include adjusting the length of the polymer moiety. Therefore, in addition to interacting with an analyte, the systemically designed polymer can suspend a nanoparticle in an aqueous solution. The length and hydrophilicity of the hydrophilic regions can be altered to achieve the desired solubility. For example, the molecular weight of a PEG conjugate can be increased or decreased to alter the solubility of composition including the polymer and a nanoparticle. In another example, a conjugate of the polymer with another moiety can be formed. The other moiety can be a fluorescent moiety which is coupled to a selected polymer backbone moiety.

For example, the polymer can be designed to have structures that are simple enough to allow for distinct fluorescence responses for different molecules, while also enabling polymer-nanostructure complexes to be simulated with, for example, molecular dynamics simulation or mean-field based model. For example, fluorescein or rhodamine can be conjugated with polyethylene glycol polymers. These conjugate polymers can be designed to provide fluorophores on the polymers that can assist in identifying structural information of the polymer-nanostructure complexes or to study the basics of the interactions between the nanostructure and the polymer. Hydrophilic regions of the polymer can extend into water, while hydrophobic regions can interact with nanostructure surface. Therefore, the length of the hydrophilic region can be tuned by the molecular weights of the polymer, for example, the polyethylene glycol (PEG).

A conjugate can be formed by reaction between one or more of a carboxylic acid, ester, aldehyde, aldehyde hydrate, acetal, hydroxy, protected hydroxy, carbonate, alkenyl, acrylate, methacrylate, acrylamide, substituted or unsubstituted thiol, halogen, substituted or unsubstituted amine, protected amine, hydrazide, protected hydrazide, succinimidyl, isocyanate, isothiocyanate, dithiopyridine, vinylpyridine, iodoacetamide, epoxide, hydroxysuccinimidyl, azole, maleimide, sulfone, allyl, vinylsulfone, tresyl, sulfo-N-succinimidyl, dione, mesyl, tosyl, or glyoxal. Specific examples can include N-succinimidyl carbonate, amine, hydrazide, succinimidyl propionate, succinimidyl butanoate, succinimidyl succinate, succinimidyl ester, benzotriazole carbonate, glycidyl ether, oxycarbonylimidazole, p-nitrophenyl carbonate, aldehyde, maleimide, and orthopyridyldisulfide, vinylsulfone.

In other circumstances, the polymer can be branched or modified in other ways to alter or adjust the properties of the complex. For example, the polymer can be a comb, brush or star-burst polymer. For example, the polymer can be branched, having 2-20 arms. In certain examples, the branched polymer can be a polyethylene glycol polymer having 2, 4 or 8 arm groups.

Generally, the composition can include a complex and a selective binding site associated with the complex. The complex can include a nanostructure and a polymer, the polymer being free from selective binding to an analyte in the absence of being adsorbed on the nanostructure. The polymer can be adsorbed on the nanostructure. The nanostructure can be a photoluminescent nanostructure.

A nanostructure can be an article having at least one cross-sectional dimension between opposed boundaries of less than about 1 micron. In some embodiments, nanostructures can have at least one cross-sectional dimension between opposed boundaries of less than about 500 nm, less than about 250 nm, less than about 100 nm, less than about 75 nm, less than about 50 nm, less than about 25 nm, less than about 10 nm, or, in some cases, less than about 1 nm. Examples of nanostructures can include nanotubes (including carbon nanotubes), nanowires (including carbon nanowires), graphene and quantum dots, among others. In some embodiments, the nanostructures can include a fused network of atomic rings, the atomic rings can include a plurality of double bonds.

A photoluminescent nanostructure can be a class of nanostructures that can exhibit photoluminescence. In some embodiments, photoluminescent nanostructures can exhibit fluorescence. In some instances, photoluminescent nanostructures can exhibit phosphorescence. Examples of photoluminescent nanostructures suitable for use can include, but are not limited to, single-walled carbon nanotubes (SW-CNTs), double-walled carbon nanotubes (DWCNTs), multi-walled carbon nanotubes (MWCNTs), semi-conductor quantum dots, semi-conductor nanowires, or graphene, among others. In some embodiments, the photoluminescent nanostructures can be a semi-conductive single-walled carbon nanotube.

Selective binding can be sufficiently specific that it can be used to distinguish the analyte from other chemical species. The polymer can be considered random because, in the absence of the complex, the polymer has little or no affinity for the analyte (FIG. 1).

In some embodiments, the polymer can be a polysaccharide. The polysaccharide can include peptidoglycans, lipopolysaccharides, amylase, chitin, chitosan, glycogen, cellulose, dextran, functionalized dextran, phenoxy functionalized dextran or boronic acid functionalized phenoxy dextran.

In some embodiments, the polymer can be a polynucleotide. The polynucleotide can be DNA or RNA. The polynucleotide can be single stranded or double stranded. The polynucleotide can be single stranded in one section and double stranded in another section. RNA can include mRNA, siRNA or shRNA.

The polynucleotide can form a structure. Exemplary nucleic acid structures can include an A-form double helix, a B-form double helix, a Z-form double helix, a hairpin, a loop or a stem loop.

The polynucleotide can contain ribonucleotides or deoxyribonucleotides. The polynucleotide can have less than 100,000, less than 50,000, less than 25,000, less than 10,000, less than 5,000, less than 1,000, less than 500, less than 250, less than 100, less than 75, less than 50, less than 30, less than 25, less than 20, 15, 12, 10, 8, 6 or 4 nucleotides.

The polynucleotide can have a random sequence. The polynucleotide can have an ordered sequence. The ordered sequence can be a predetermined sequence. For example, an ordered sequence can be the sequence of a gene. The ordered sequence can be a repeating sequence. The repeat sequence can include less than 500, less than 400, less than 300, less than 200, less than 100, less than 50, less than 30, less than 25, less than 20, 15, 14, 13, 12, 11, 10, 9, 8, 7, 6, 5, 4, 3 or 2 nucleotides. The polynucleotide can be poly(AT), poly (GT), poly(CT), poly(AG), poly(CG), or poly(AC). The polynucleotide can have a content. The content can be a percentage of a unique nucleotide present in the sequence. The percentage can be 100% of a unique nucleotide, including poly(A), poly(C), poly(G), poly(T) or poly(U).

In some embodiments, the polymer can be a polylipid. The polylipid can include a phospholipid, a palmitoyl phospholipid or 1,2-dipalmitoyl-sn-glycero-3-phosphoethanolamine-N-(lauroyl) (PL-DOD).

In other embodiments, the polymer can be polyvinylpyrrolidone, a poly(ethylene oxide), a poly(ethylene oxide)-poly (propylene oxide)-poly (ethylene oxide) block co-polymer, poly (N-isopropyl acrylamide), polyethyleneimine, polyacrylamide, polyvinyl alcohol or collagen.

In some embodiments, the polymer can be a polypeptide. In some embodiments, the number of amino acids comprising the polypeptide can fall within a specific range. For example, the polypeptide can include between 5 and about 50 amino acid residues, or between 5 and about 30 amino acid residues. In other embodiments, the polypeptide can fall within a specific molar mass range. For example, the polypeptide can have a molecular weight of between 400 g/mol and about 10,000 g/mol, or between 400 g/mol and about 6,000 g/mol. The polypeptide can be a protein, having greater than about 50 amino acid residues. The polypeptide can be a fragment of a protein. In some embodiments, the polypeptide can be expressed in a disease state. In other embodiments, the polypeptide can be modified. In some circumstances, the polypeptide can be modified by attaching functional groups. In other circumstances, the polypeptide can be ubiquinated, biotinylated, glycosylated, PEGylated or SUMOylated. The polypeptide can be a biomarker, an enzyme, a receptor, a ligand, a peptide hormone, a neuropeptide, a vasoactive intestinal peptide, a chaperone or an antibody.

The polypeptide can, in some instances, include a peptide sequence observed in the venom of an animal or a derivative thereof. In some cases, the polymer can include a polypeptide sequence (or derivative thereof) observed in the venom of a member of the Insecta class, the Hymenoptera order, or the Vespidae or Apidae families. In some embodiments, the polypeptide can be a member the Mastoparan or Bombolitin (including Bombolitin II, Bombolitin III) families of polypeptides, or derivatives of those polypeptides. The polypeptide can include a mastoparan, mastoparan 7 or mastoparan X.

Figure 4A:
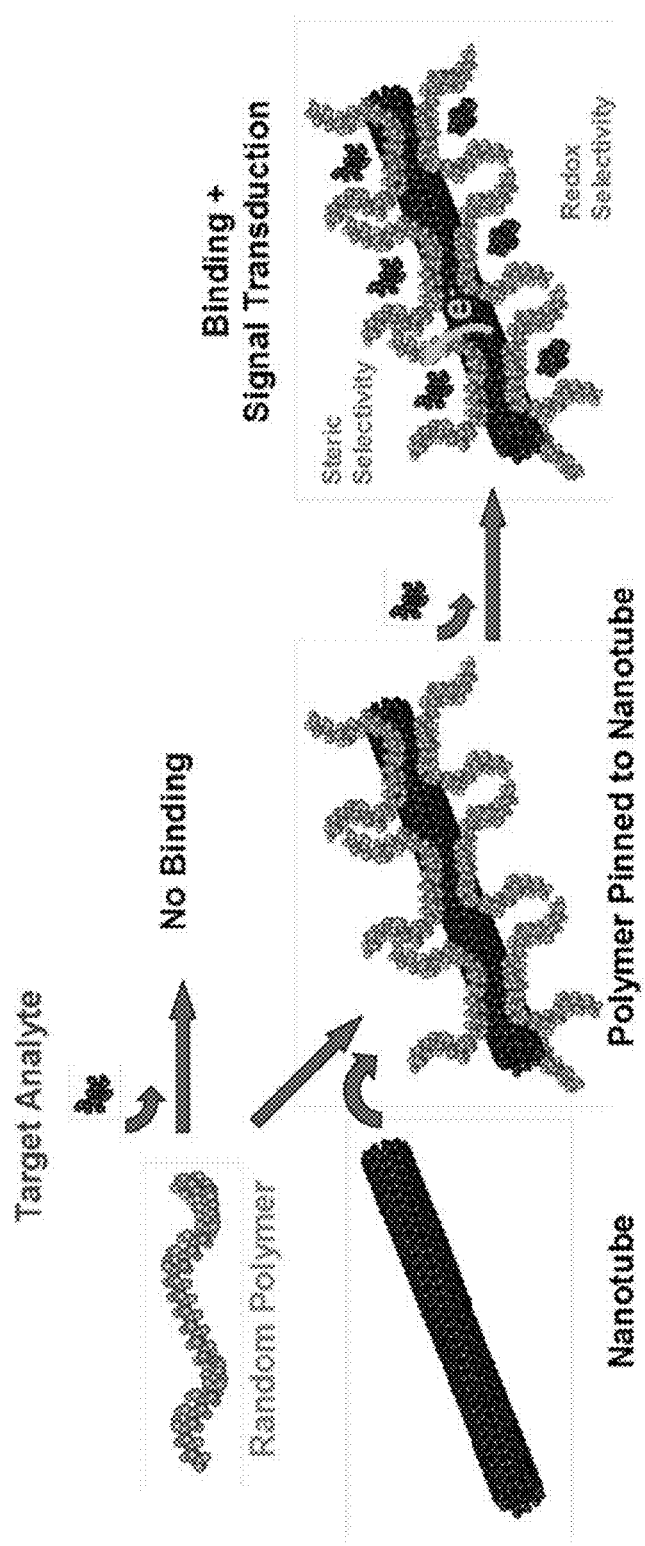
FIG. 4 is (a) a schematic of the composition as a sensor and (b)-(d) plots of optical signal transduction following recognition of the target molecule.

In the complex, the polymer can be adsorbed on the photoluminescent nanostructure. While FIGS. 1 and 4*a* show individual polymers being adsorbed or pinned to one point on the nanotube, it should be understood that the polymer can assume any suitable shape or configuration on the nanotube.

While the polymer can be free from selective binding to the analyte, the composition can include a selective binding site associated with the complex (FIG. 1). The selective binding site can be associated with the polymer. The selective binding site can also be associated with the nanostructure. Additionally, the selective binding site can be associated with both the polymer and the nanostructure.

Changing the ratio of the amount of polymer to the amount of photoluminescent nanostructure can result in different compositions, which can interact differently with an analyte. Changing the ratio of a first type of monomer in the polymer to a second type of monomer in the polymer also can result in different compositions. For example, the ratio of the amount of boronic acid functionalized phenoxy dextran to the amount of phenoxy dextran in the polymer can be altered to change the polymer. A different polymer can result in a different selective binding site. A different polymer can alter a property of the composition. The property can be an emission.

The diameter of a photoluminescent nanostructure can be different from the diameter of another photoluminescent nanostructure. The diameter of the photoluminescent nanostructure can affect the adsorption of the polymer on the photoluminescent nanostructure. The diameter of the photoluminescent nanostructure can affect the selective binding site. The diameter of the photoluminescent nanostructure can affect a property of the composition. The property of the composition can be an emission.

Carbon nanotubes can be classified by the chiral vector (n,m) that can characterize the orientation of the carbon hexagons in a corresponding graphene sheet. The chiral vector of a photoluminescent nanostructure can be different from the diameter of another photoluminescent nanostructure. The chiral vector of the photoluminescent nanostructure can affect the adsorbtion of the polymer on the photoluminescent nanostructure. The chiral vector of the photoluminescent nanostructure can affect the selective binding site. The chiral vector of the photoluminescent nanostructure can affect a property of the composition. The property of the composition can be an emission.

In some embodiments, the analyte can be a a small molecule, protein, biomolecule, explosive, drug, biologic, or a metabolite thereof. For example, the analyte can be monosaccharide, a polysaccharide, an amino acid, a nucleotide, an oligonucleotide, a lipid, a polylipid or a steroid. More specifically, the analyte can be riboflavin or nitric oxide. In some embodiments, the analyte can be 17-α-estradiol, 2,4-dinitrophenol, acetylcholine chloride, α-tocopherol, adenosine, adenosine-5'-triphosphate, cyclic adenosine monophosphate, creatinine, cytidine, D-aspartic acid, D-fructose, D-galactose, D-glucose, D-mannose, dopamine, glycine, guanosine, histamine, L-ascorbic acid, L-citrulline, L-histidine, L-thyroxine, melatonin, NADH, quinine, salicylic acid, serotonin, sodium azide, sodium pyruvate, sucrose, thymidine, tryptophan, tyramin or urea. In some embodiments, the analyte can be a DNA sequence, a RNA sequence or a siRNA sequence.

In other embodiments, the analyte can be a peptide or a protein. In some embodiments, the number of amino acids comprising the polypeptide can fall within a specific range. For example, the polypeptide can include between 5 and about 50 amino acid residues, or between 5 and about 30 amino acid residues. In other embodiments, the polypeptide can fall within a specific molar mass range. For example, the polypeptide can have a molecular weight of between 400 g/mol abd about 10,000 g/mol, or between 400 g/mol and about 6,000 g/mol. The polypeptide can be a protein, having greater than about 50 amino acid residues. The polypeptide can be a fragment of a protein. In some embodiments, the polypeptide can be expressed in a disease state. In other embodiments, the polypeptide can be modified. In some circumstances, the polypeptide can be modified by attaching functional groups. In other circumstances, the polypeptide can be ubiquinated, biotinylated, glycosylated, PEGylated or SUMOylated. The polypeptide can be a biomarker, an enzyme, a receptor, a ligand, a peptide hormone, a neuropeptide, a vasoactive intestinal peptide, a chaperone or an antibody.

The composition can be used for analyzing a sample for an analyte. The method for analyzing a sample for an analyte can include providing a composition which can include a complex and a selective binding site associated with the complex. The complex can include a photoluminescent nanostructure and a polymer free from selective binding to an analyte. The polymer can be adsorbed on the photoluminescent nanostructure. The method can include exposing the composition to a sample. The method can also include monitoring a property of the composition. The method can include determining the presence of an analyte in the sample based on the property.

In some embodiments, the sample can include a gas, a liquid or a solid. In other embodiments, the sample can be a biological fluid.

In some embodiments, exposing the composition to a sample can include inserting the composition into an animal. In particular, the animal can be a human. In other embodiments, exposing the composition to a sample can include inserting the composition into a plant or fungus. Inserting can include embedding the composition within the organism, embedding the composition within a cell of the organism, puncturing the organism with the composition or inserting the composition in a natural opening of the organism, among others.

Exposing the composition to a sample can also include incubating the composition with a microorganism or a virus. Exposing the composition to a sample can include incubating the composition with a cell line. In still other embodiments, exposing the composition to a sample can include incubating the composition with an in vitro model system.

In some embodiments, the property can be an emission. More specifically, the emission can be photoluminescence. The photoluminescence can be fluorescence or phosphorescence. In some embodiments, the property can be emission intensity. In other embodiments, the property can be an emission wavelength.

Monitoring the property can include observing the property of the composition alone. Monitoring the property can include monitoring the property after the composition has been exposed to the sample. Monitoring the property can include monitoring the property after the composition has been exposed to the analyte. Monitoring the property can include monitoring the property after the composition has been exposed to known concentrations of the analyte.

Monitoring a property of the composition can include observing the property through a microscope. Monitoring a property of the composition can include measuring the property using a microscope. The microscope can be a near infrared microscope. The microscope can be a dual-channel microscope. Monitoring a property of the composition can include monitoring the property using still photography or movies. The photography or movies can be on film media or digital form.

Determining the presence of an analyte can include determining the absence of the analyte. In some embodiments, determining the presence of an analyte can include determining the concentration of the analyte, determining the purity of the analyte or determining the quantity of the analyte. In some embodiments, relatively low concentrations or quantities of an analyte can be determined. The ability to determine low concentrations of an analyte may be useful, for example, in detecting trace pollutants or trace amounts of toxins within a subject. In some embodiments, analyte concentrations of less than about 100 micromolar, less than about 10 micromolar, less than about 1 micromolar, less than about 100 nanomolar, less than about 10 nanomolar, or less than about 1 nanomolar can be determined. The quantity of the analyte that can be determined can be less than 1 mole, less than 1 millimole, less than 1 micromole, less than 1 nanomole, less than 1 picomole, less than 1 femtomole, less than 1 attomole or less than 1 zeptomole. In some cases, a single molecule of an analyte can be determined. The purity of the analyte can be greater than 25% pure, greater than 50%, greater than 75% pure, greater than 80%, greater than 85% pure, greater than 90% pure, greater than 95% pure, greater than 99% pure or greater than 99.9% pure.

In some embodiments, the method for analyzing a sample for an analyte further includes obtaining a sample. More specifically, the method can include obtaining a sample from an animal, a microorganism, virus, plant, fungus or cell line. The animal can be a human. A sample can be obtained by drawing blood or other bodily fluids, biopsy, scraping, excision, lysis or plucking, among others.

Figure 18:
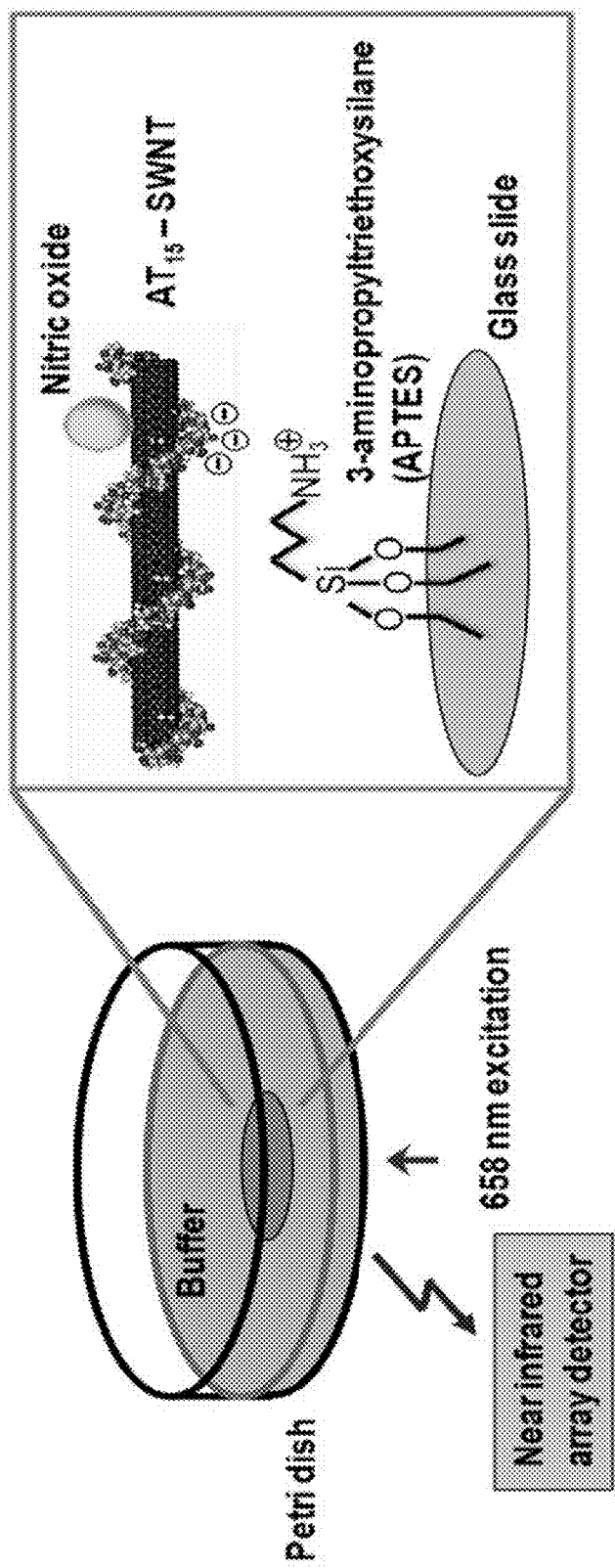
FIG. 18 is a schematic of the single molecule nitric oxide detection platform.
Figure 19A:
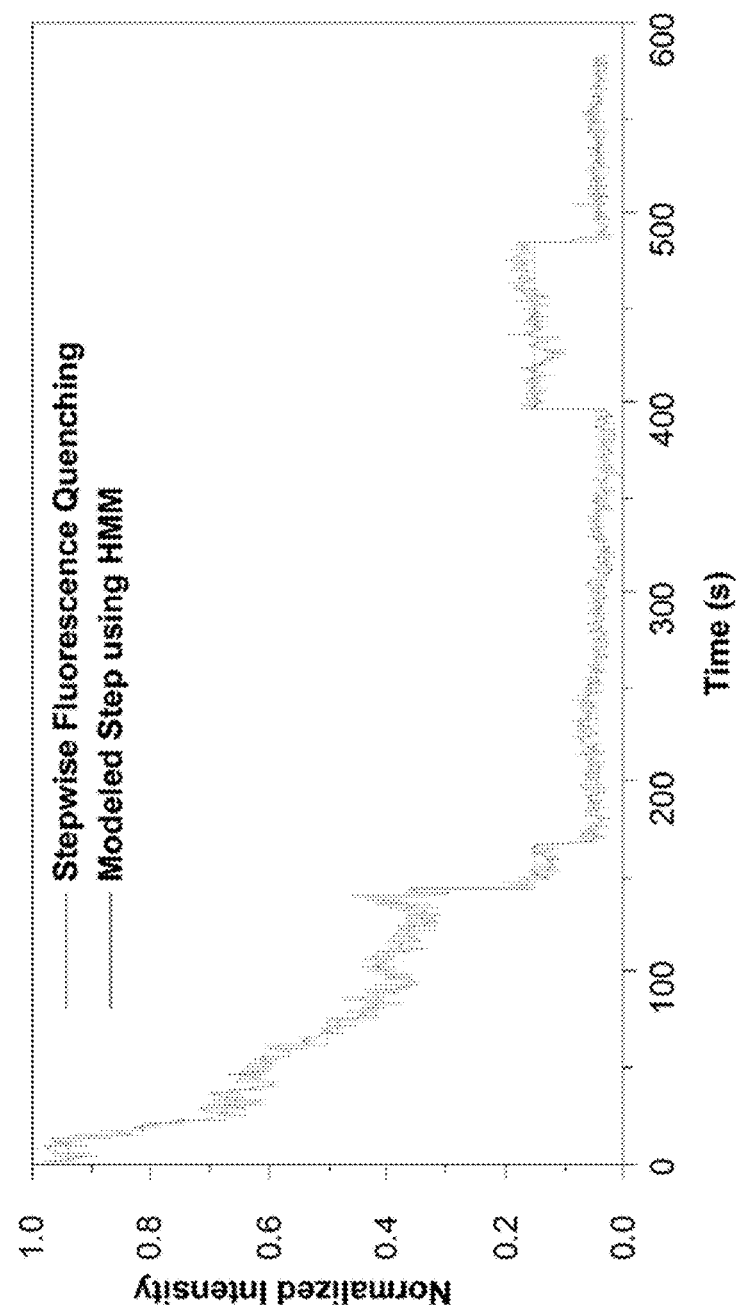
FIG. 19 shows four plots of typical reversible stepwise photoluminescence responses of a diffraction-limited segment from individual $AT_{15}$-SWNTs deposited on Petri dish, exposed to nitric oxide.
Figure 19B:
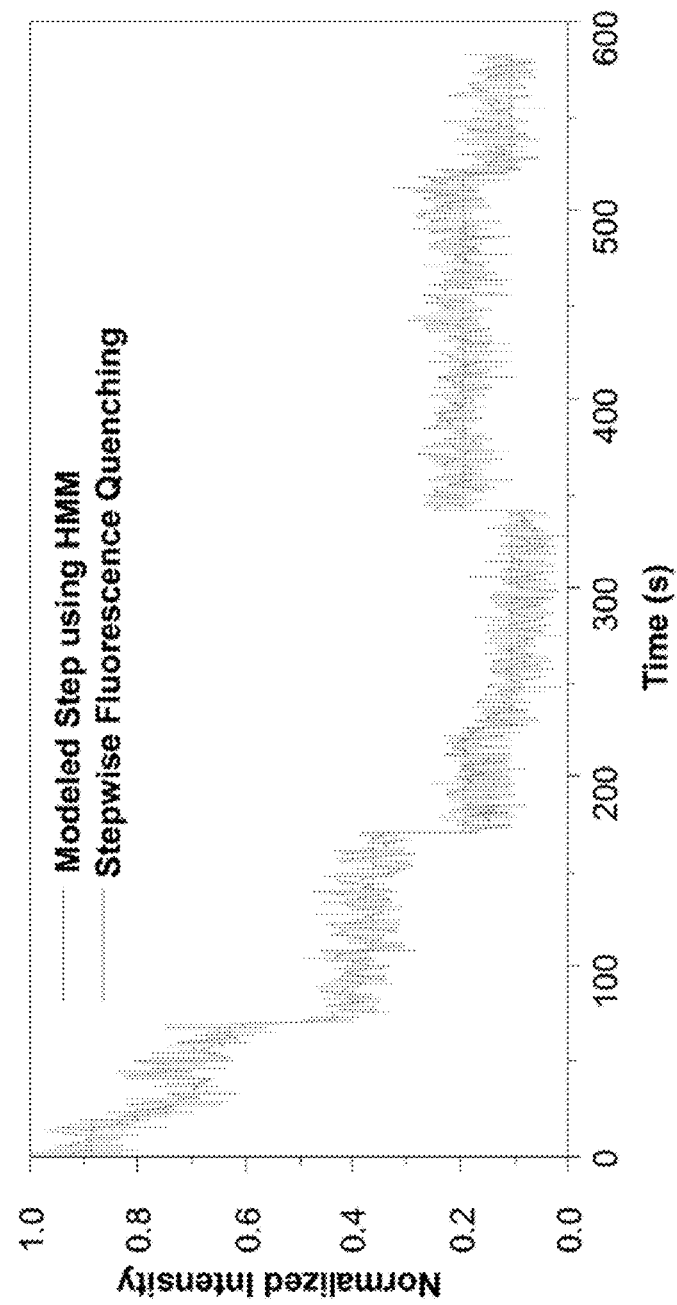
Figure 19C:
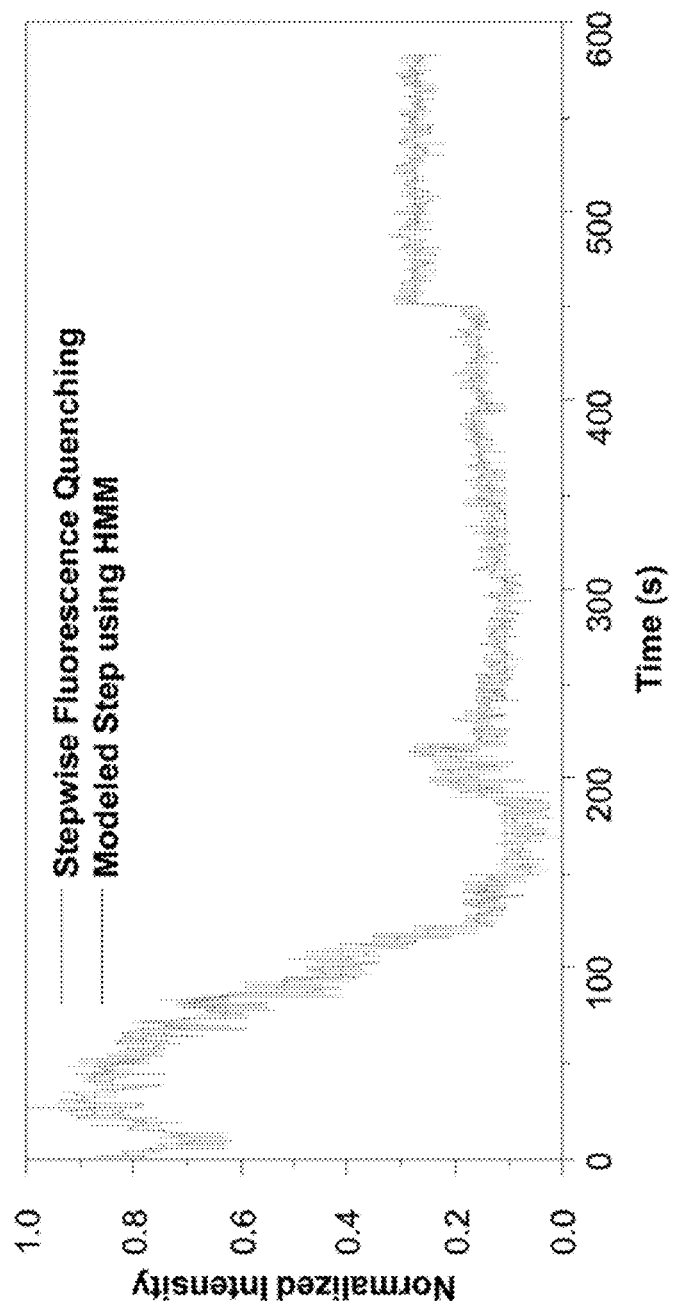
Figure 19D:
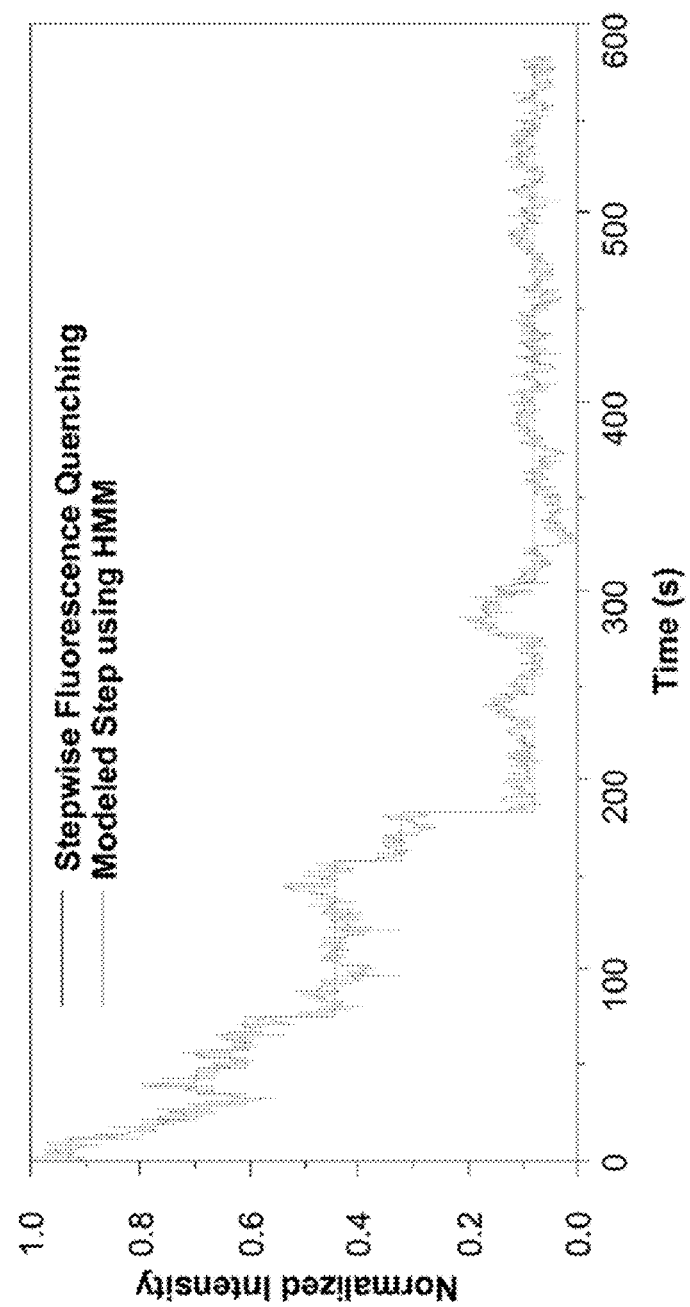

In some embodiments, the method for analyzing a sample for an analyte includes coating a glass slide with the composition (FIG. 18). The glass slide can be treated with a silane prior to coating with the composition. The silane can enhance adhesion of the composition to the glass slide. The silane can be 3-aminopropyltriethoxysilane (APTES).

In one aspect, a system can include a composition which can include a complex and a selective binding site associated with the complex. The complex can include a photoluminescent nanostructure and a polymer, the polymer being free from selective binding to an analyte in the absence of being adsorbed on the nanostructure. The polymer can be adsorbed on the photoluminescent nanostructure. The system can include an electromagnetic radiation source having an excitation wavelength directed at the composition. The system can include a detector configured to receive an emission wavelength from the composition.

The electromagnetic radiation source can be a light source. The electromagnetic radiation source can be a laser. The electromagnetic radiation can include radio waves, microwaves, terahertz radiation, infrared radiation, visible light, ultraviolet radiation, X-rays and gamma rays. The electromagnetic radiation can have an excitation wavelength in the visible spectrum, near infrared spectrum or infrared spectrum.

The detector can include a near infrared detector. The detector can include a near infrared fluorometer. The detector can be mounted on a microscope.

One advantage of the composition can be that for target protein or protein therapeutic detection the need to tag or label the target therapeutic to enable detection can be eliminated. One advantage of the composition can be that composition will bind directly to the analyte. Another advantage of the composition can be that the composition will work for detecting small molecules, antibodies, antibody fragments, proteins, and peptide fragments. An additional advantage of the composition can be that the composition can detect molecules for which there is no known binding partner. An advantage of the composition can be that, due to the non-photobleaching nature of SWNT, the composition can allow for continuous detection of the target analyte.

The composition can also be used for separation techniques. The method can include providing a composition. The composition can include a complex and a selective binding site associated with the complex. The complex can include a photoluminescent nanostructure and a polymer, the polymer being free from selective binding to an analyte in the absence of being adsorbed on the nanostructure. The polymer can be adsorbed on the photoluminescent nanostructure. The method can include exposing the composition to a mixture containing the analyte. The method can include separating the composition from the mixture. Separating the composition from the mixture can remove the analyte from the mixture.

An advantage of the composition can be that the composition may be able separate molecules for which there is no known binding partner. Another advantage of the compositions may be that the composition will work for the separation of analytes, including small molecules, antibodies, antibody fragments, proteins, and peptide fragments, among others. An advantage of the composition can be that one complex may be capable of binding multiple target molecules. Binding of multiple target molecules may allow for enhanced separation. An advantage of the composition can be that the separation process can be scalable.

In some embodiments, the composition can further include an amount of the analyte. In some embodiments, the analyte is a therapeutic. The composition can be used to deliver the therapeutic. The method can include providing a composition that includes an amount of the therapeutic. The method can include administering the composition to an animal. Administering the composition can include administering the composition by topical, enteral, parenteral, transdermal, transmucosal, inhalational, intracisternal, epidural, intravaginal, intravenous, intramuscular, subcutaneous, intradermal or intravitreal administration.

In some embodiments, the method can further include monitoring a property of the composition. The method can also include determining the presence of the therapeutic in the composition based on a property. The property can be an emission, an emission intensity or an emission wavelength. Determining the presence of the therapeutic can include determining the presence, the absence or the concentration of the therapeutic.

One advantage of the composition, which can include a therapeutic, can be the possibility of a multivalent interaction between the polymer-SWNT and the drug. The possibility of a multivalent interaction may be due to multiple binding sites along the length of the nanotube. The possibility can also mean the composition drug efficacy would be higher. Another advantage of the composition can be a concentrated drug release from the composition. A concentrated drug release may be due to one nanotube potentially containing many therapeutic molecules. An advantage of the composition can be resistance of the therapeutic to enzymatic degradation in the blood. This can be because the therapeutic can be shielded or protected within the composition. Still another advantage can be the possibility of tracing the pharmacokinetic pathways. Tracing the pharmacokinetic pathways of the drug may elucidate in vivo reaction pathways and enhance further drug design. Tracing may be possible because the SWNT NIR fluorescence is tissue transparent.

The composition can also be used in catalysis reactions. The method can include providing the composition, including an amount of the analyte. The method can include exposing the composition to a catalyst. The method can further include monitoring a property of the composition. The method can also include determining modification of the analyte based on the property.

An advantage of the composition can be the possibility to do site-specific functionalization of target proteins, antibodies, antibody fragments and peptides. Another advantage of the composition can be the possibility to do site-specific small molecule reactions. The small molecule reactions can be similar to those done in nature by enzymatic reactions.

A method for making the composition can include suspending the photoluminescent nanostructure in a surfactant. The surfactant can contain the polymer. The surfactant can be anionic. The surfactant can be sodium cholate. The suspension can be agitated. The agitation can evenly distribute the nanostructures. The agitation can prevent the nanostructures from aggregating. The agitation can include sonication. Aggregates can be removed from the suspension. Aggregates can be removed by discarding a pellet following centrifugation. The polymer can be added to the surfactant after aggregates are removed. The method can include removing the surfactant. Dialysis can be used to remove the surfactant. Removal of the surfactant can allow for the polymer to self-assemble on the nanostructure.

A method for making the composition can include suspending the photoluminescent nanostructure and the polymer in a salt solution. The salt solution can be sodium chloride. The method can also include suspending the photoluminescent nanostructure and the polymer in an organic compound solution. The organic compound solution can be a buffer. The buffer can have an effective pH range between 7.0 and 9.5. The buffer can be tris(hydroxymethyl)aminomethane. The suspensions can be agitated. The agitation can evenly distribute the photoluminescent nanostructure. The agitation can prevent the nanostructures from aggregating. The agitation can include sonication. Aggregates can be removed from the suspension. Aggregates can be removed by discarding a pellet following centrifugation.

A method for determining analytes recognized by the selective binding site in the composition can include exposing different compositions to an analyte. Two or more compositions can be different from one another because the compositions contain different polymers from one another. Two or more compositions can be different from one another because the compositions contain the same polymer of different lengths. Two or more compositions can also be different from one another because the compositions contain polymers that are comprised monomers in different ratios. Two or more compositions can be different from one another because the compositions contain the same monomers but in one polymer the monomers are modified. Two or more compositions can be different from one another because the compositions contain different photoluminescent nanostructures. Two or more compositions can be different from one another because the compositions contain photoluminescent nanostructures of different diameters. Two or more compositions can be different from one another because the compositions contain photoluminescent nanostructures with different chiral vectors.

A method for determining analytes recognized by the selective binding site in the composition can include exposing different analytes to a composition.

A method for determining analytes recognized by the selective binding site in the composition can include monitoring a property of the composition. The property can be an emission, emission intensity or emission wavelength. Monitoring the property can include observing the property of the composition alone. Monitoring the property can include monitoring the property after the composition has been exposed to a sample. Monitoring the property can include monitoring the property after the composition has been exposed to the analyte. Monitoring the property can include monitoring the property after the composition has been exposed to known concentrations of the analyte. Monitoring the property of the composition can provide a data set associated with an analyte.

The data set can include the emission of the photoluminescent nanostructure. The data set can include a change in emission intensity observed between a first emission intensity in the presence of the analyte and a second emission intensity in the absence of the analyte. The data set can include a change in emission wavelength shift observed between an emission wavelength in the presence of the analyte and an emission wavelength in the absence of the analyte. The data set can include data obtained from applying algorithms to the data obtained by monitoring the property. The data set can include binding constants. The data set can be used to determine if the composition can selectively bind to the analyte. The data set can be used to determine if the composition binding to the analyte can be detected by monitoring a property of the composition.

Figure 13:
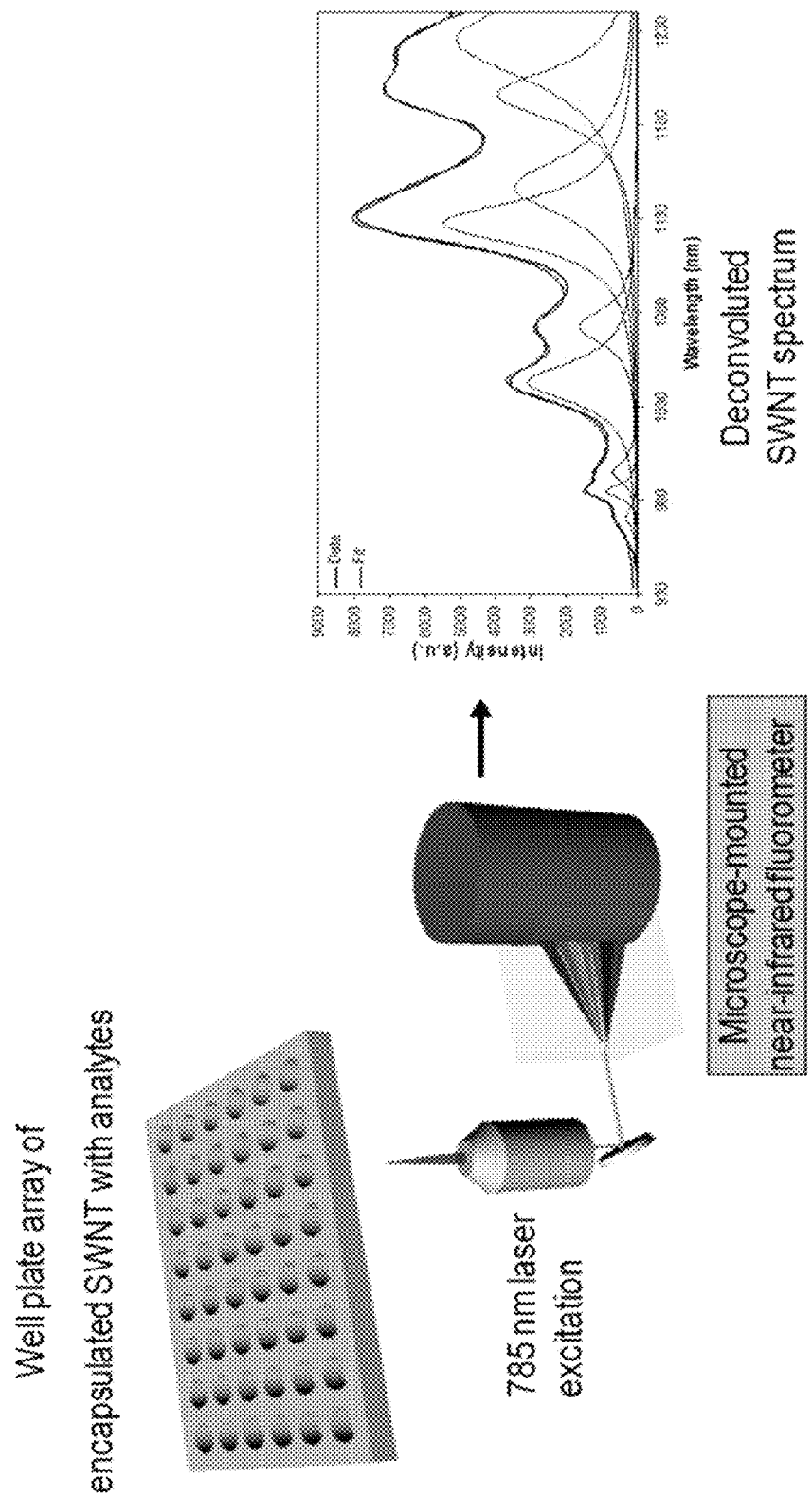
FIG. 13 is a schematic of the setup for high throughput screening assay and data analysis.
Figure 14:
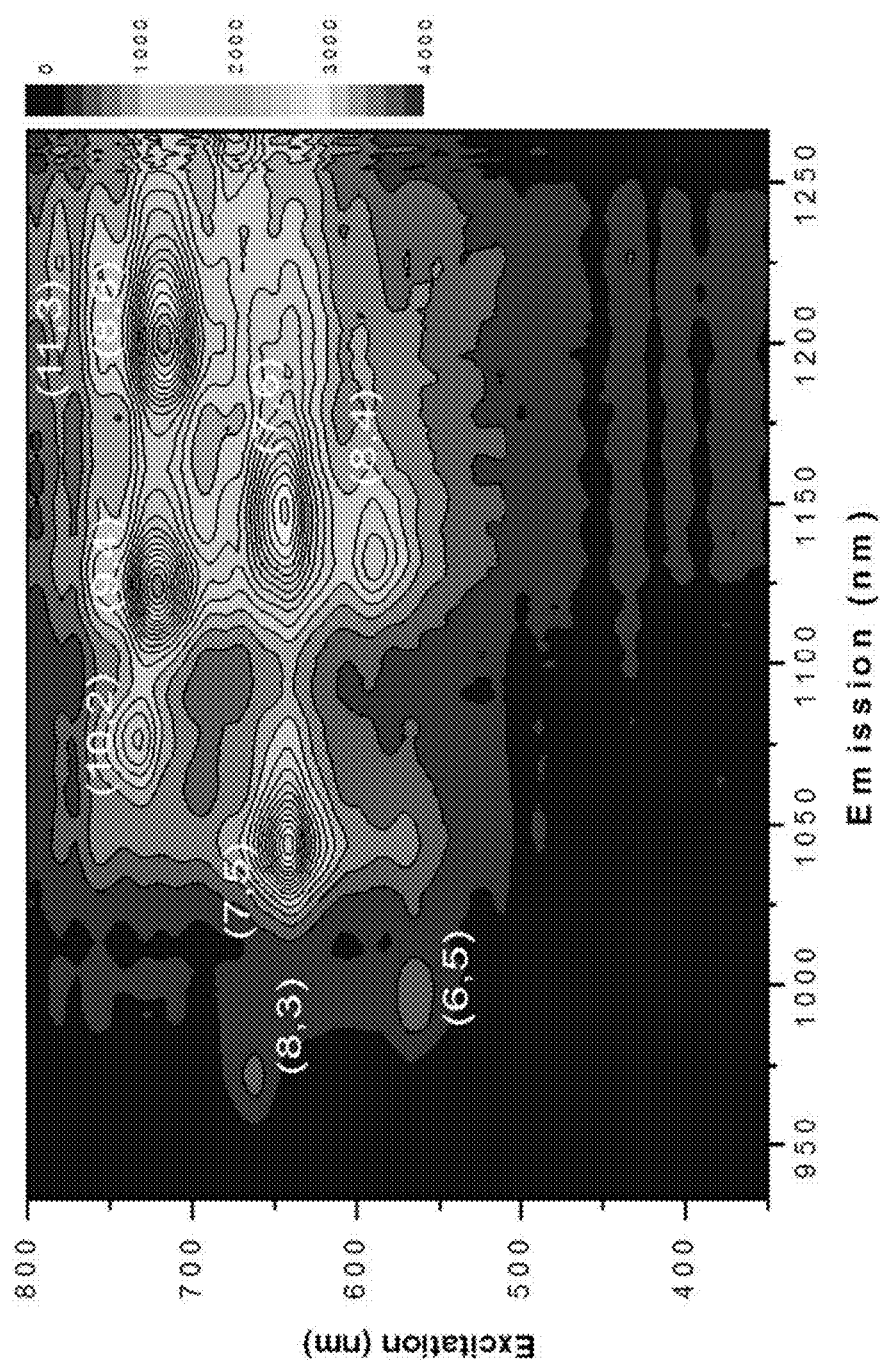
FIG. 14 is a contour plot of fluorescence intensity versus excitation and emission wavelengths for BA-PhO-Dex-SWNT and nanotube assignment.
Figure 15:
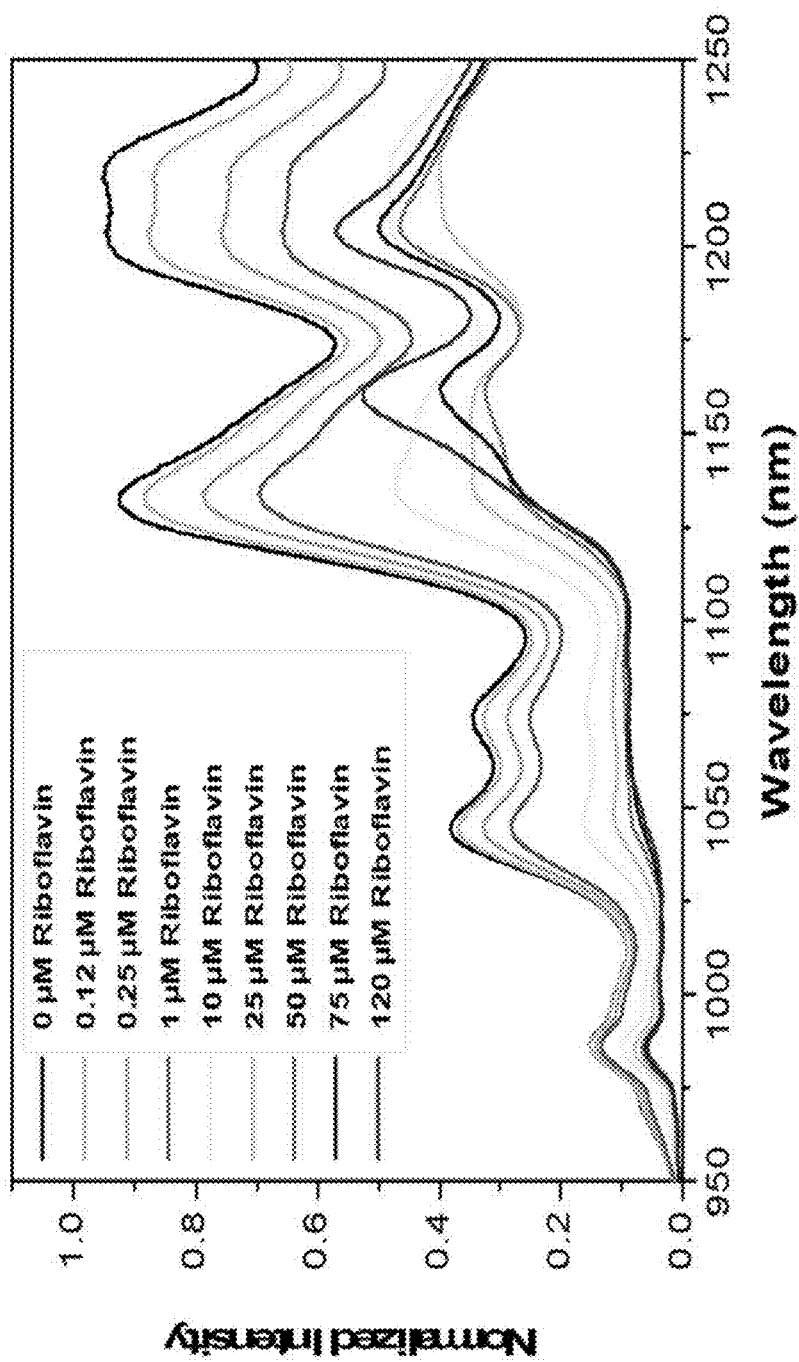
FIG. 15 is a plot of photoluminescence sprectra emitted following exposure to various concentrations of riboflavin.

A method for determining analytes recognized by the selective binding site in the composition can be a high-throughput screening assay (FIG. 13). A method for analyzing samples in a high-throughput system can include providing an array including a plurality of compositions, exposing each composition to at least one sample, monitoring a property of each composition, and determining a presence of an analyte in the sample based on the property. Each composition in the array can include a complex, where the complex can include a nanostructure, and a polymer. The polymer can be adsorbed on the nanostructure and the polymer can be free from selective binding to an analyte in the absence of being adsorbed on the nanostructure. A selective binding site can be associated with the complex.

A well plate array can be used for exposing the composition to an analyte. The composition in different individual wells can include different individual polymers. The composition in different individual wells can include the same polymer. In some embodiments, the composition in different individual wells can be exposed to different individual analytes. In other embodiments, the composition in different individual wells can be exposed to the same analyte.

It can be determined using the methods above that a specific composition can selectively bind to a specific analyte. The specific composition can be used for detecting the analyte in a sample. The specific composition can detect the specific analyte in a sample containing other analytes. The specific composition can be mixed with other compositions. The other compositions can have selective binding for other analytes. The specific composition mixed with other compositions can detect the specific analyte in a sample. The specific composition mixed with other compositions can detect the specific analyte in a sample containing other analytes. In addition, more than one specific composition mixed with other compositions can detect the specific analytes corresponding to the specific analytes in a sample containing other analytes.

For example, composition A can detect analyte A; composition B can detect analyte B; and composition C can detect analyte C. It is possible that composition A can detect analyte A in a mixture including analyte A, analyte B, and analyte C. Furthermore, it is possible that composition A, in a mixture including composition A, composition B and composition C, can detect analyte A. Additionally, it is possible that composition A, in a mixture including composition A, composition B and composition C, can detect analyte A from a sample including analyte A, analyte B and analyte C.

The following examples are representative.

EXAMPLES

Materials:

SWNTs were from the Rice University research reactor run 114 or were purchased from Nano-C. Sodium cholate (SC), sodium dodecyl sulfate (SDS), poly (vinyl alcohol) (PVA, 87-89% hydrolyzed), dextran from *Leuconostoc mesenteroides* (9 kD to 11 kD Mw), 1,2-epoxy-3-phenoxypropane, chloroacetic acid, 3-aminophenylboronic acid, N-(3-dimethyl-aminopropyl)-N'-ethylcarbodiimide hydrochloride (EDC), N-hydroxysuccinimide (NHS), dimethyl sulfoxide (DMSO), 3-aminopropyltriethoxysilane (APTES) and all tested analytes were purchased from Sigma Aldrich and used as received. 1,2-dipalmitoyl-sn-glycero-3-phosphoethanolamine-N-(lauroyl) (PL-DOD) was purchased from Avanti Polar Lipids Inc. Ultra pure nitric oxide (NO, 99.99%) gas was purchased from Airgas. The NO solution was prepared by bubbling pure NO gas through 1X Tris (20 mM, pH 7.3) that had been deoxygenated by bubbling argon through it for two hours. DNA oligonucleotides and peptides were purchased from Integrated DNA Technologies (IDT) and AnaSpec, Inc. respectively, and used as received. Macrophage cell line Raw 264.7, Dulbecco's modified Eagles' medium (DMEM), and Leibovitz's L-15 medium were purchased from American Type Culture Collection (ATCC). Heat-inactivated fetal bovine serum (FBS) and Penicillin-Streptomycin solution containing 10,000 U/ml penicillin-G and 10 mg/ml streptomycin were purchased from Gemini Bio-products. 35 mm cell culturing petri dishes were purchased from MatTek Corporation.

Figure 2:
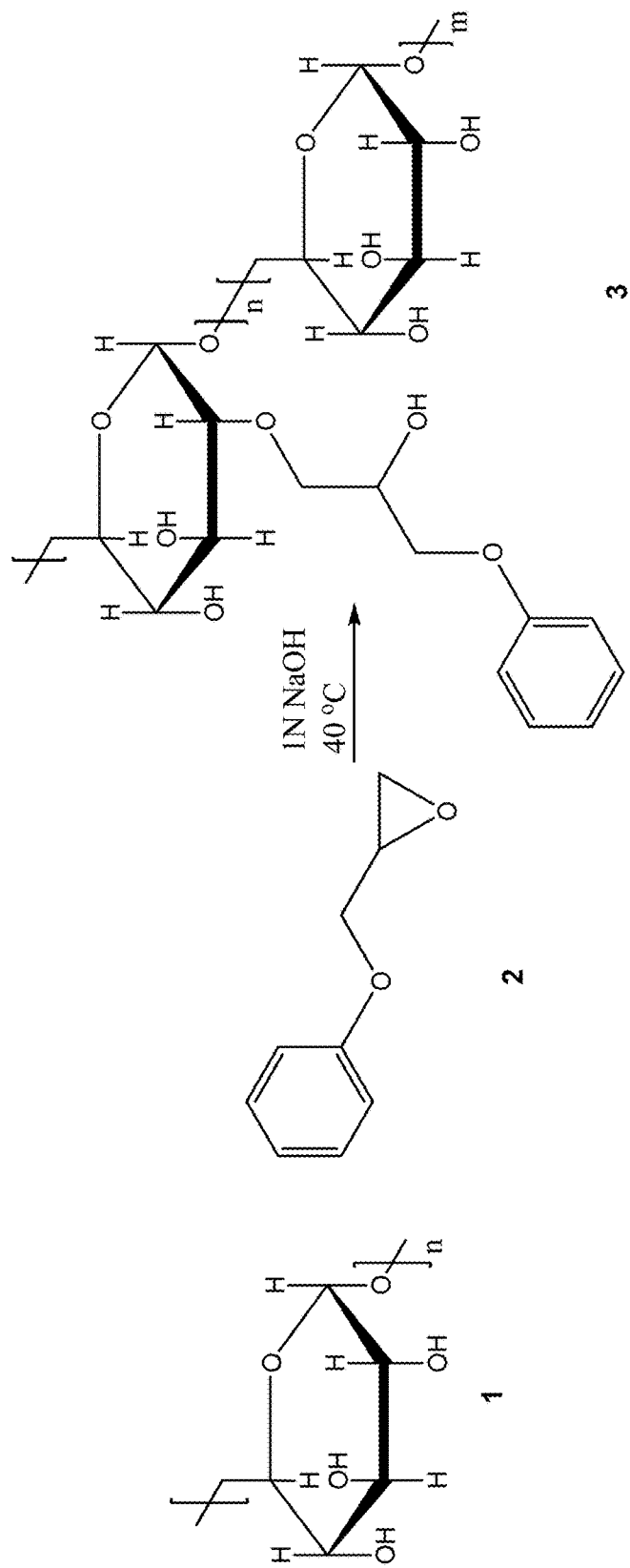
FIG. 2 illustrates the chemical pathway for the synthesis of phenoxy functionalized dextran (PhO-Dex).

Synthesis of PhO-Dex and BA-PhO-Dex:

Synthesis of the phenoxy functionalized dextran 3 was performed as shown in FIG. 2. (Fournier, C., et al., EPR spectroscopy analysis of hydrophobically modified dextran-coated polystyrene. *Journal of Colloid and Interface Science* 198, 27-33 (1998), which is incorporated by reference in its entirety). Dextran 1 (10 g) was dissolved in 90 mL 1N NaOH and pre-heated to 40° C. followed by addition of 1,2-epoxy-3-phenoxypropane 2 (8.3 g). After completion of the reaction, phenoxy functionalized dextran 3 was flocculated by the addition of excess ethanol (EtOH) and collected via filtration. Phenoxy content was determined by measuring UV-vis absorption at 269 nm with a Shimadzu UV-3101 PC UV-VIS-NIR scanning spectrometer. (Fournier, C. et al., (1998)).

Figure 3A:
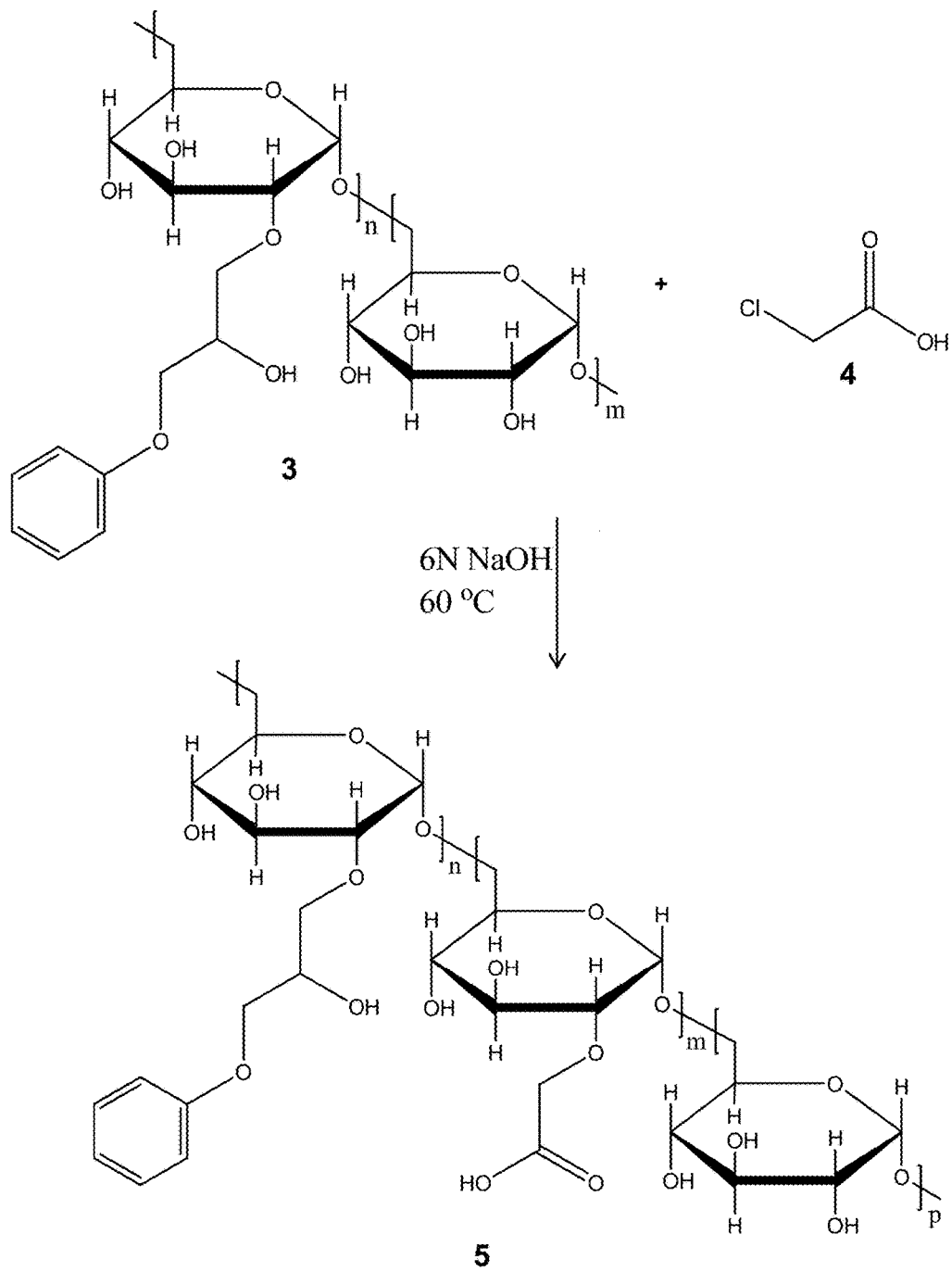
FIG. 3 illustrates the chemical pathway for the synthesis of boronic acid functionalized phenoxy dextran (BA-PhO-Dex).
Figure 3B:
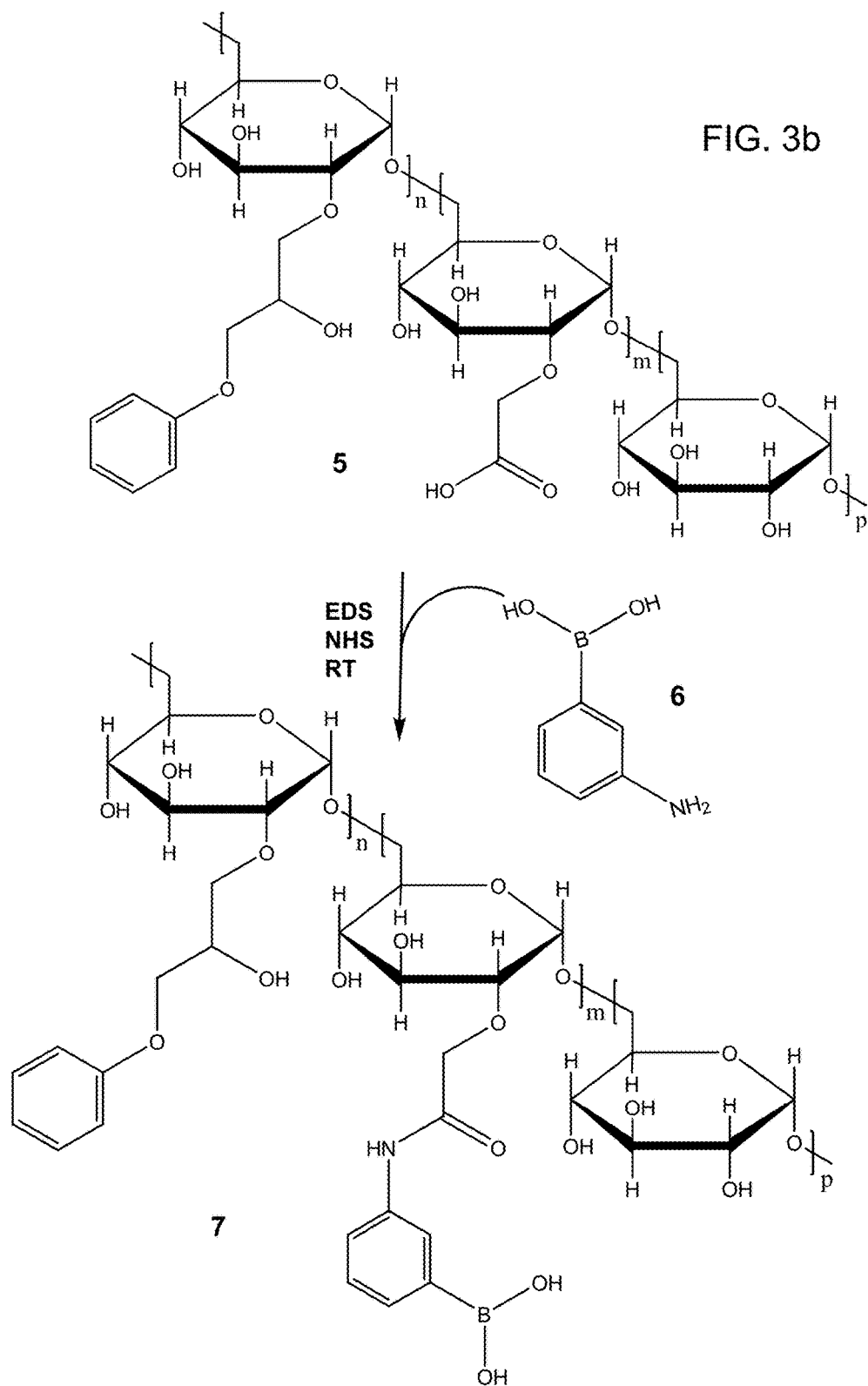
Figure 12:
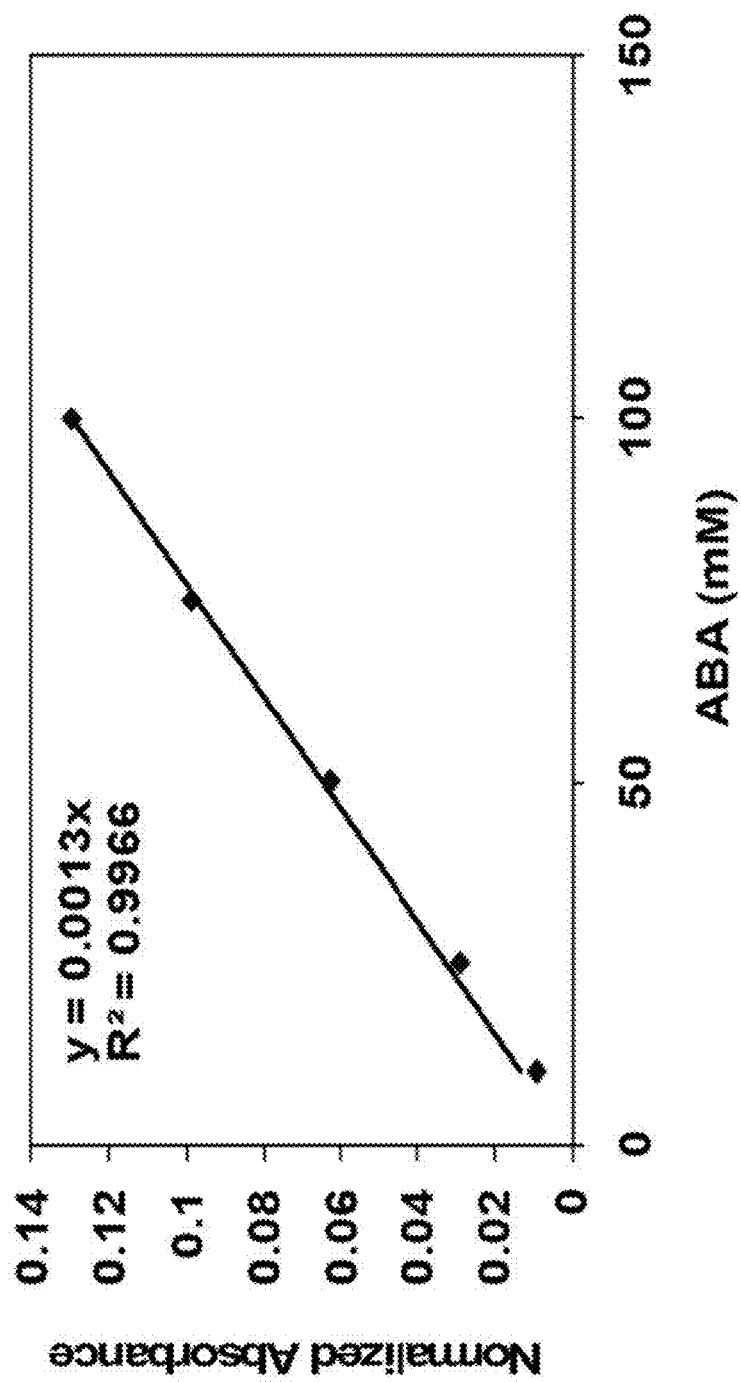
FIG. 12 is a calibration curve for determination of boronic acid composition in the synthesized BA-PhO-Dex polymer.

Synthesis of boronic acid functionalized phenoxy dextran 7 (BA-PhO-Dex) was carried out as shown in FIG. 3. Phenoxy functionalized dextran 3 (10 g) was first dissolved in 82.5 mL 6N NaOH and was heated to 60° C. Chloroacetic acid 4 (20 g) was added and the reaction was allowed to proceed for 1.5 hours. The carboxylmethyl phenoxy dextran 5 (CM-PhO-Dex) was flocculated and washed with excess EtOH, collected via filtration and dried under vacuum. The degree of carboxyl functionalization on carboxylmethyl phenoxy dextran 5 was determined using acidimetric titration with phenolphthalein. Carboxylmethyl phenoxy dextran 5 (1 g) was then dissolved in 30 mL $H_2O$, pH 5, at 25° C. with NHS (0.35 g) and EDC (0.6 g). 3-aminophenylboronic acid 6 (0.47 g) dissolved in 5 mL DMF was added to the solution and the reaction was allowed to proceed for 12 hours. The final boronic acid functionalized phenoxy-dextran 7 (BA-PhO-Dex) was flocculated and washed with excess EtOH, collected via filtration and dried under vacuum. The degree of functionalization with 3-aminophenylboronic acid 6 was determined based on a UV-vis absorption calibration curve at 413 nm (FIG. 12), giving $\epsilon$=0.0013 $mM^{-1}cm^{-1}$.

DNA Oligonucleotide, Peptides, and Polymer Nanotube Suspension:

SWNTs were suspended with both $(AT)_{15}$ and $(GT)_{15}$ oligonucleotides using methods similar to those published. (Heller, D. A. et al., (2006)). SWNTs were suspended with a 30-base (dA-dT) or (dG-dT) sequence of ssDNA in a 2:1 SWNT:DNA mass ratio in 0.1 M NaCl in distilled water. Similarly, SWNTs were suspended with the peptides mastoparan X (INWKGIAAMAKKLL-$NH_2$) and mastoparan 7 (INLKALAALAKALL-$NH_2$) in a 2:1 SWNT:mastoparan mass ratio in 1×Tris. Both samples were sonicated with a 6 mm probe tip (Cole-Parmer) for 10 min at power of 10 watts followed by a 180 minute benchtop centrifugation (Eppendorf Centrifuge 5415D) at 16,100×g. Afterwards the pellet was discarded.

For suspension with other polymer materials, SWNTs were first suspended in a 2 wt % sodium cholate (SC) aqueous solution using previously published methods. (O'Connell, M. J. et al., (2002); Barone, P. W., et al., (2005)). Briefly, 1 mg/mL NanoC SWNTs were added to 40 mL 2 wt % SC in NanoPure $H_2O$ and were sonicated with a 6 mm probe tip at 40% amplitude (~12 W) for 1 hour in an ice bath. The resulting dark black solution was ultracentrifuged in an SW32 Ti rotor (Beckman Coulter) at 153,700 RCF (max) for 4 hours to remove unsuspended SWNT aggregates and catalyst particles. The desired polymer for SWNT suspension was then dissolved, at 1 wt %, in the SC-SWNT and the mixture was placed in a 12-14 kD MWCO dialysis bag and dialyzed against 2 L 1×Tris buffer (20 mM, pH 7.3) for 24 hours to remove free SC and allow the polymer to self-assemble on the nanotube surface. The dialysis buffer was changed after 4 hours to ensure SC removal. The resulting suspensions were clear to the eye and were free of SWNT aggregates, indicating successful suspension. (Barone, P. W., et al., Reversible control of carbon nanotube aggregation for a glucose affinity sensor. ANGEWANDTE CHEMIE 118, 8318 (2006), which is incorporated by reference in its entirety).

Cell Cultures:

Raw 264.7 macrophage cells were cultured in Dulbecco's modified Eagles' medium (DMEM) containing 4.5 g/l glucose and 4 mM L-glutamine and further supplemented with 10% (v/v) heat-inactivated FBS and 1% Penicillin:Streptomycin solution. Cells were maintained at 37° C. in a humidified atmosphere with 5% carbon dioxide. Before the experiment, cells were transferred and grown in a petri dish with Leibovitz's L-15 medium and cultured at 37° C. in a humidified atmosphere. Six hours after re-plating, 0.005 μM of SWNT was added into the culture medium, and the cells were maintained at 37° C. in a humidified atmosphere for 12 hours, which allowed SWNTs to be engulfed into the cells before imaging.

Measurement of SWNT Photoluminescence:

All polymer wrapped SWNT solutions were diluted to a final SWNT concentration of 2 mg/l. The following analytes were initially dissolved in DMSO, including ATP, cAMP, creatinine, D-aspartic acid, glycine, L-citrulline, L-histidine, quinine, sodium pyruvate. All other analytes were dissolved in 1×Tris (20 mM, pH 7.3). Analyte solutions were added to the SWNT, such that the final DMSO concentration was 1 volume %, the mixture was incubated for 1 hour and the resulting SWNT photoluminescence was measured with a home-built near infrared (nIR) fluorescence microscope. A Zeiss AxioVision inverted microscope was coupled to a Princeton Instruments InGaAs OMA V array detector through a PI Acton SP2500 spectrometer. Sample excitation was from a 785 nm photodiode laser, 450 mW at the source and 150 mW at the sample.

Deconvolution of SWNT Photoluminescence Spectra:

The fluorescence spectra were fitted using a sum of N=9 Lorentzian lineshapes (8 nanotube peaks and 1 G-prime peak). The fluorescence intensity at any energy, E, is a sum over the contributions of all the species present in solution:

$$I(E) = \sum_{i=1}^{N} \frac{C_i}{2\pi} \frac{\Gamma_i}{(E - E_{0,i})^2 + \Gamma_i^2/4}$$

The parameters to be estimated for the Lorentzian profile of the $i^{th}$ entity have been outlined below.

$C_i$—area under the peak
$\Gamma_i$—full width at half maximum (FWHM, meV)
$E_{0,i}$—peak center in terms of energy (meV)

Initial guesses for the peak areas were calculated from the control spectrum. The area under the $i^{th}$ peak was expressed as a fraction of the total area under the spectrum. This fraction was determined from the intensity of the peak in question. The initial guesses for the FWHM of different nanotubes were obtained either from 2D excitation-emission profile or scaled according to their diameters to ensure a good fit. (Bachilo, S. et al., Structure-assigned optical spectra of single-walled carbon nanotubes. *Science* 298, 2361 (2002); Inoue, T., et al., Diameter dependence of exciton-phonon interaction in individual single-walled carbon nanotubes studied by microphotoluminescence spectroscopy. *Physical Review B* 73, 233401 (2006), which are incorporated by reference in their entirety). The FWHM and peak center for the G-prime peak were kept constant (11 meV and 1258.72 meV, respectively) and only its peak area was floated. In all, 31 parameters were used to fit a single fluorescence spectrum. Each $\Gamma_i$ ($E_{0,i}$) was constrained within a 10 meV (50 meV) window to maintain the physical validity of the fit. For responses such that the degree of quenching was over 50%, the shifting response was set to zero due to the difficulty in distinguishing between actual shifting and relative intensity change of different species. Representative spectra for PVA, PL-DOD-SWNT, BA-PhO, PhO, $AT_{15}$, $GT_{15}$, MastX, Mast7, SC, SDS-SWNT are shown in FIGS. 21-57.

Figure 9:
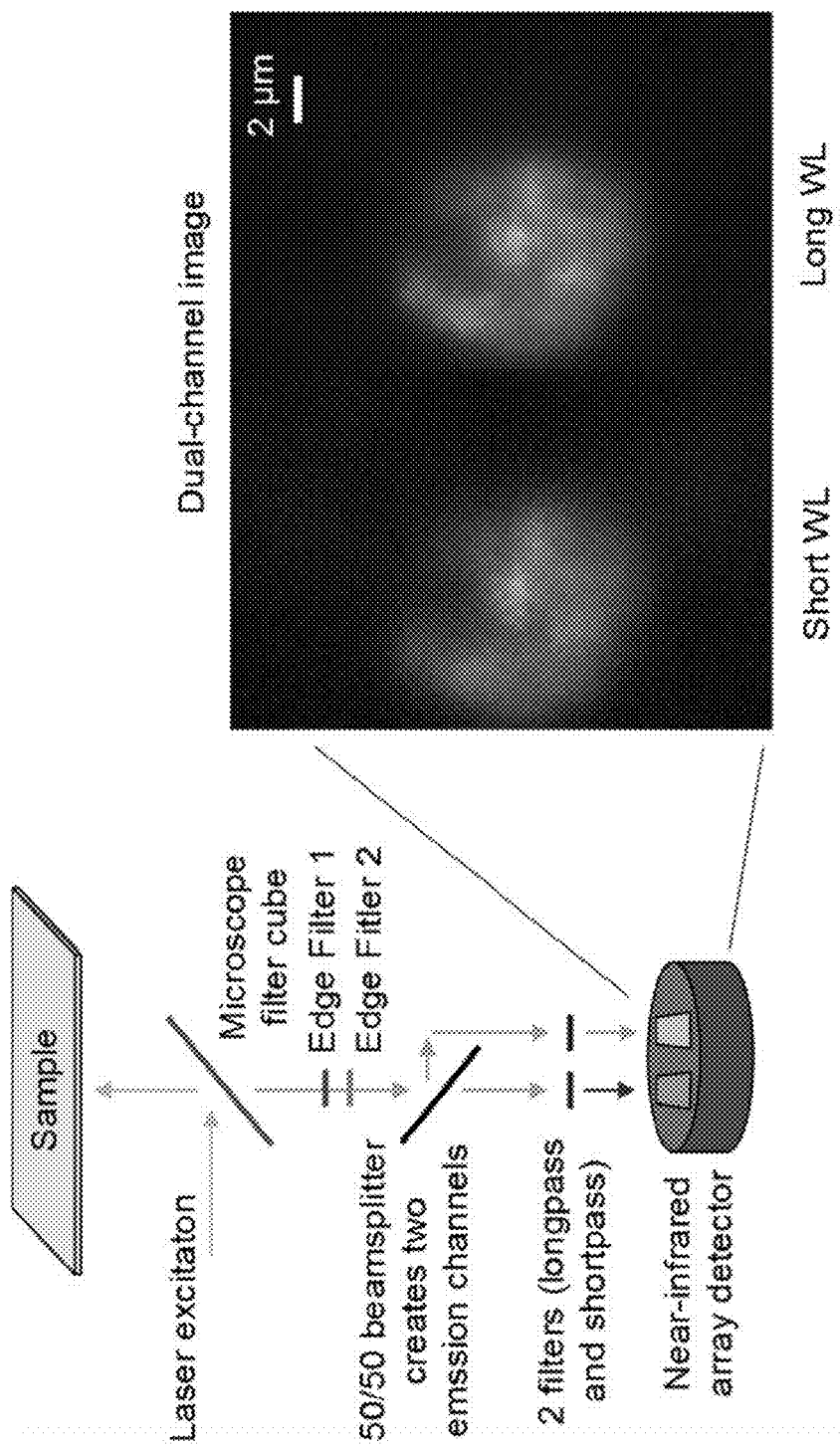
FIG. 9 illustrates the dual channel microscope scheme.

Dual-Channel Microscope and Fluorescence Detection:

A dual-channel microscope for imaging spectral shifts of nanotube photoluminescence was constructed (FIG. 9). The home-made microscope allowed spectroscopic information to be elucidated by splitting the image into two channels, which were adjacent in wavelength. Exposed to 658 nm laser (LDM-OPT-A6-13, Newport Corp) excitation, three SWNT species including (8,3), (7,5) and (7,6) showed bright photoluminescence. The emission light from the sample was split into two beams. The light from both beams was treated with filters to spectroscopically isolate one emission peak, and then to permitted only half of the peak's emission to appear in each channel. One channel (FIG. 9, right) on the same near infrared detector array (InGaAs OMA V array detector through a PI Acton SP2150i spectrometer) showed the long wavelength half of the peak, and the other (FIG. 9, left) showed the short wavelength half. The filters used were designed to measure the (7,6) nanotube, which has the emission maximum at 1147 nm before exposure to any analytes. The 50% cut-off/cut-on of the two edge filters used were 1100 and 1180 nm, respectively, to band the (7,6) emission. An 1140 nm longpass and an 1140 nm shortpass filter were placed in the emission beam before splitting to isolate the (7,6) peak.

After being incubated with SWNT for 12 hours, the cells were ready for fluorescence imaging. The dual-channel microscope mentioned above was used to monitor in real-time the change of nIR photoluminescence of BA-PhO-Dex-SWNT inside the macrophage (FIG. 11a and FIG. 9), in response to extracellularly-added riboflavin. Real time movies were acquired using the WinSpec data acquisition program (Princeton Instruments) for 1 hour. Visible images were acquired using an attached CCD camera (Carl Zeiss, ZxioCam MRm).

Dual-Channel Microscope Image Processing:

Each frame in the movie was first de-noised by median filtering with the kernel size set to 3×3. The quantitative analysis was then performed, where total photoluminescence quenching response was represented by normalized intensity and shifting response of the emission maximum was represented by the normalized intensity of the right (1140-1180 nm) channel divided by the normalized intensity of the left channel (1100-1140 nm). To visualize the results of analysis, a binary mask was generated by setting a threshold for the initial frame, in which the pixels whose intensity value was above an empirically determined value were considered within the region of interest. The values of the pixels outside this region were set to zero in the visualized results.

Microscopy and Data Analysis for Single Molecule Detection:

$AT_{15}$-SWNTs were deposited onto a Petri dish through 3-aminopropyltriethoxysilane (APTES) (FIG. 18). The $AT_{15}$-SWNT and APTES construct was stable at physiological pH. This may have been due to the charge-charge interaction. The microscope technique was similar to that reported in the literature (FIG. 18). (Jin, H., et al., Stochastic analysis of stepwise fluorescence quenching reactions on single-walled carbon nanotubes: single molecule sensors. *Nano letters* 8, 4299-4304 (2008), which is incorporated by reference in its entirety). Samples were excited by a 658 nm laser (LDM-OPT-A6-13, Newport Corp) at 35 mW. The photoluminescence of $AT_{15}$-SWNT was imaged and monitored in real time through a 100×TIRF objective for hours using an inverted microscope (Carl Zeiss, Axiovert 200), with a 2D InGaAs array (Princeton Instruments OMA 2D) attached. Movies were acquired at 0.2 s/frame using the WinSpec data acquisition program (Princeton Instruments). Before the experiment, a control movie (same movie length as the experiment movie) was taken to ensure a stable baseline. In the experiment, nitric oxide (200 nM) in Tris (1×, pH 7.3) buffer was injected through a fine hole, allowing minimal exposure to air.

Figure 20:
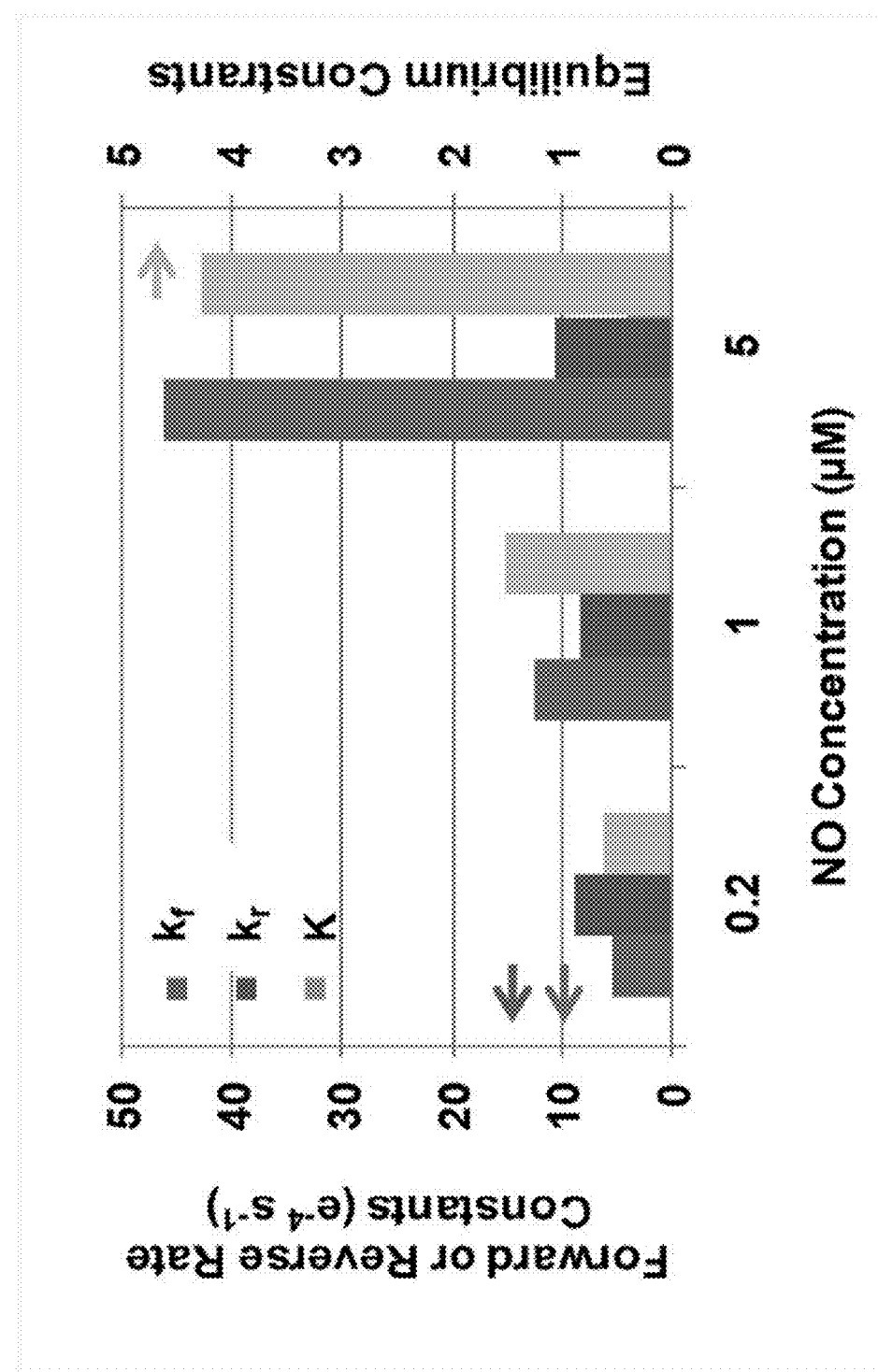
FIG. 20 is a nitric oxide concentration calibration curve.
Figure 21A:
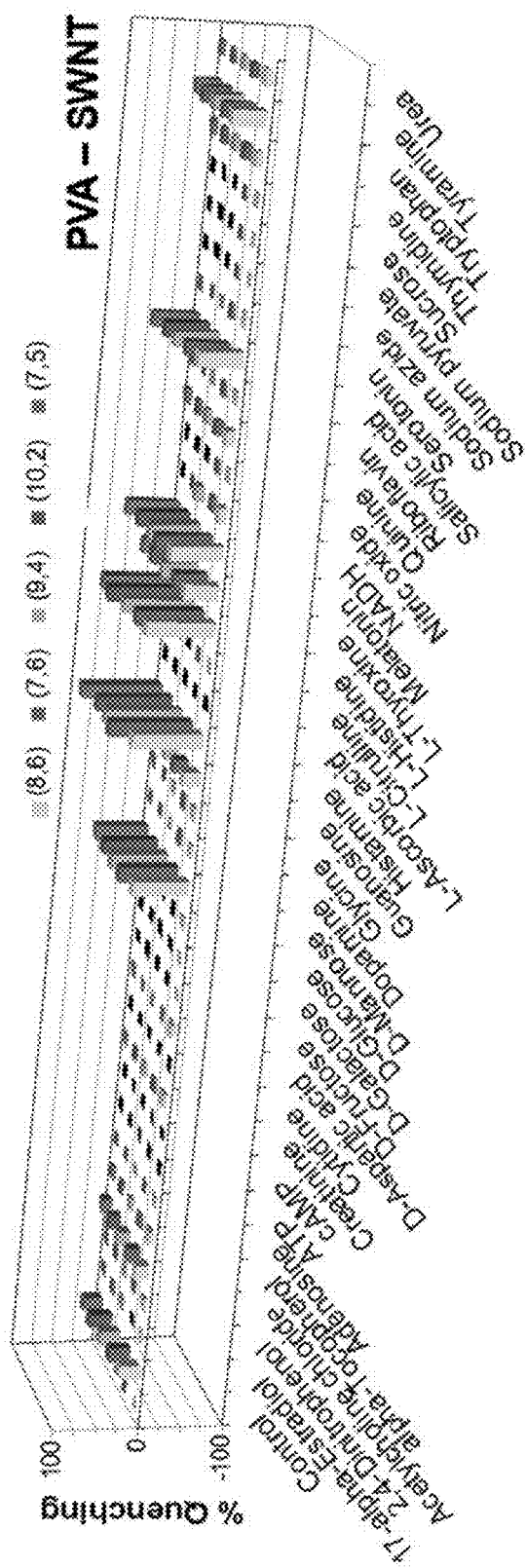
FIG. 21 includes two plots of the nanotube specific fluorescence response of PVA-SWNTs to different analytes.
Figure 21B:
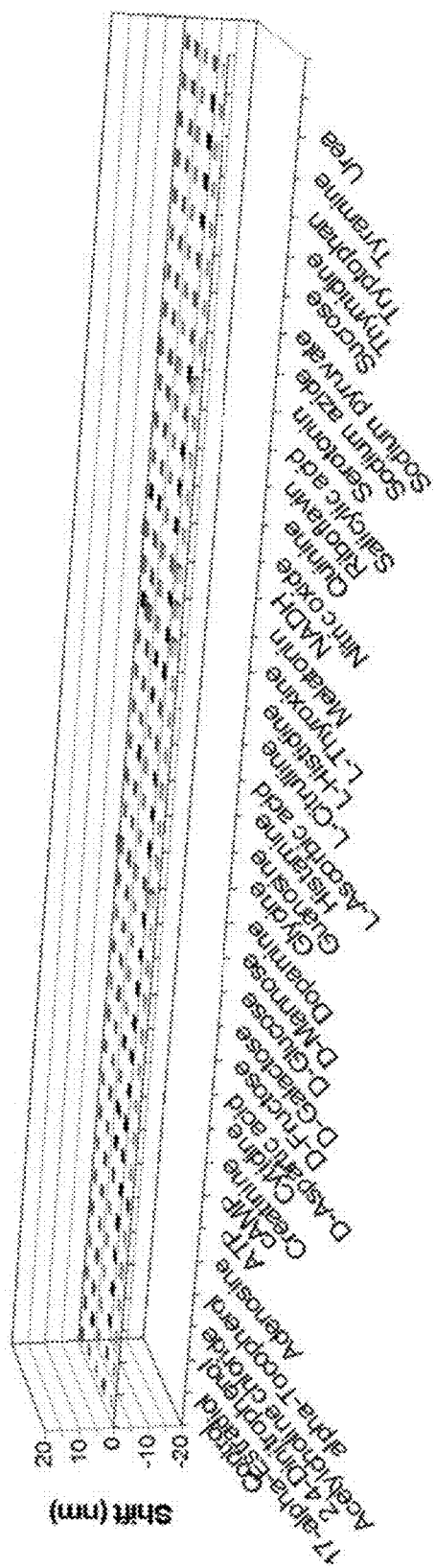
Figure 22A:
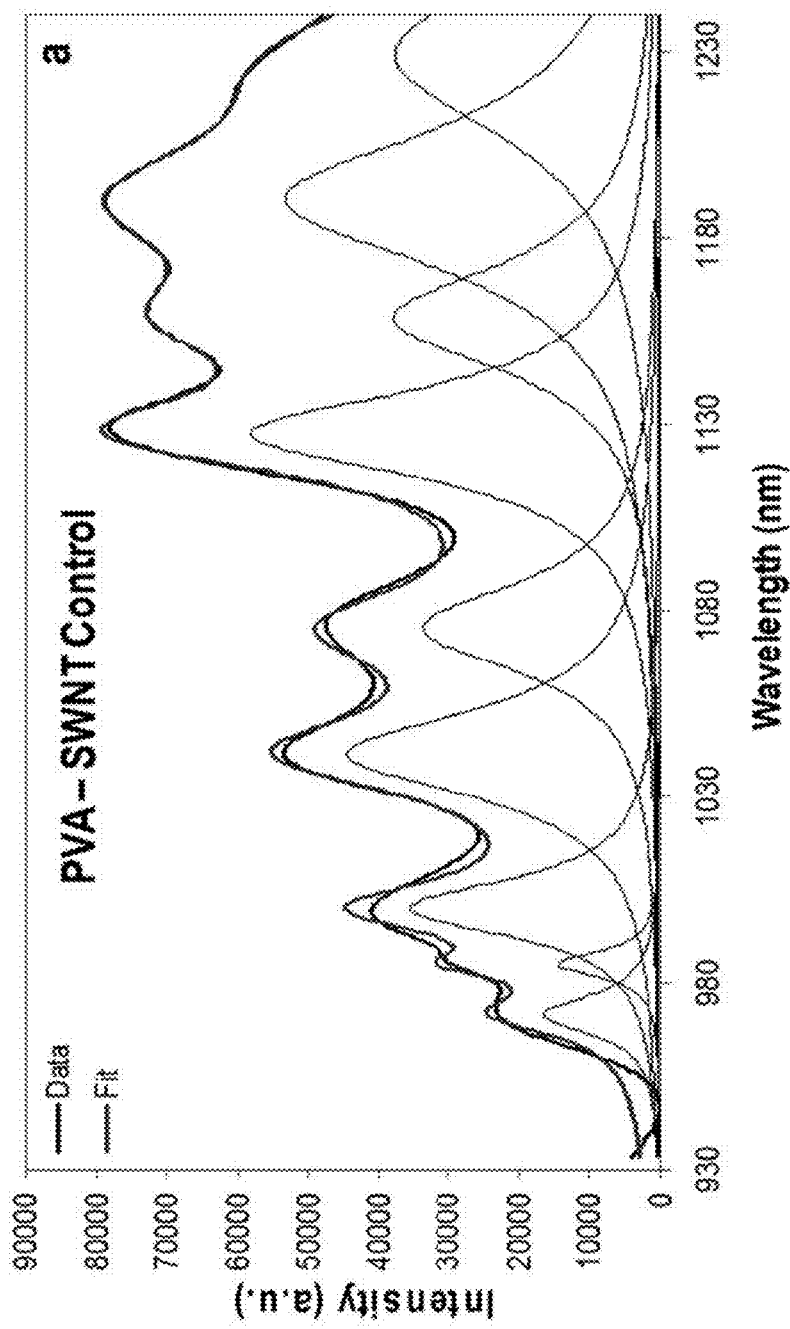
FIGS. 22-24 are deconvoluted spectra of fluorescence response of each nanotube species in PVA-SWNT to different analytes.
Figure 22B:
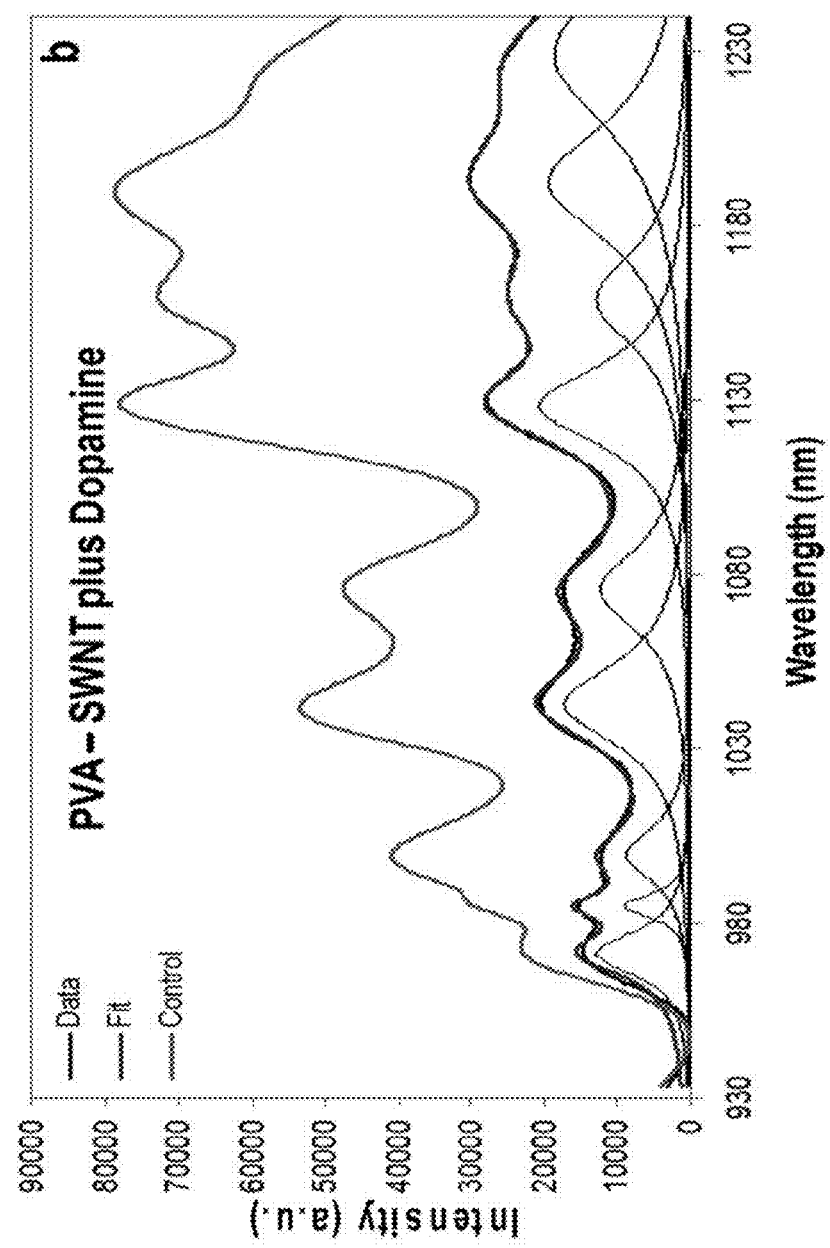
Figure 22C:
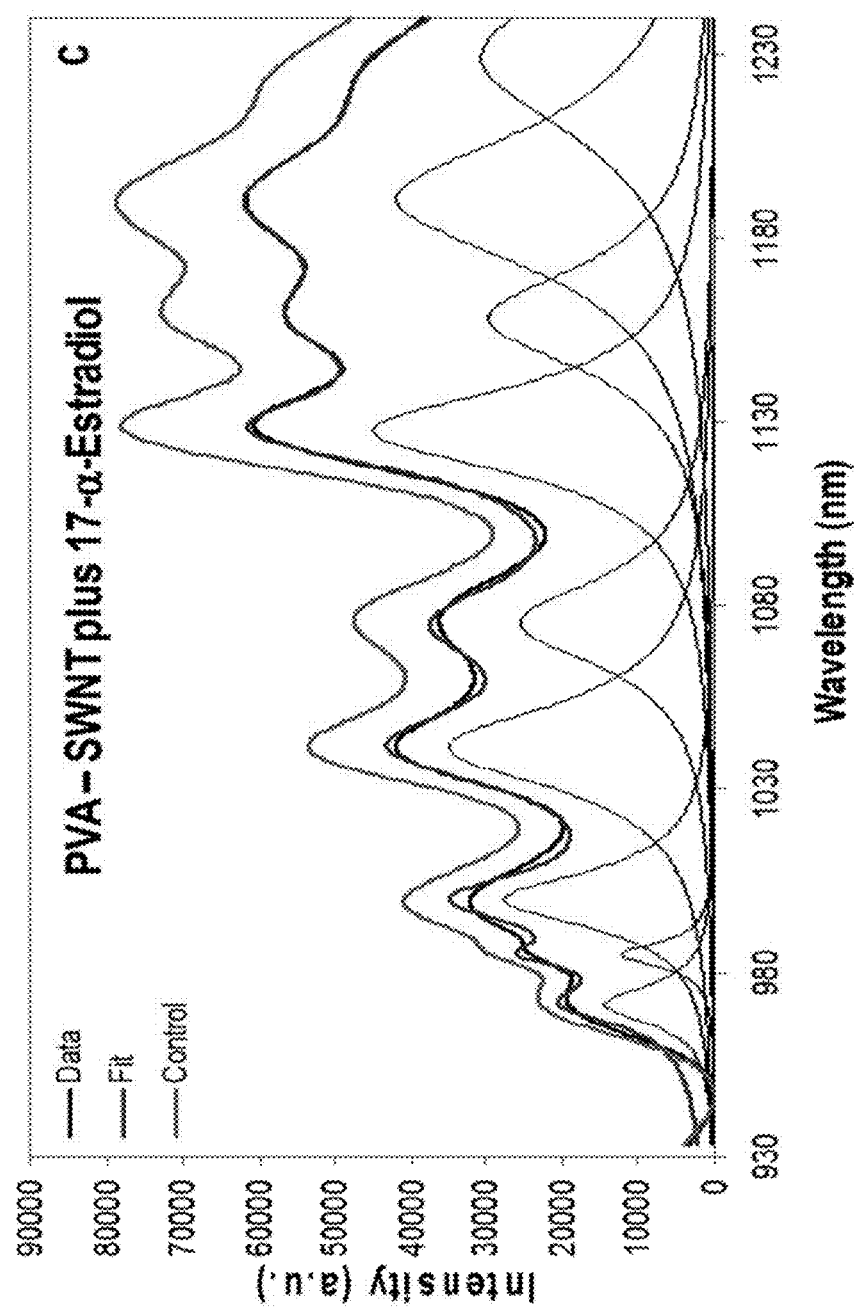
Figure 23A:
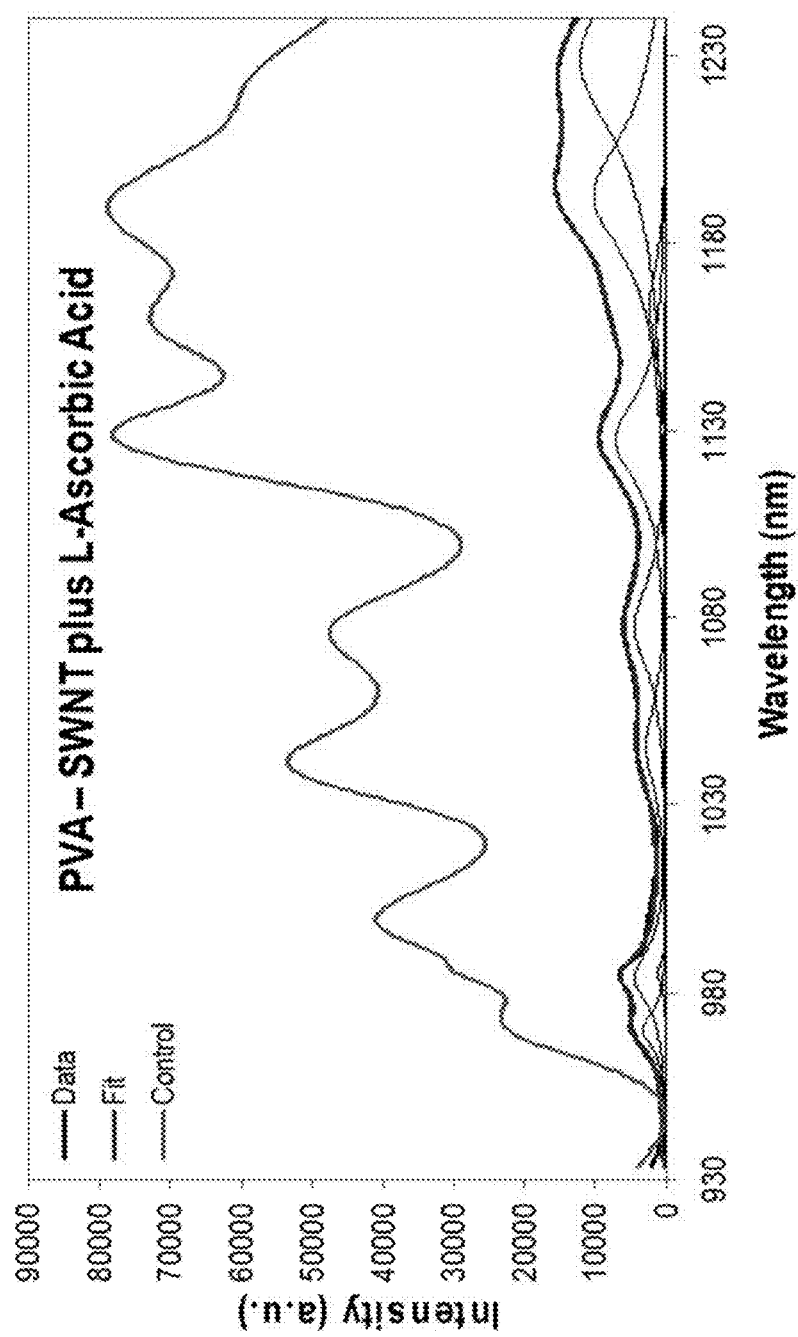
Figure 23B:
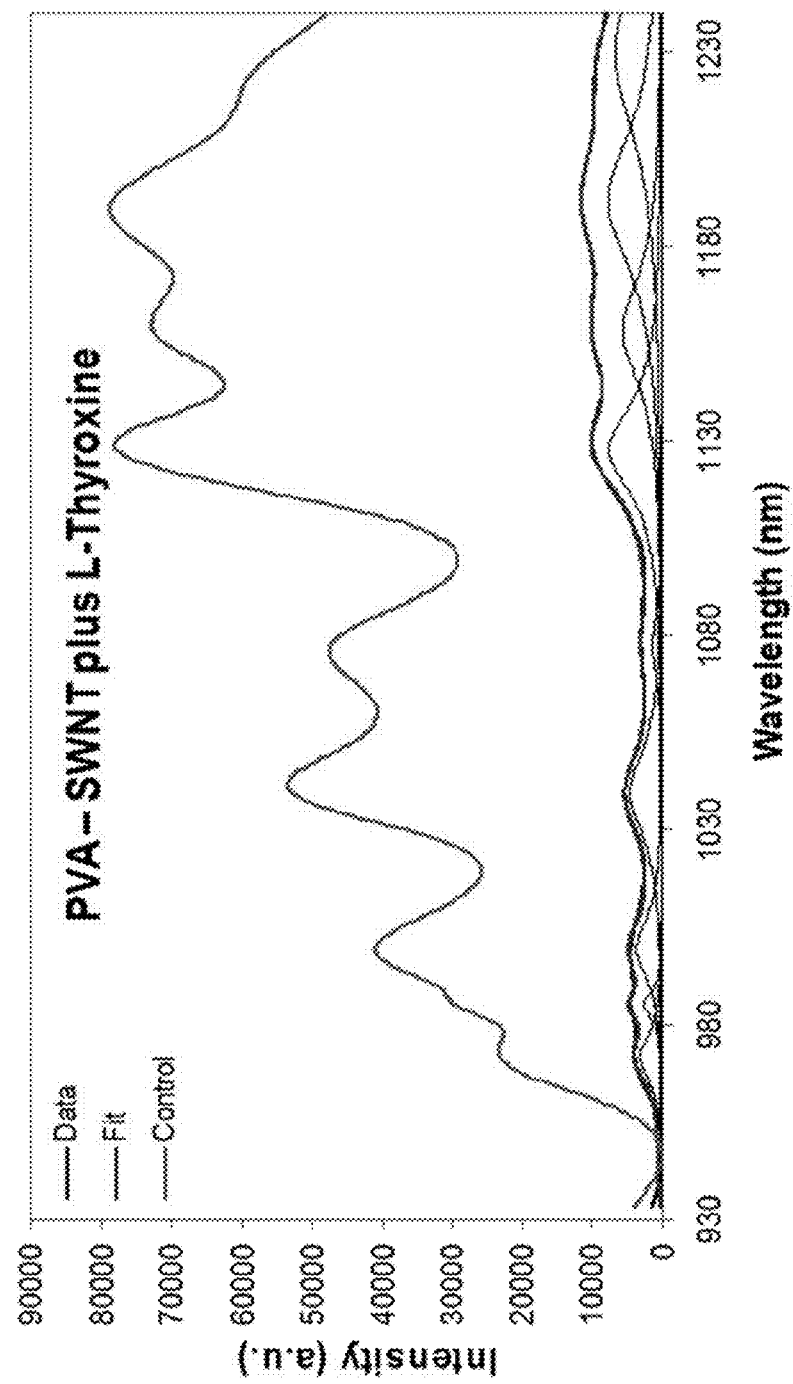
Figure 23C:
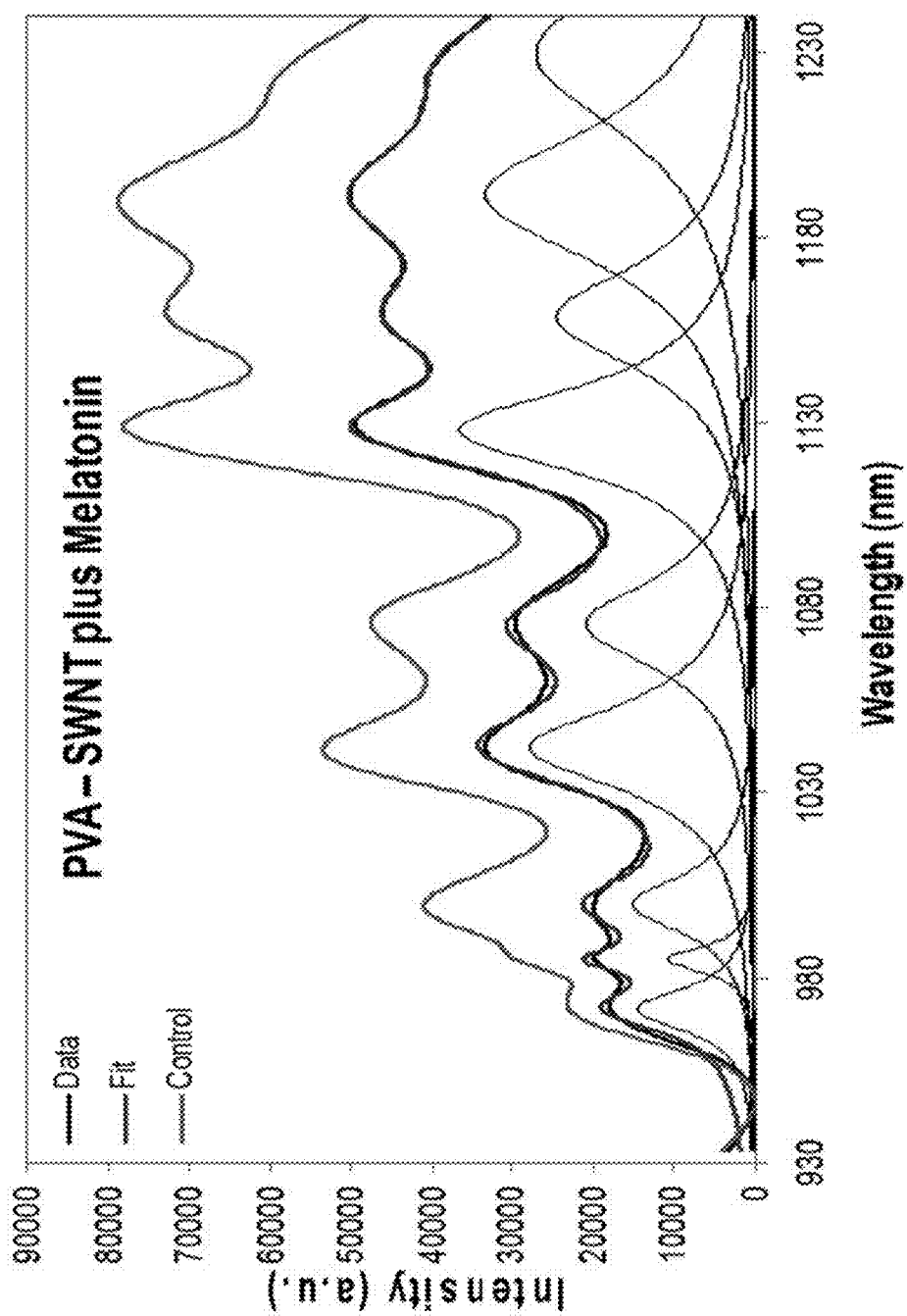
Figure 24A:
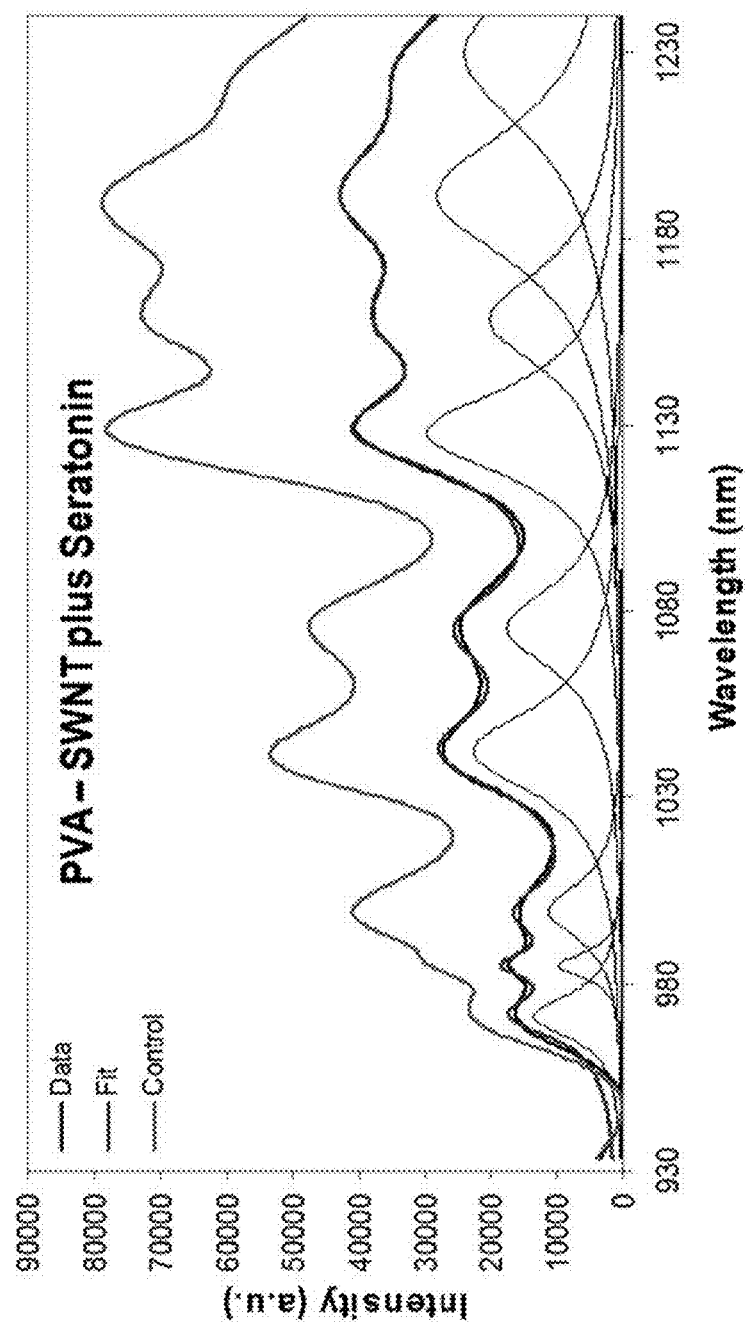
Figure 24B:
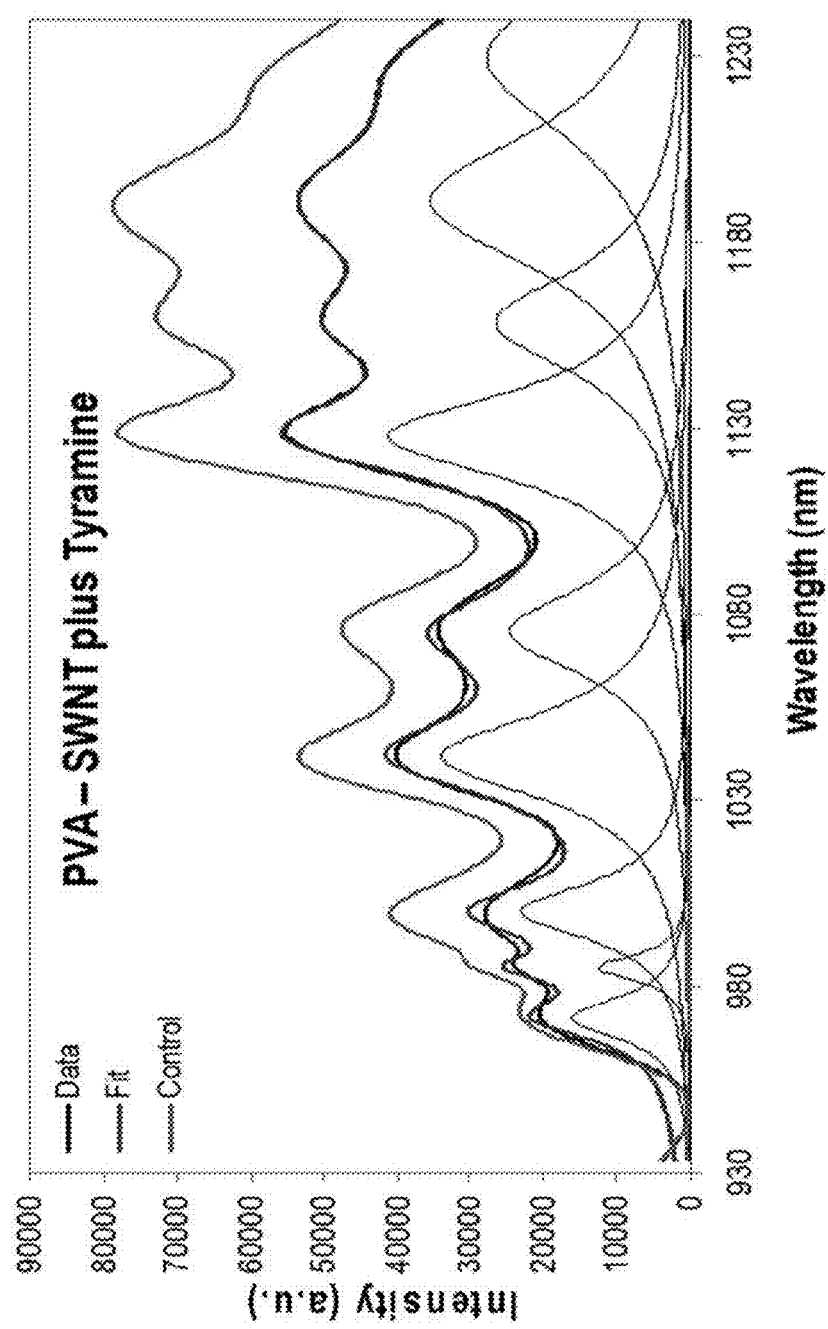
Figure 25A:
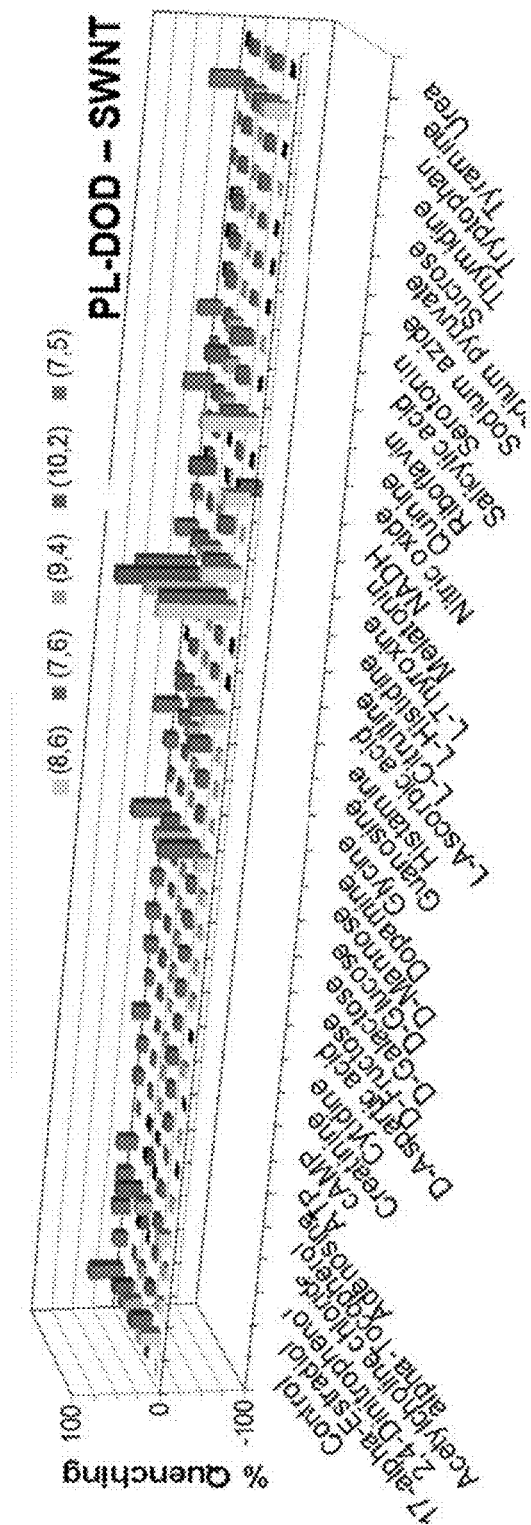
FIG. 25 includes two plots of the nanotube specific fluorescence response of PL-DOD-SWNTs to different analytes.
Figure 25B:
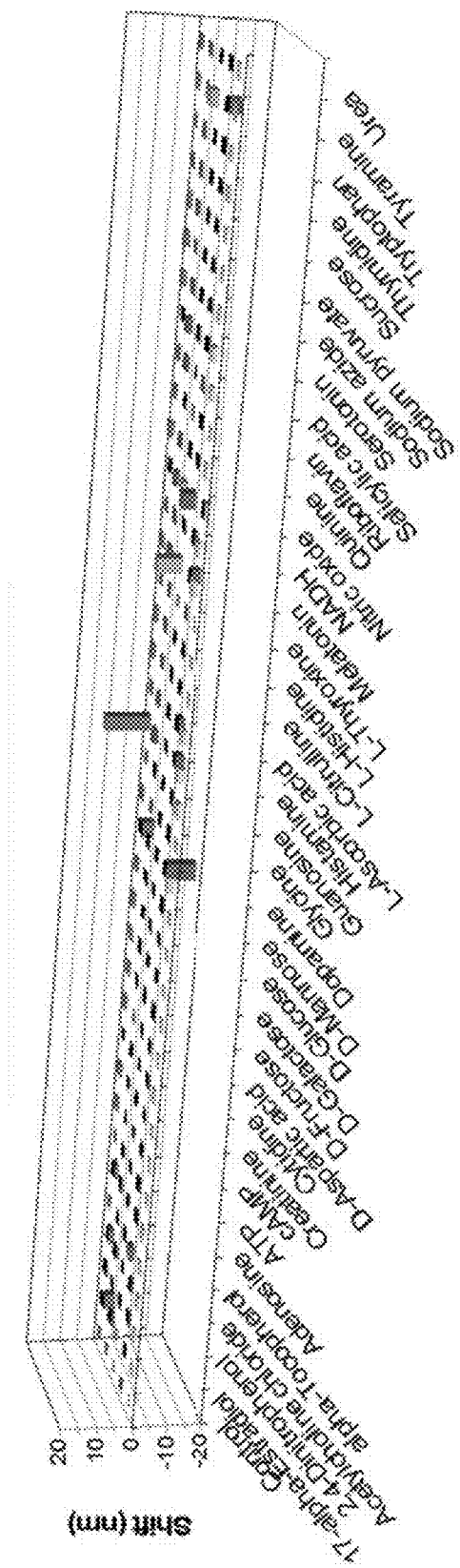
Figure 26A:
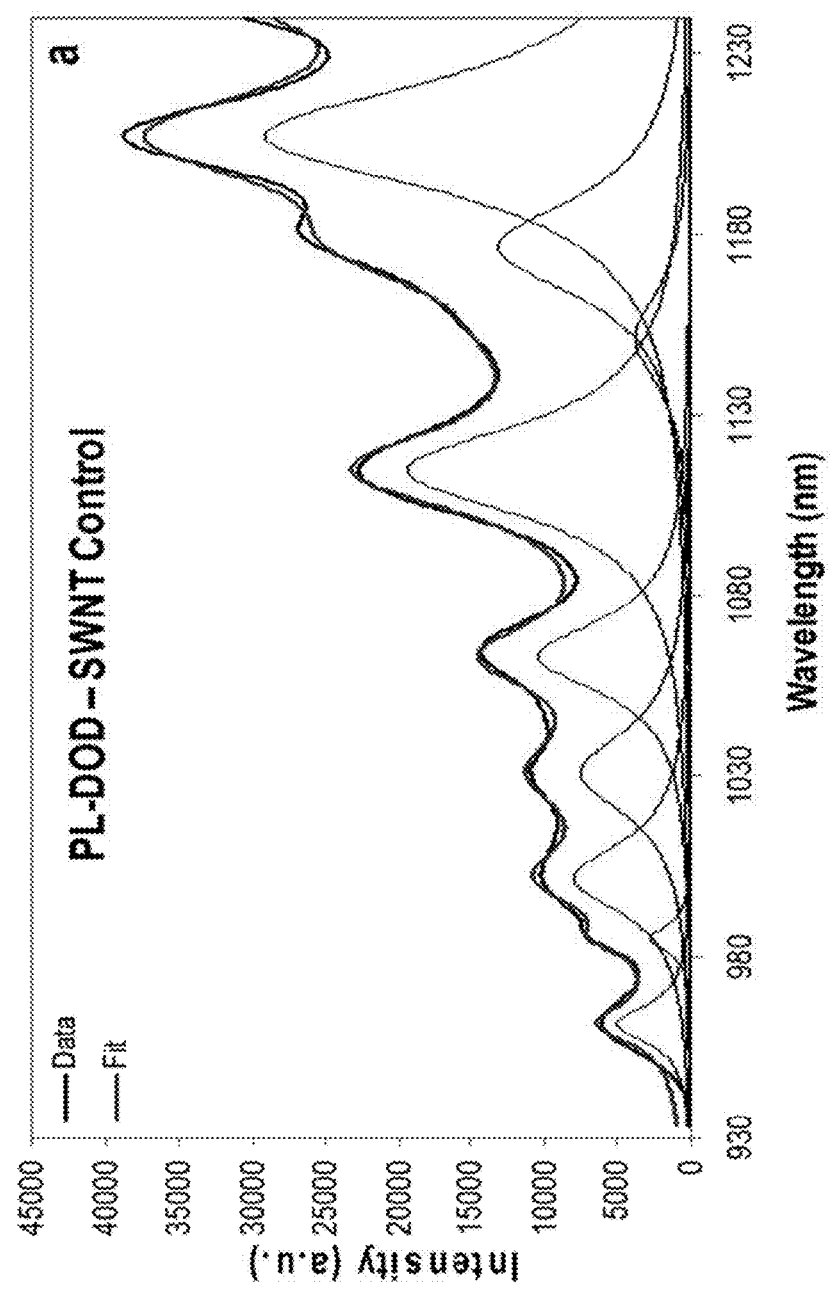
FIGS. 26-27 are deconvoluted spectra of fluorescence response of each nanotube species in PL-DOD-SWNT to different analytes.
Figure 26B:
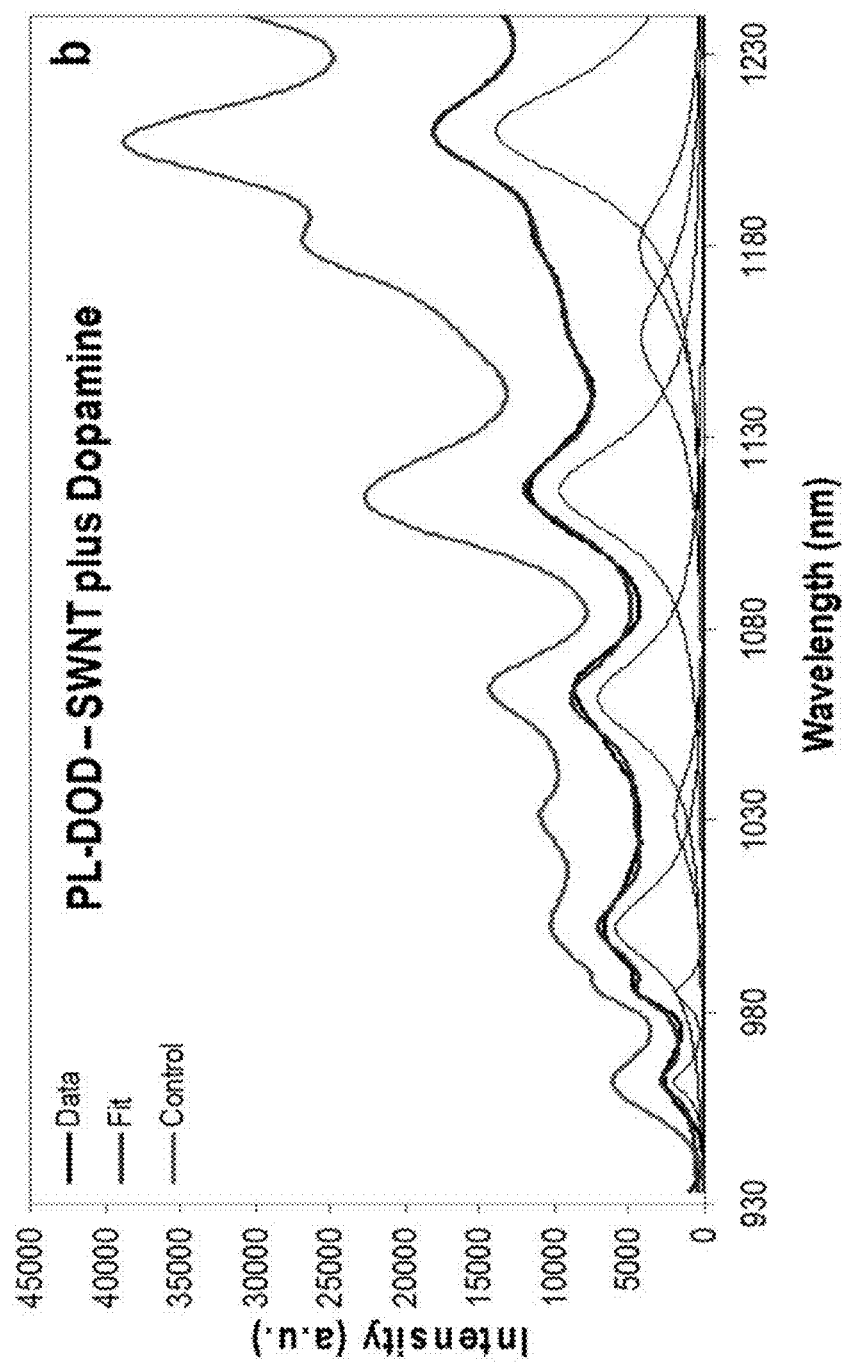
Figure 26C:
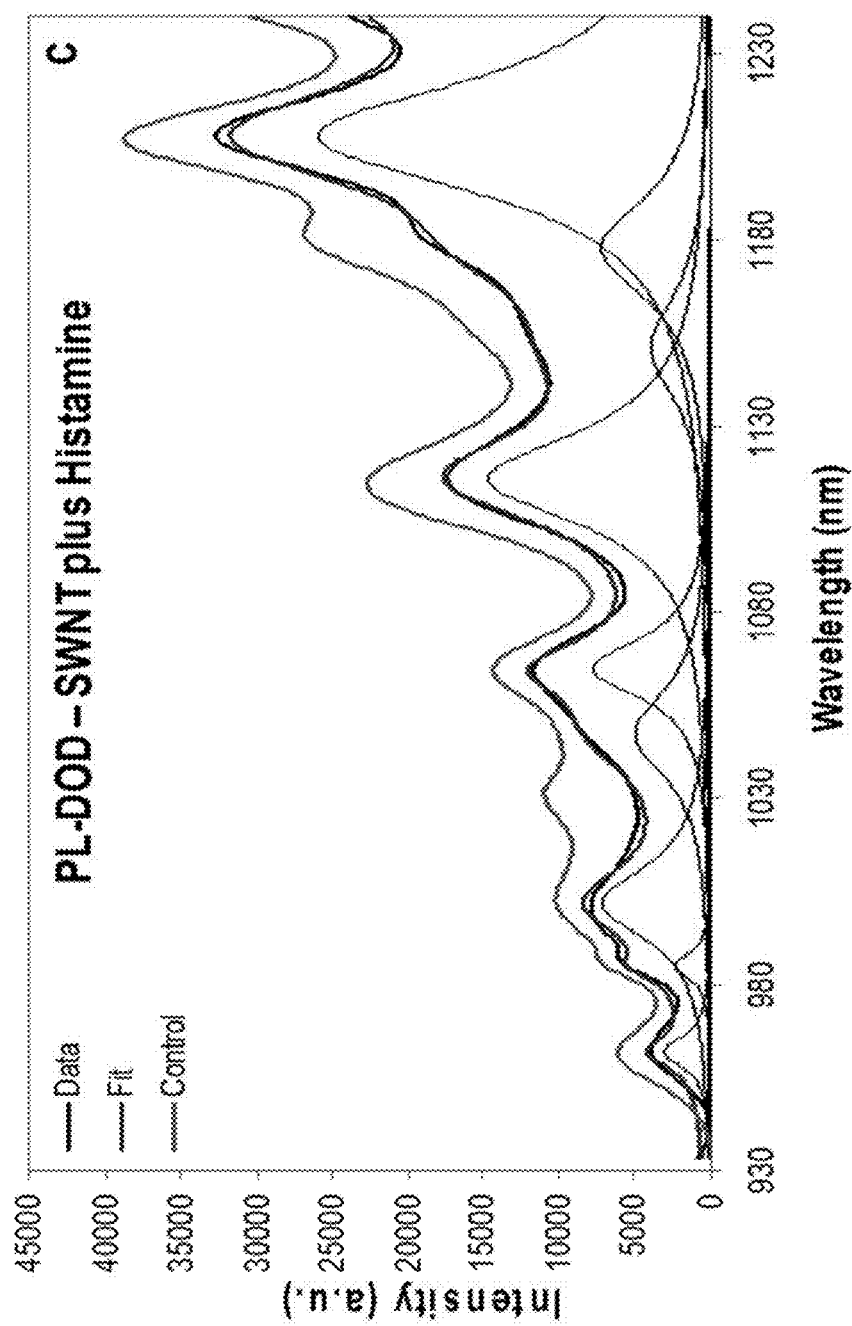
Figure 27A:
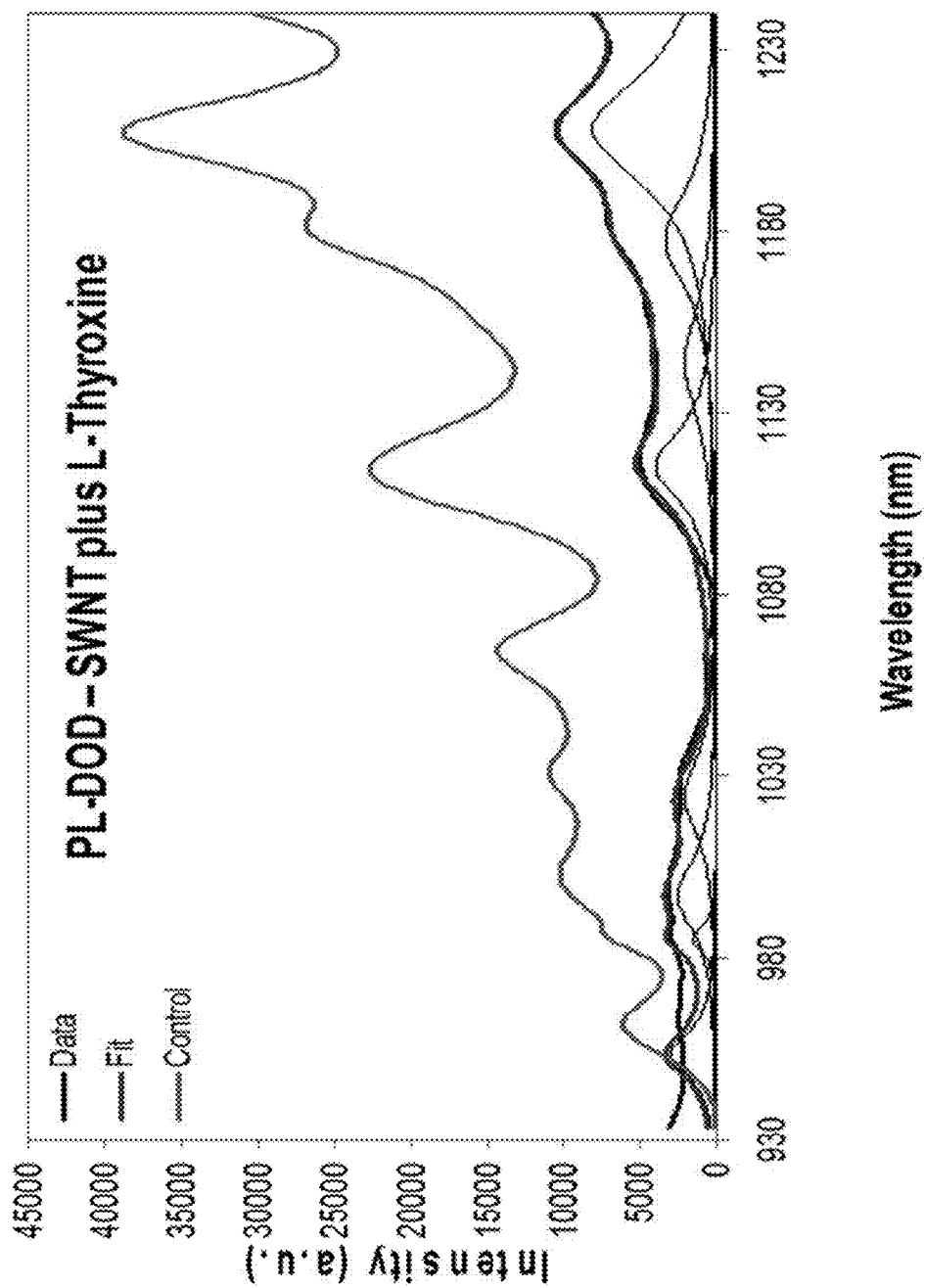
Figure 27B:
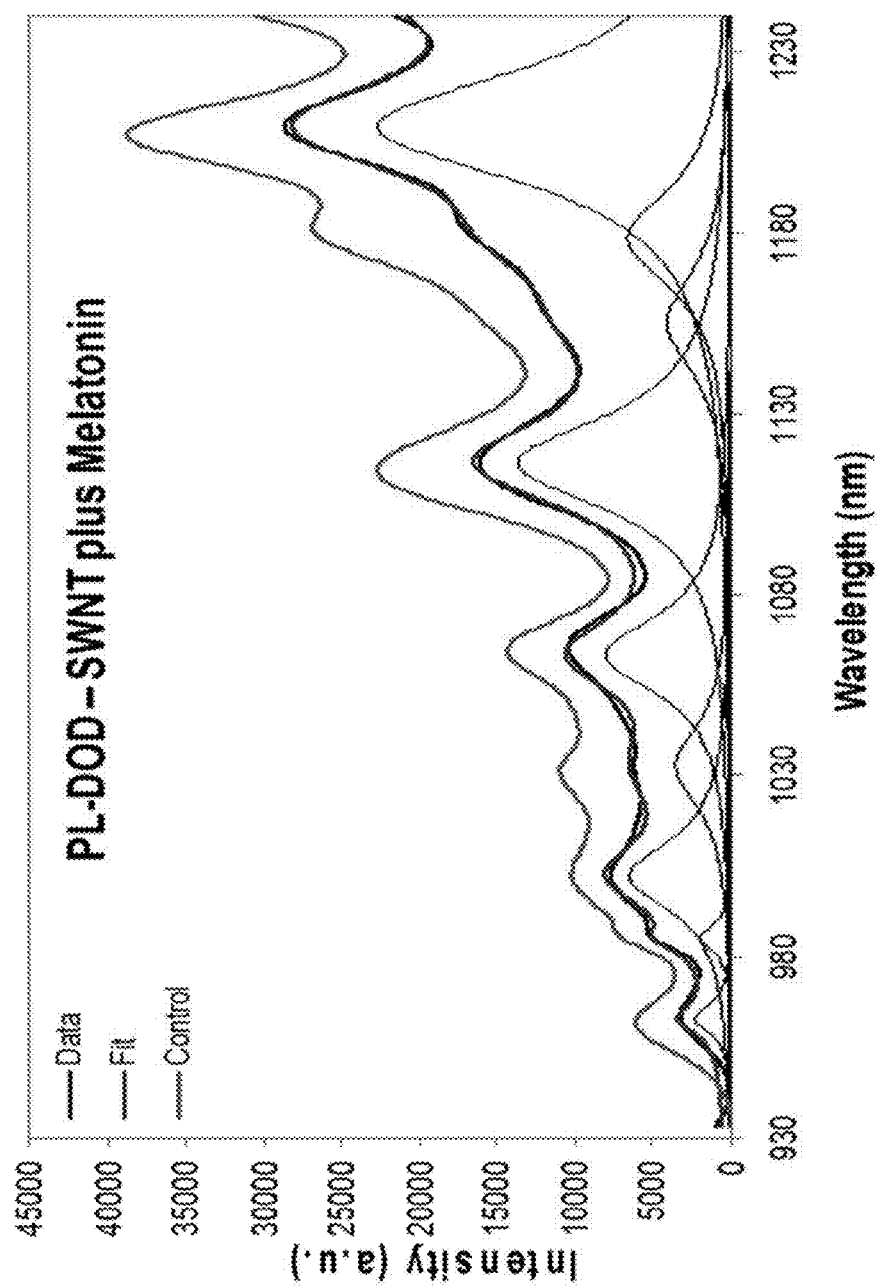
Figure 28A:
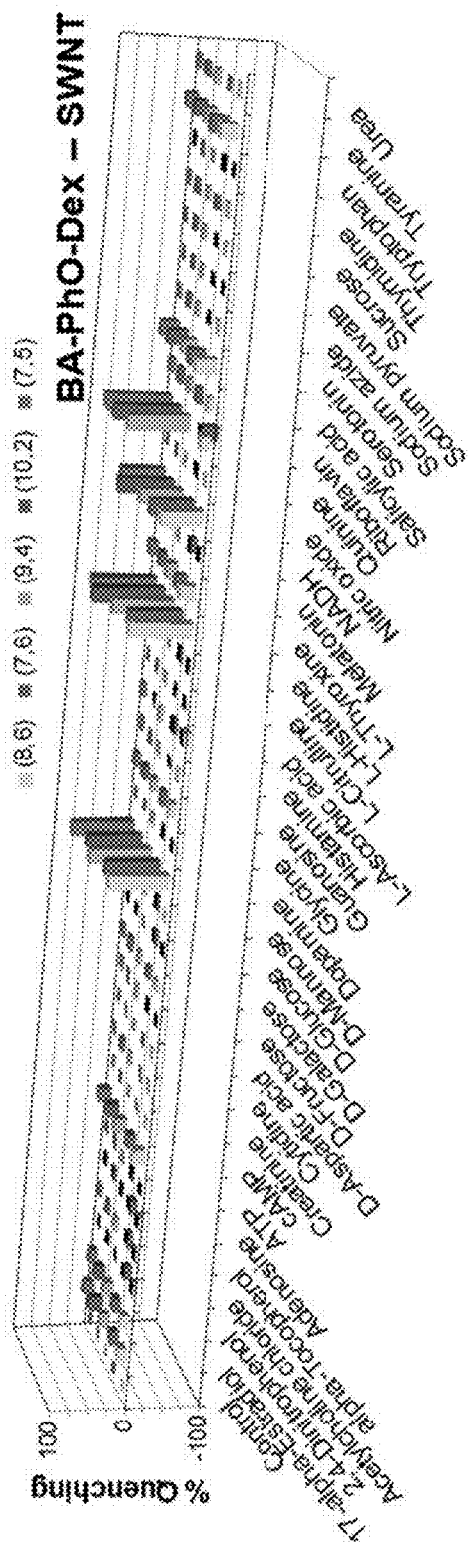
FIG. 28 includes two plots of the nanotube specific fluorescence response of BA-PhO-Dex-SWNT to different analytes.
Figure 28B:
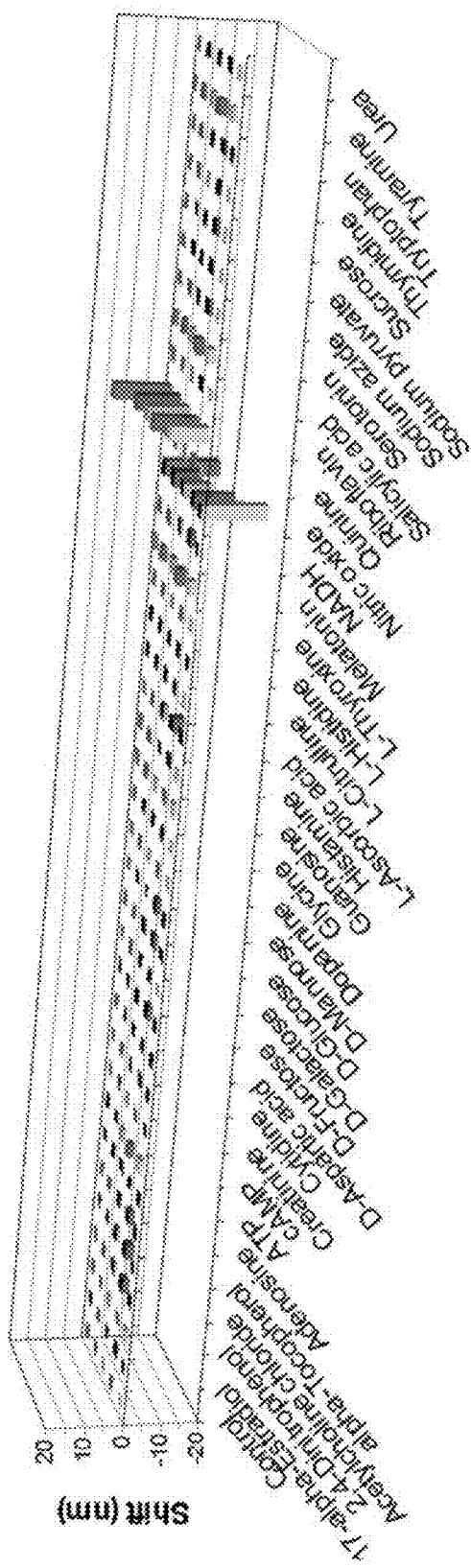
Figure 29A:
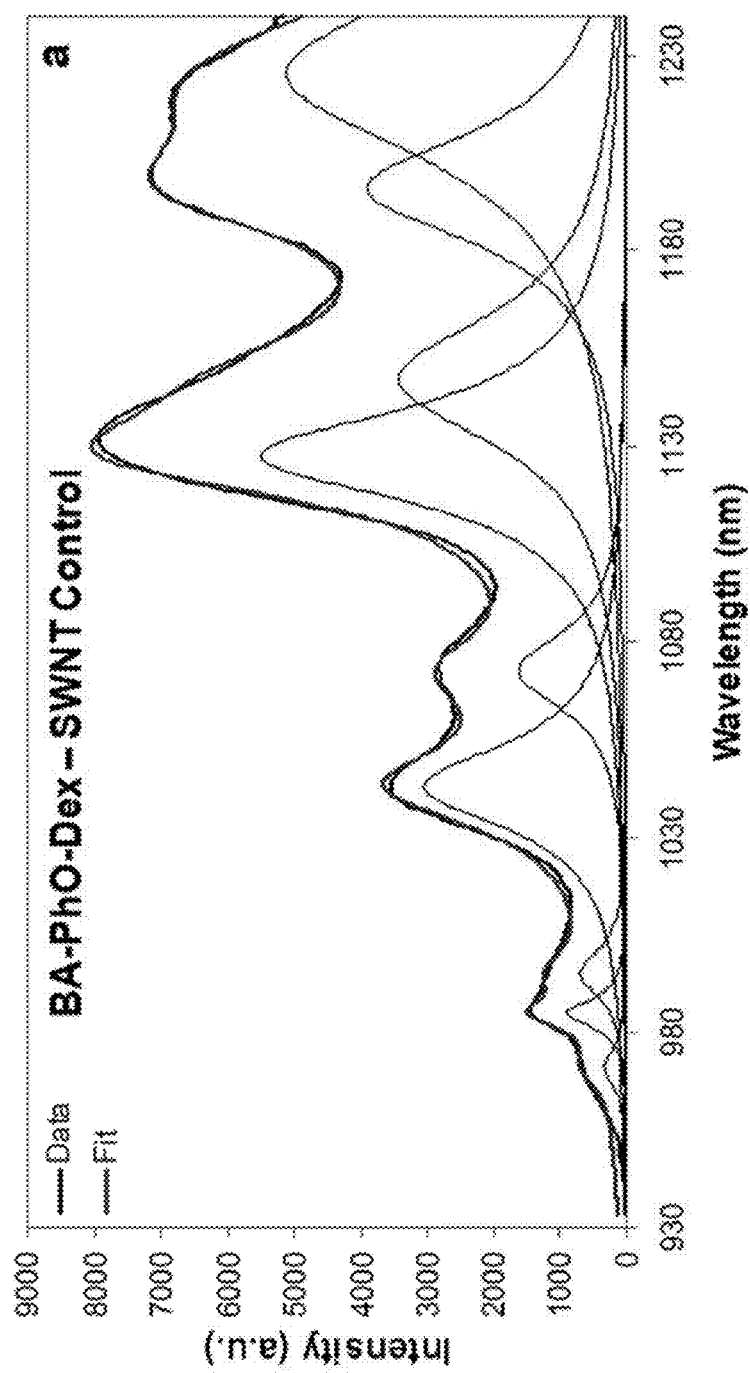
FIGS. 29-30 are deconvoluted spectra of fluorescence response of each nanotube species in BA-PhO-Dex-SWNT to different analytes.
Figure 29B:
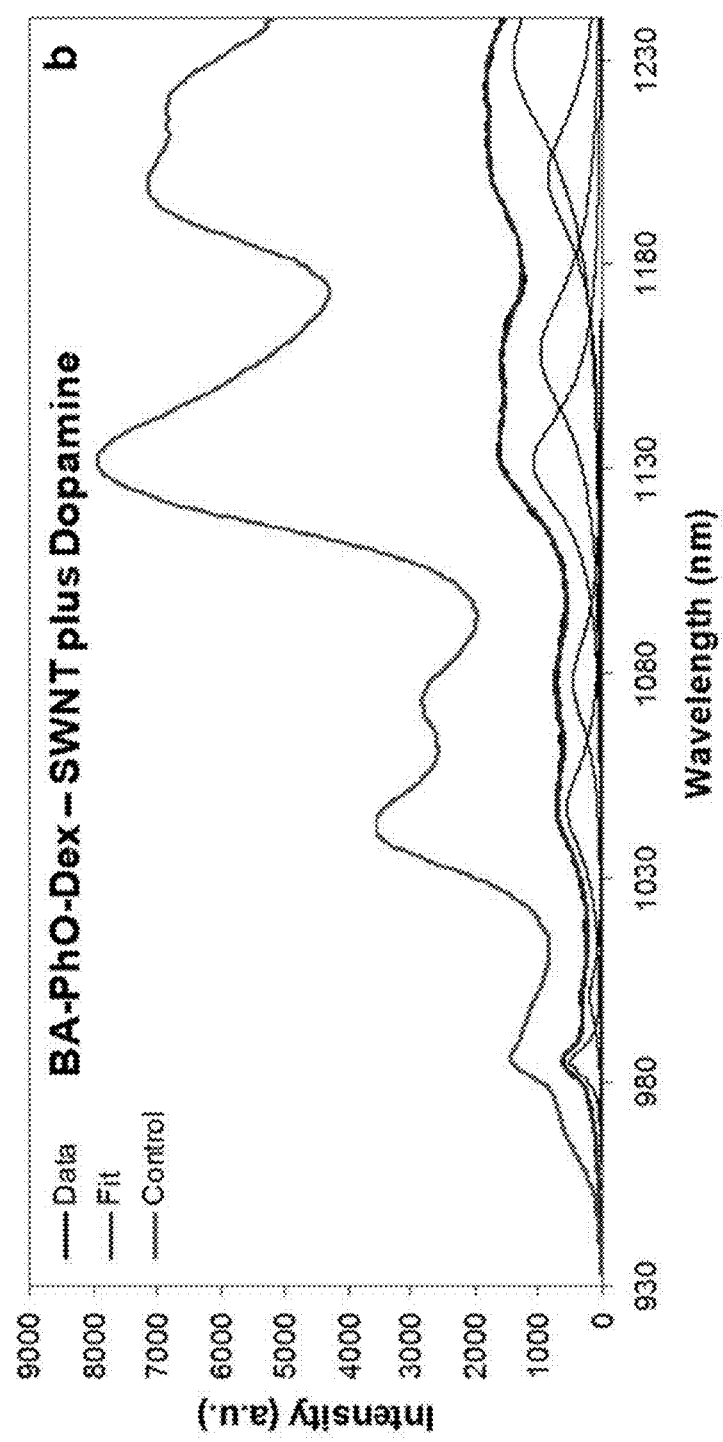
Figure 29C:
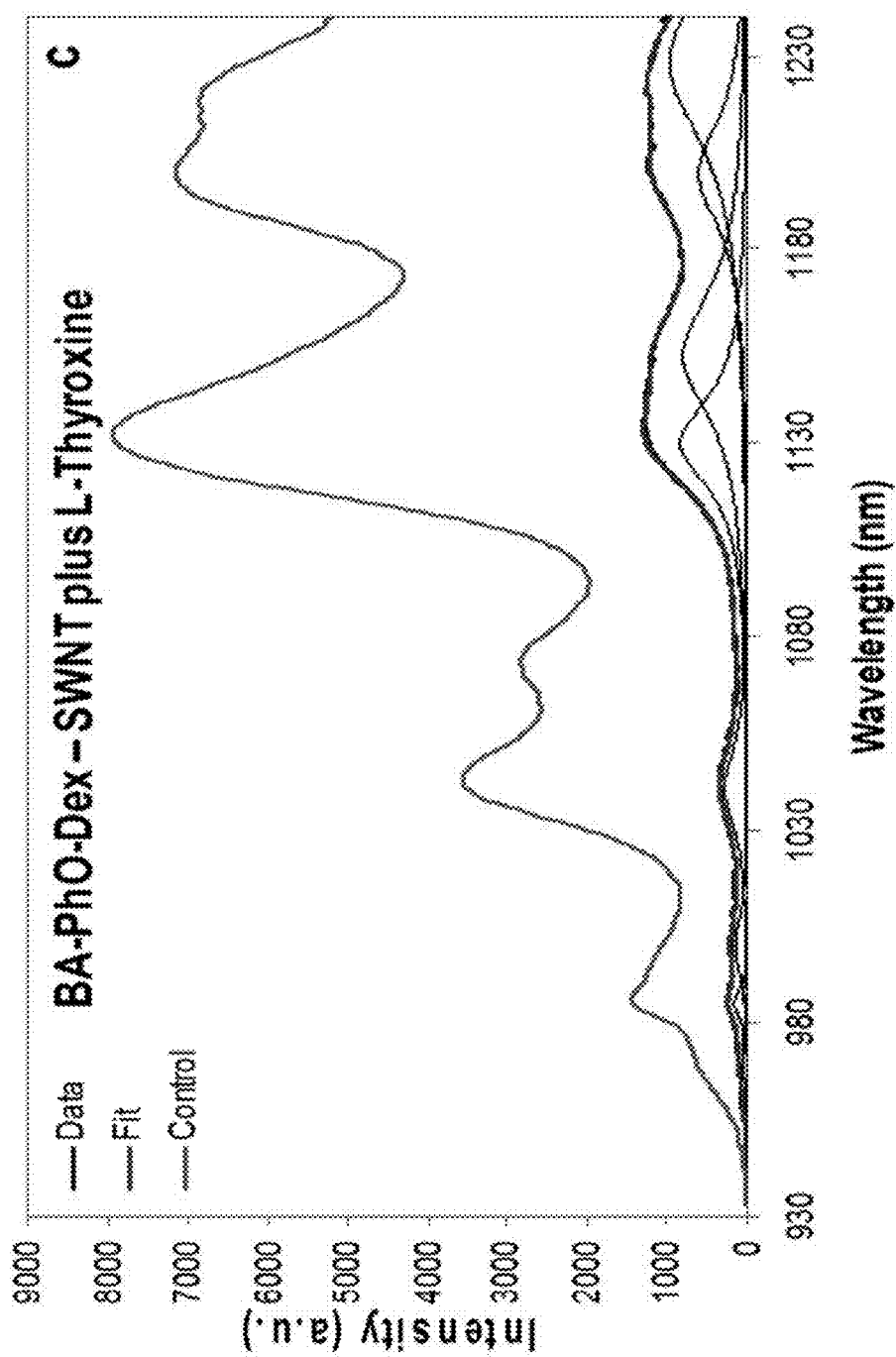
Figure 30A:
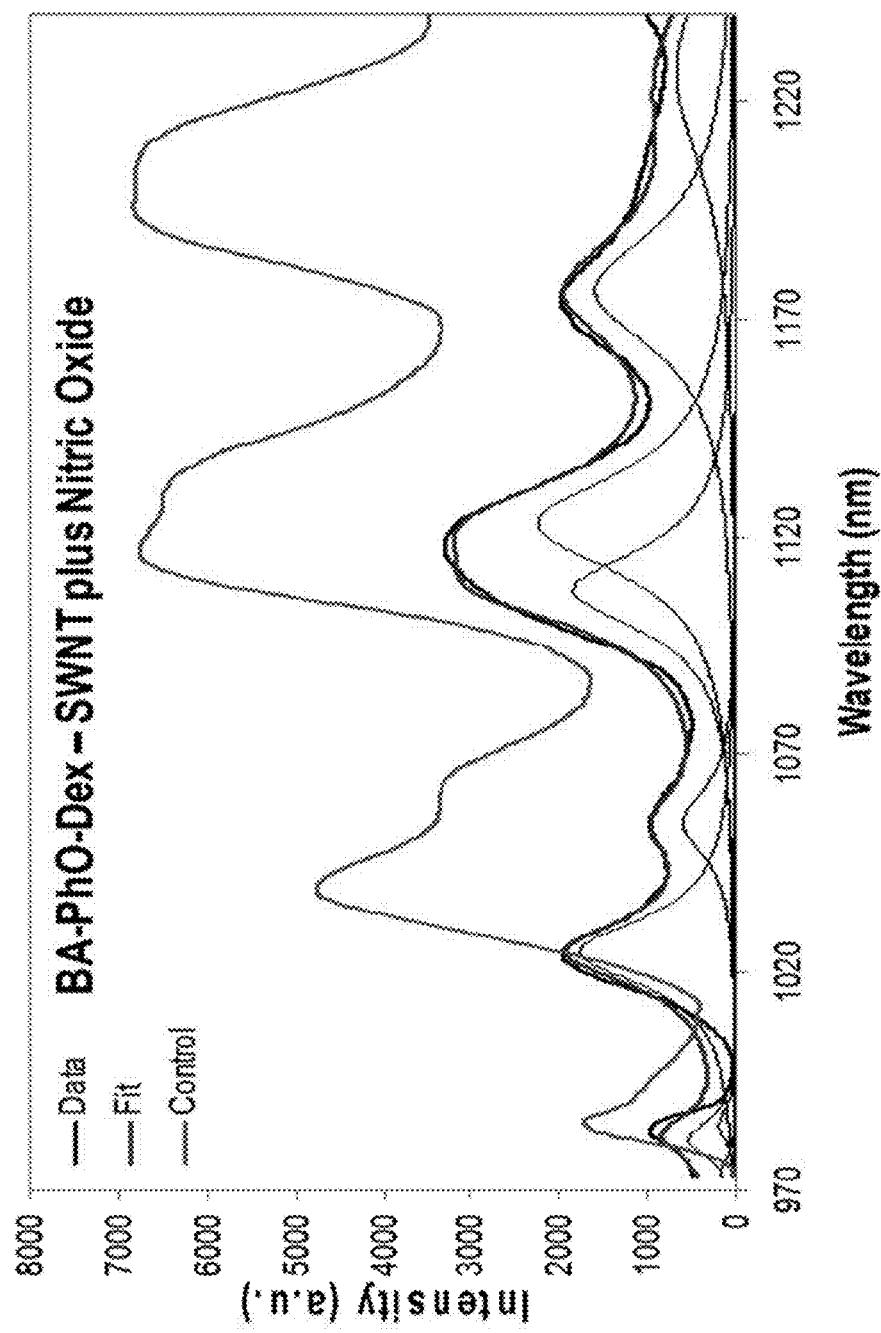
Figure 30B:
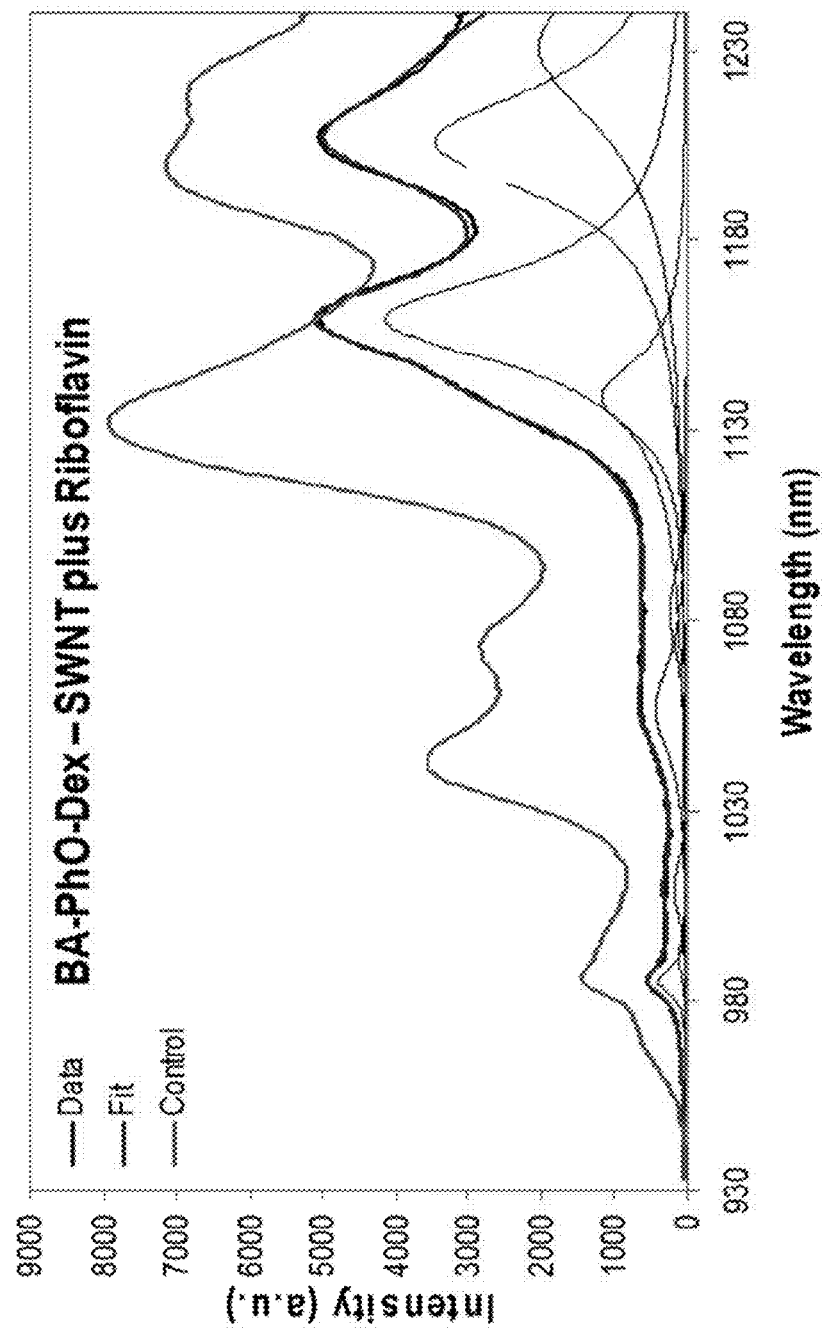
Figure 31A:
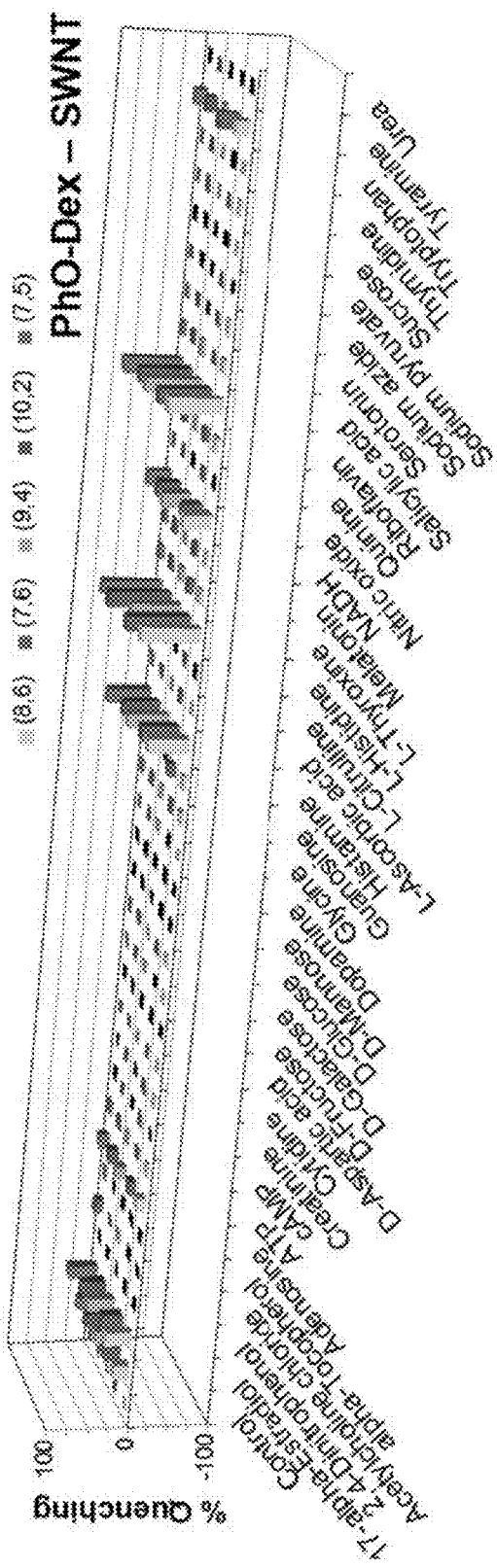
FIG. 31 includes two plots of the nanotube specific fluorescence response of PhO-Dex-SWNT to different analytes.
Figure 31B:
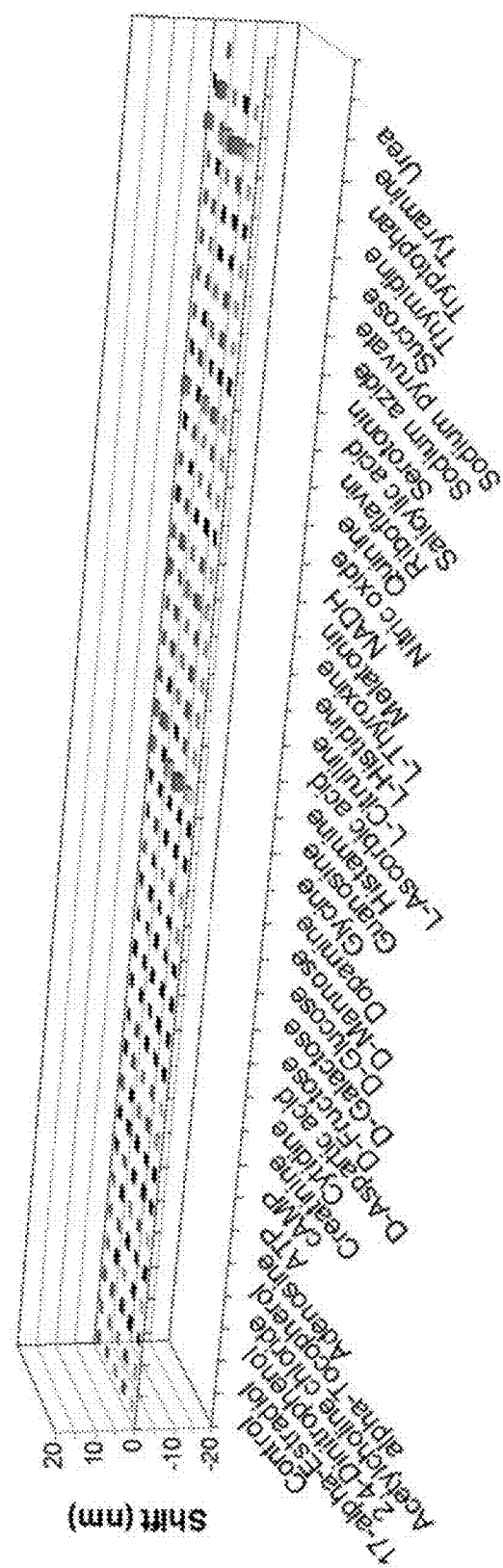
Figure 32A:
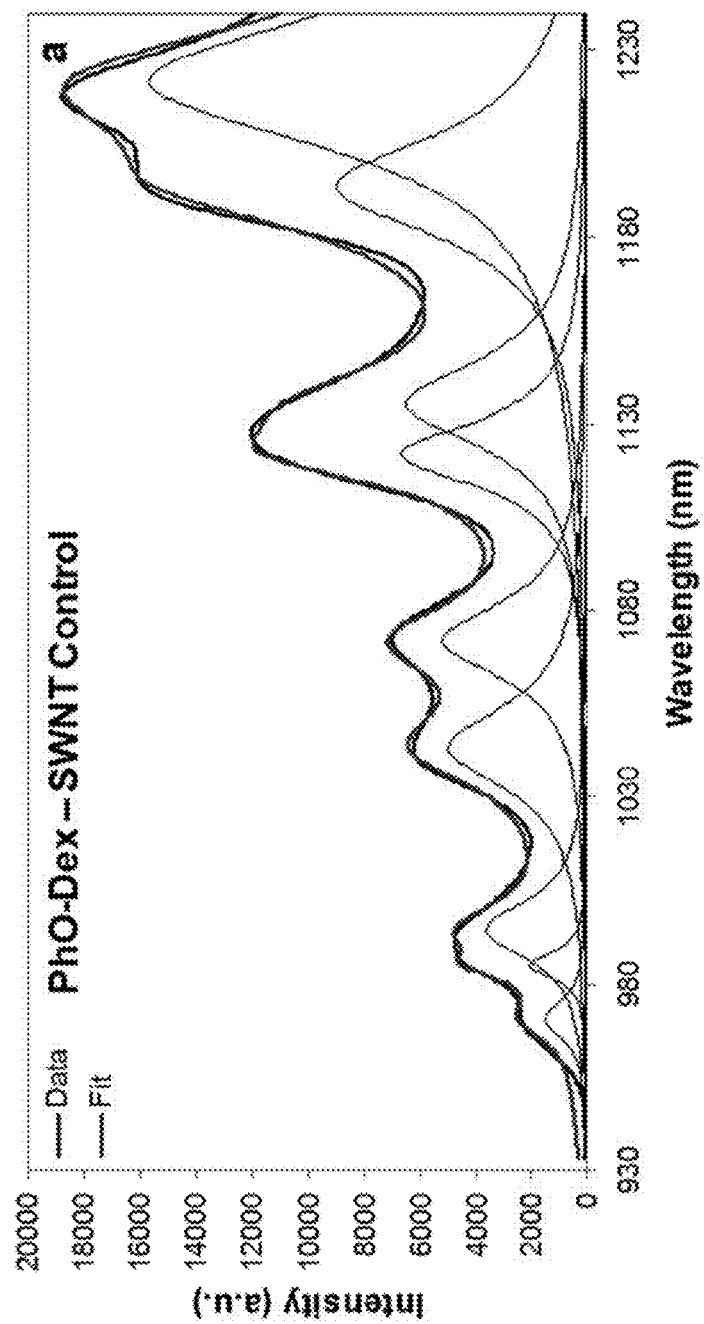
FIGS. 32-33 are deconvoluted spectra of fluorescence response of each nanotube species in PhO-Dex-SWNT to different analytes.
Figure 32B:
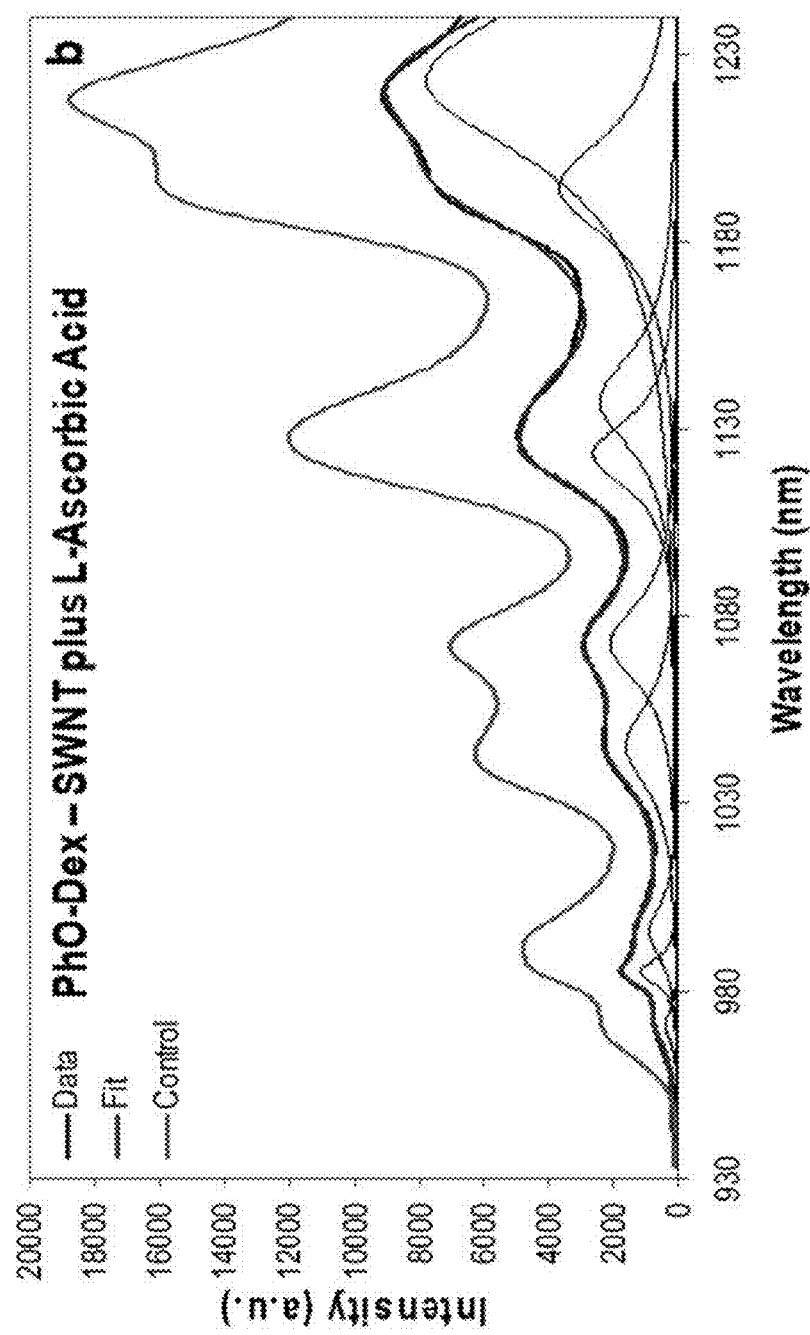
Figure 32C:
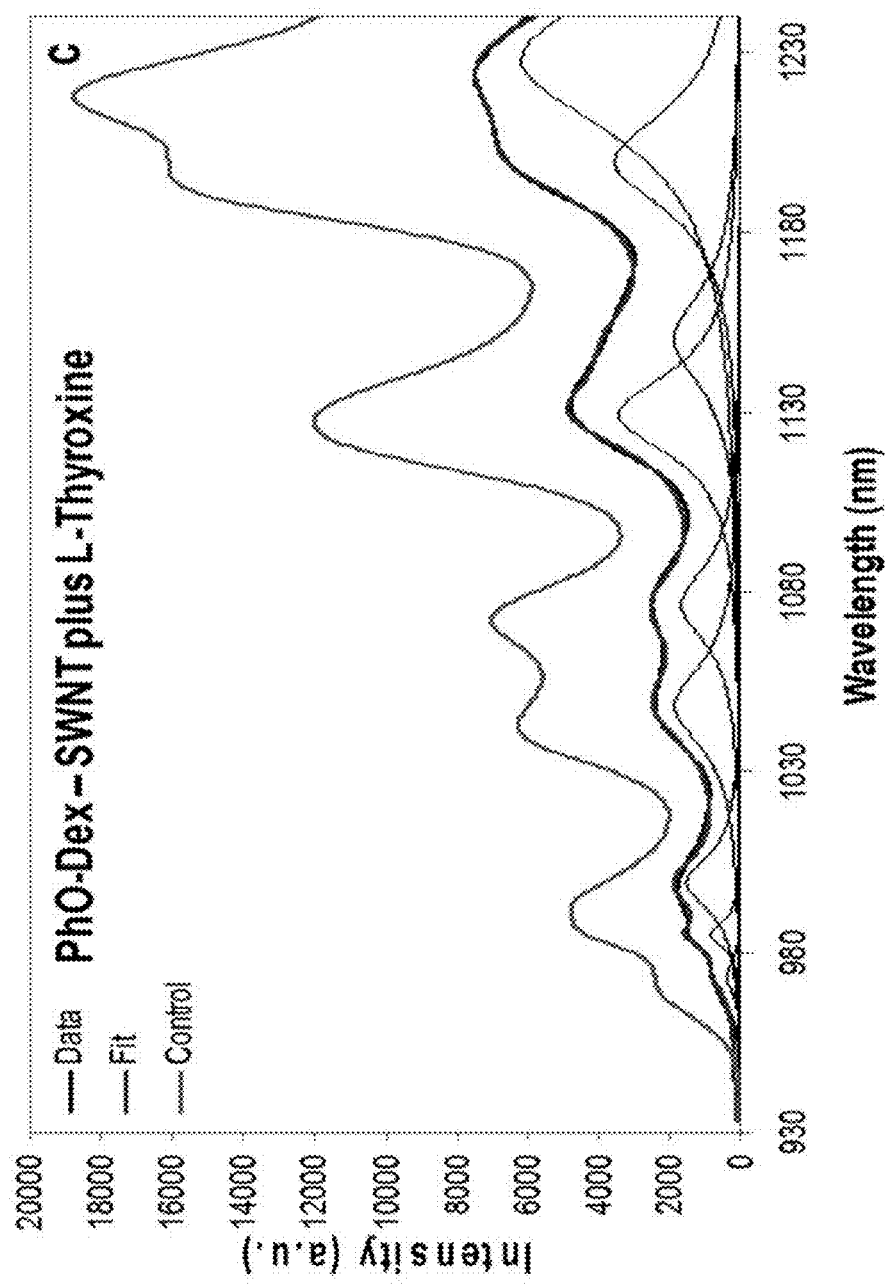
Figure 33A:
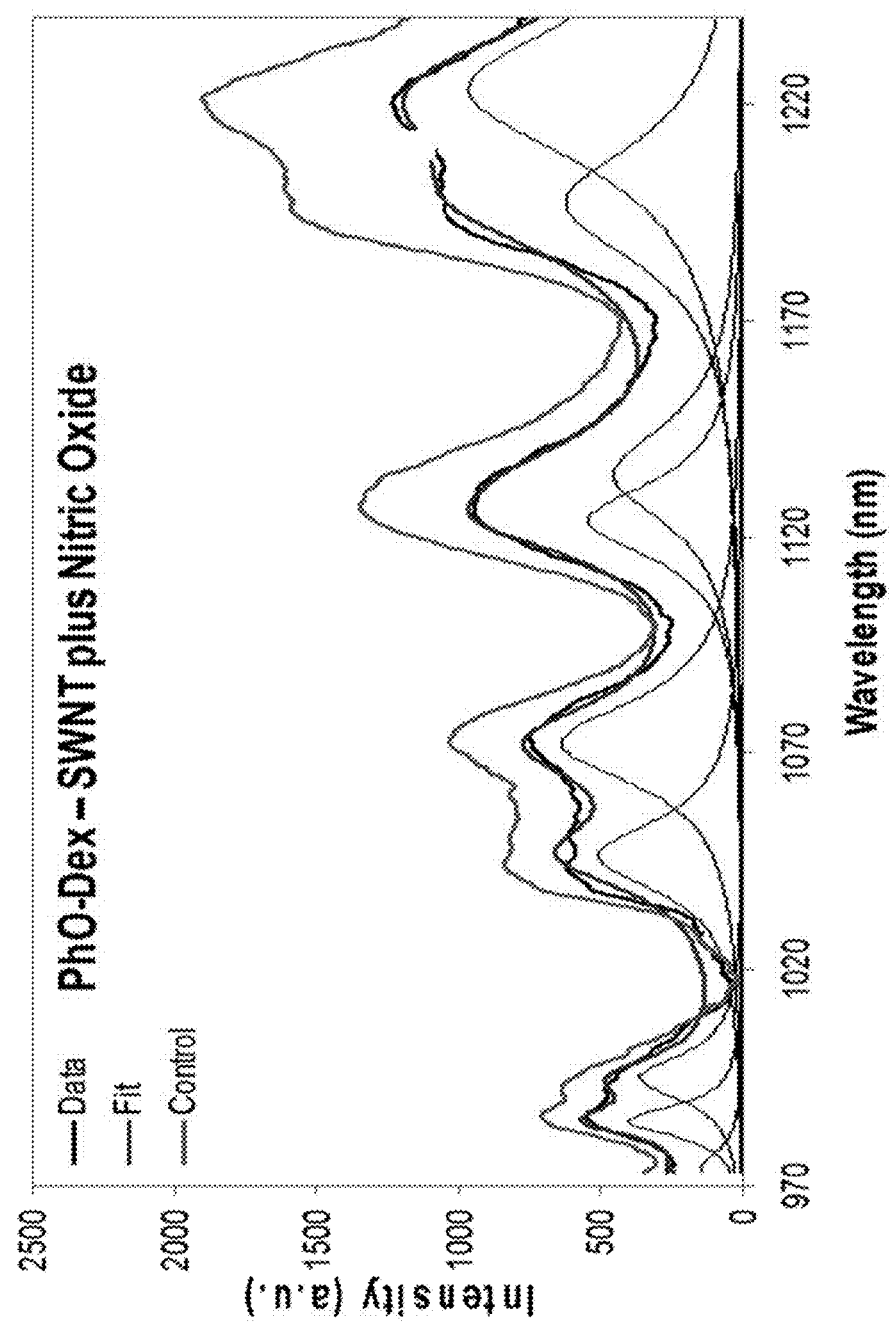
Figure 33B:
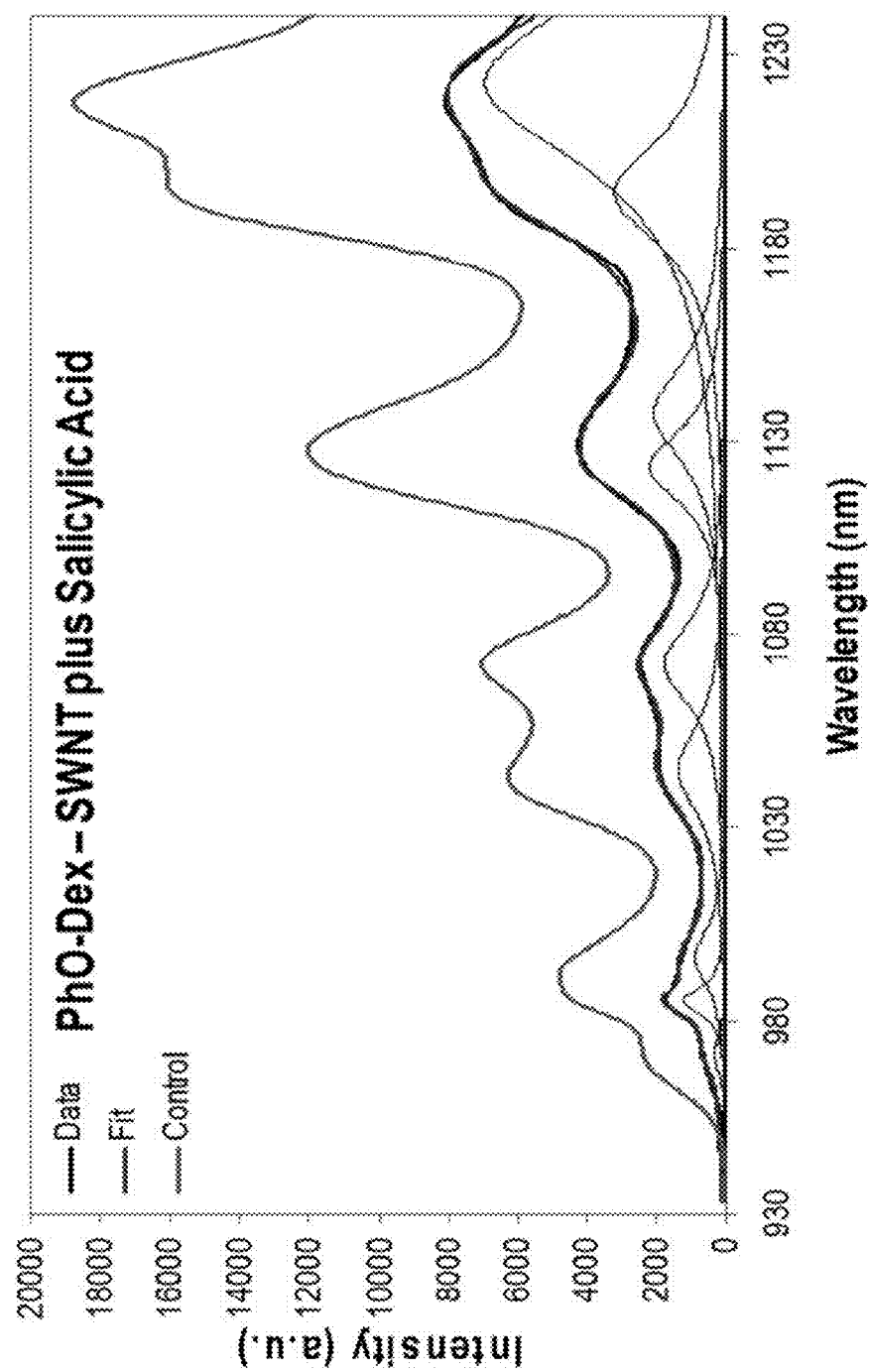
Figure 34A:
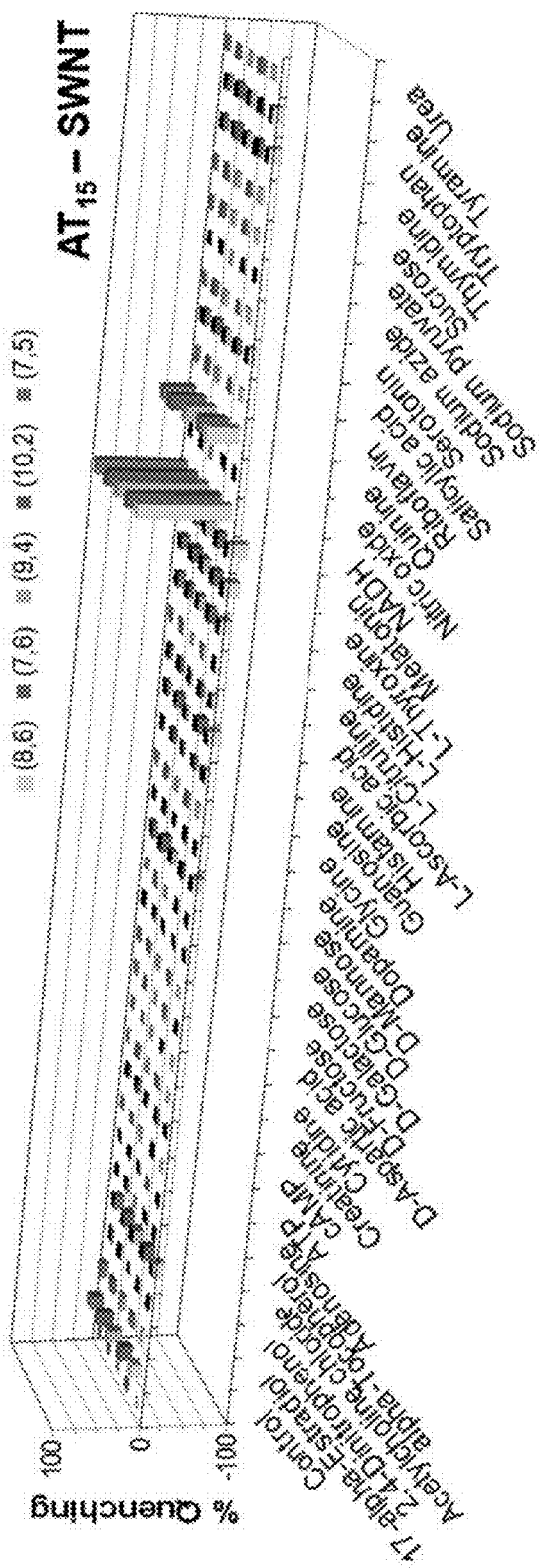
FIG. 34 includes two plots of the nanotube specific fluorescence response of $AT_{15}$-SWNT to different analytes.
Figure 34B:
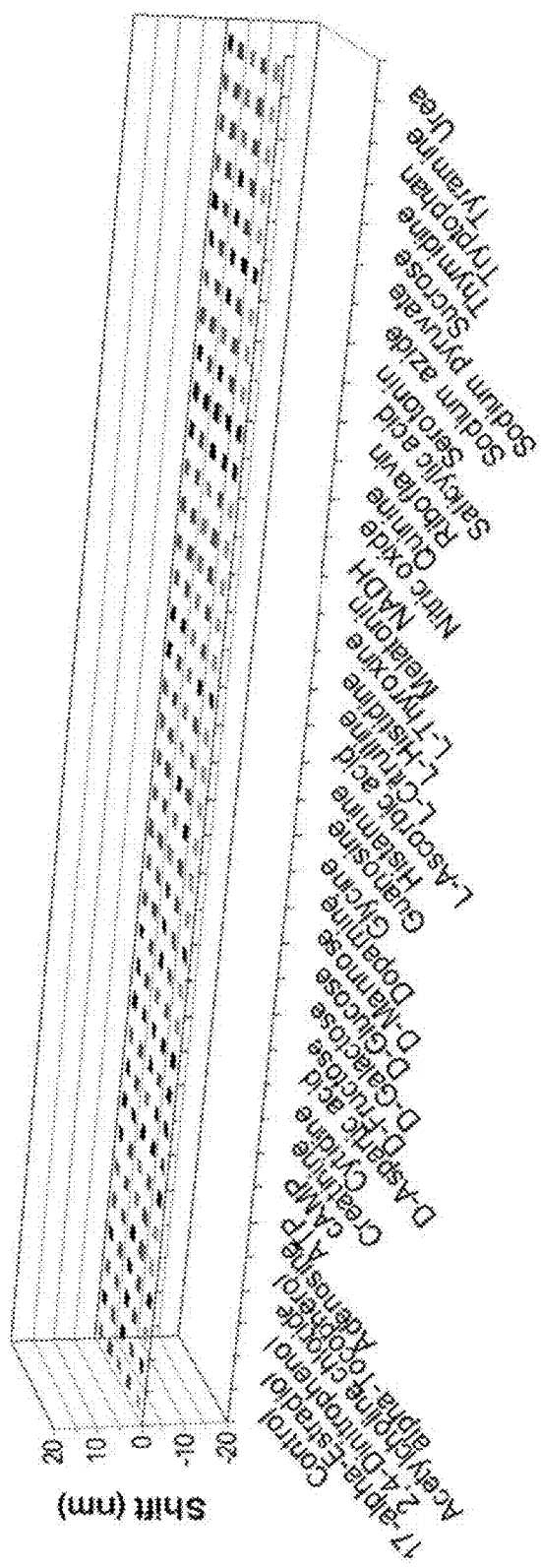
Figure 35A:
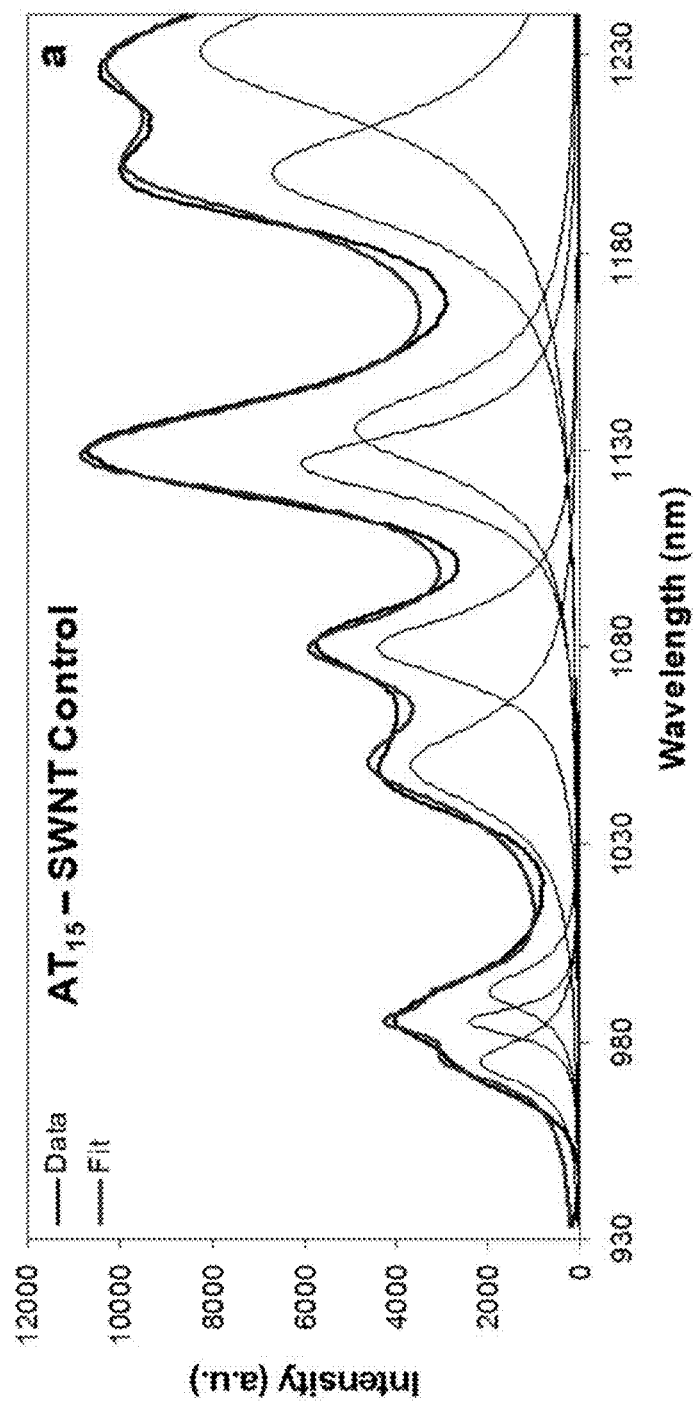
FIG. 35 is deconvoluted spectra of fluorescence response of each nanotube species in $AT_{15}$-SWNT to 36 different analytes.
Figure 35B:
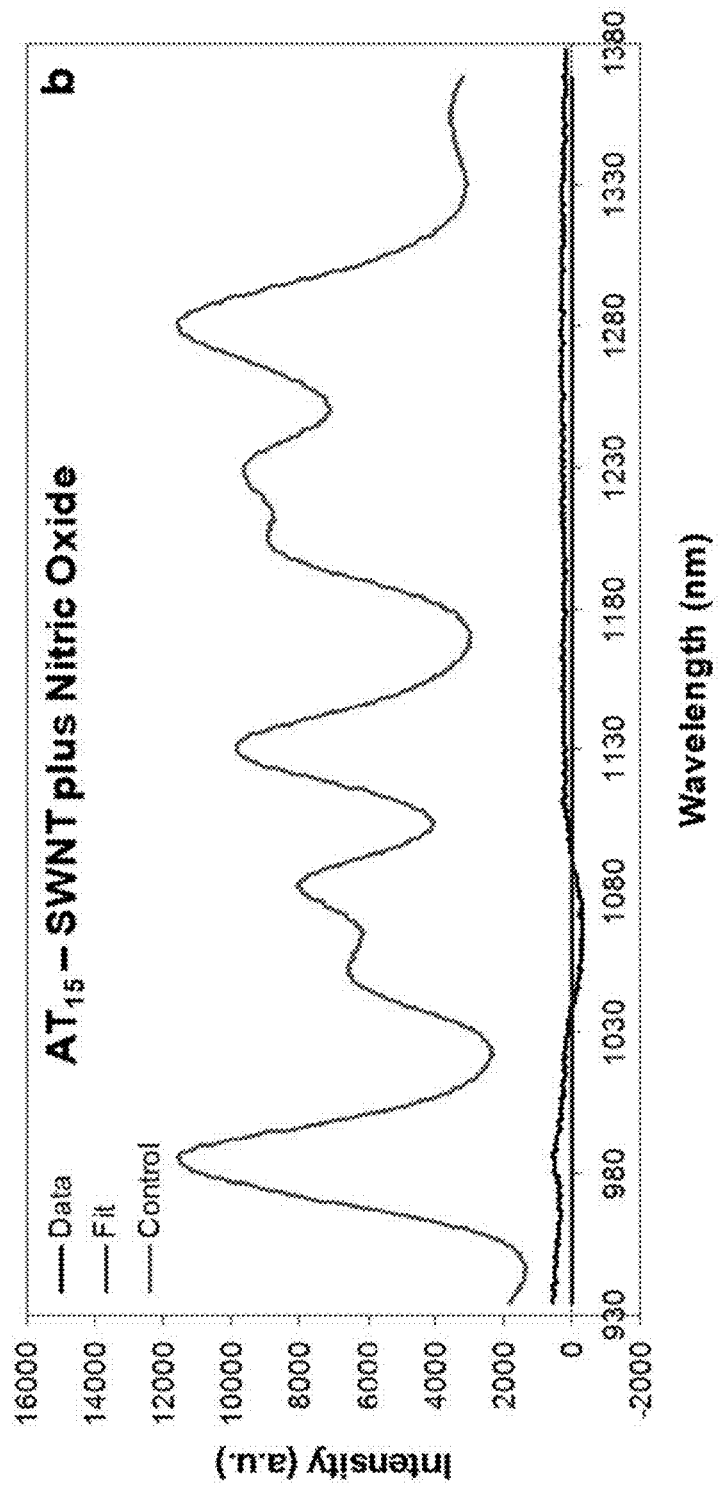
Figure 35C:
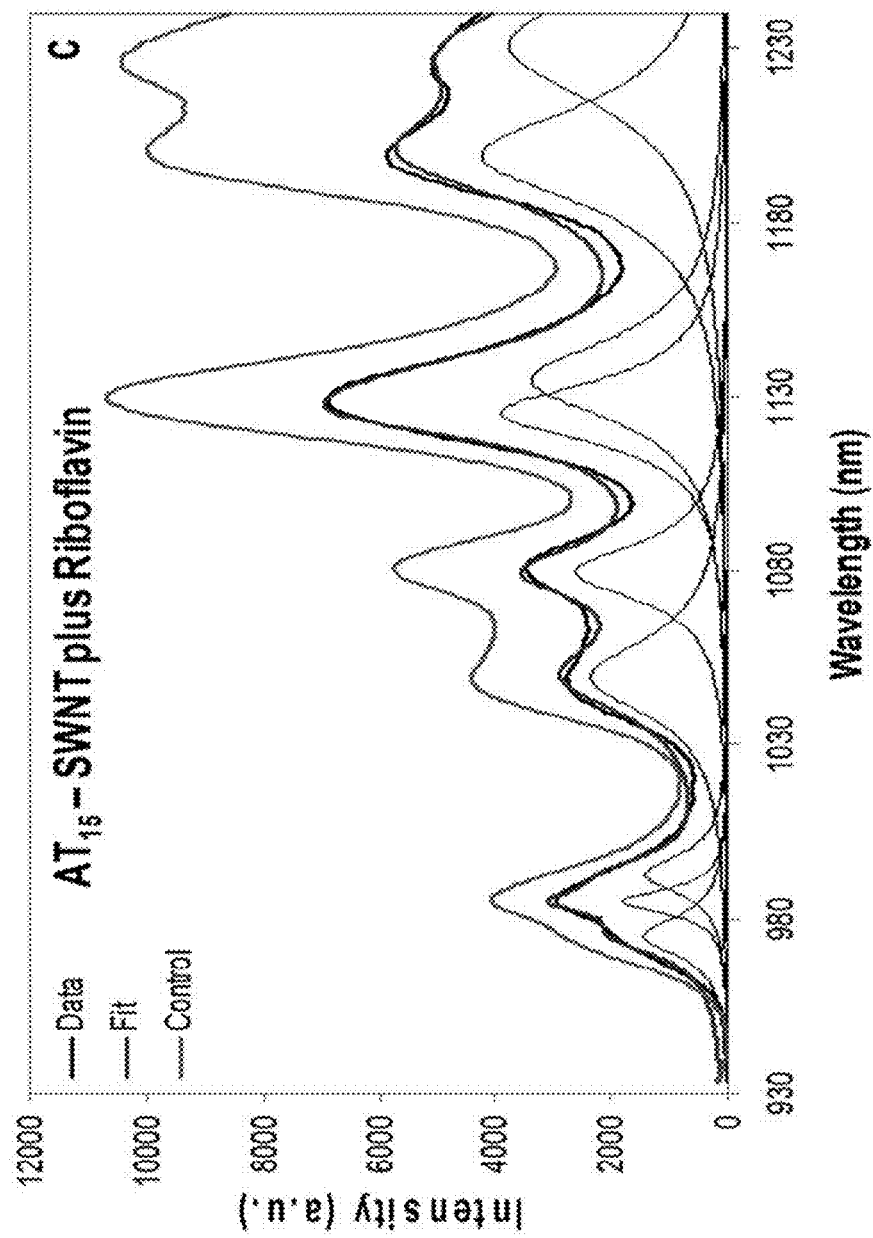

SWNT photoluminescence showed stepwise increases and quenching. This is likely due to the adsorption or desorption of nitric oxide onto the $AT_{15}$-SWNT surface. The fluorescence within a 2×2 pixel spatial binning region in the movie images was examined and the analysis algorithm is similar to that reported before. (Jin, H., et al., (2008)). The four-pixel area in the image corresponded to a 600×600 nm² region in the real sample, which was proposed to represent the photoluminescence from a single SWNT, as determined by the diffraction limit in the nIR range. (Cognet, L., et al., (2007)). Hidden Markov Modeling (HMM) was employed to correlate the rate constant of adsorption and desorption of events to the concentration of nitric oxide, which provided a concentration calibration curve (FIG. 20). ((Jin, H., et al., (2008); McKinney, S., et al., Analysis of single-molecule FRET trajectories using hidden Markov modeling. Biophysical Journal 91, 1941-1951 (2006), which is incorporated by reference in its entirety).

Molecular Fingerprint Data:

Polymers were synthesized by direct or combinatorial methods. DNA oligonucleotides or peptides of various sequences were used to suspend SWNTs and subsequently screened against 96 biologically relevant analytes (36 were chosen for facile comparison, FIG. 13 and Table 1). As an estimate of the size of the resulting data set, for each polymer wrapping there were 576 data-points from eight unique SWNT chiralities, two SWNT photoluminescence modalities (intensity and wavelength), and 36 analytes. (Heller, D. A., et al., (2008)). Screening 10 polymer-SWNT complexes at 30 s/analyte in triplicate with control spectra took approximately 30 hours. The photoluminescence peak center and intensity of each nanotube were obtained through automated spectral deconvolution. This data set formed a molecular "fingerprint". The data set provided information about, among other variables, the spatial configuration and permeability of the adsorbed phase around the nanotube, its redox state and the ability for target molecules to dynamically modulate the adsorbed phase in a switch-like fashion. This fingerprint can be a useful tool for understanding nanotube-bound polymer phases because conventional methods (mass spectrometry, nuclear magnetic resonance) provide less information about the poly-SWNT complex. One general observation made from this data set was that a wavelength shift in response to analyte adsorption appeared to be far rarer than an intensity change (FIGS. 21-57).

TABLE 1

Concentration of analytes listed in the high-throughput screening assay.

| Analyte | Concentration mM |
|---|---|
| 17-a-Estradiol | 0.10 |
| 2,4-Dinitrophenol | 0.48 |
| Acetylcholine chloride | 0.54 |
| a-Tocopherol | 0.51 |
| Adenosine | 0.51 |
| ATP | 0.11 |
| cAMP | 0.10 |
| Creatinine | 0.10 |
| Cytidine | 0.48 |
| D-Aspartic acid | 0.02 |
| D-Fructose | 10.80 |
| D-Galactose | 5.00 |
| D-Glucose | 10.90 |
| D-Mannose | 10.30 |
| Dopamine | 0.49 |
| Glycine | 0.50 |
| Guanosine | 0.51 |
| Histamine | 0.51 |
| L-Ascorbic acid | 0.50 |
| L-Citrulline | 0.11 |
| L-Histidine | 0.10 |
| L-Thyroxine | 0.50 |
| Melatonin | 0.49 |
| NADH | 0.51 |
| Nitric oxide | 0.03 |
| Quinine | 0.01 |
| Riboflavin | 0.1 |
| Salicylic acid | 0.49 |
| Serotonin | 0.11 |
| Sodium azide | 0.51 |
| Sodium pyruvate | 0.50 |
| Sucrose | 0.10 |
| Thymidine | 0.52 |
| Tryptophan | 0.25 |
| Tyramine | 0.49 |
| Urea | 0.49 |

Figure 4B:
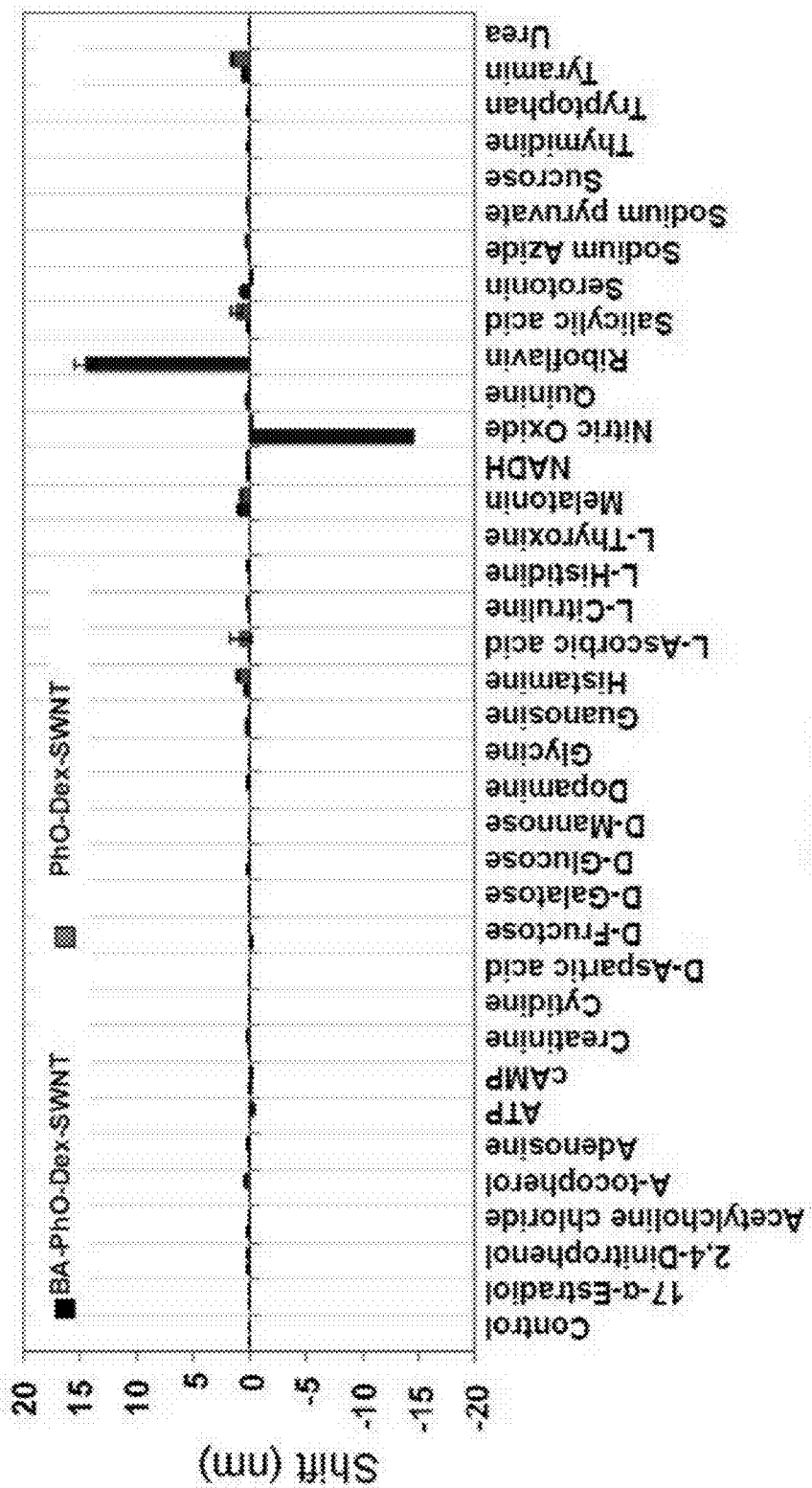
Figure 6A:
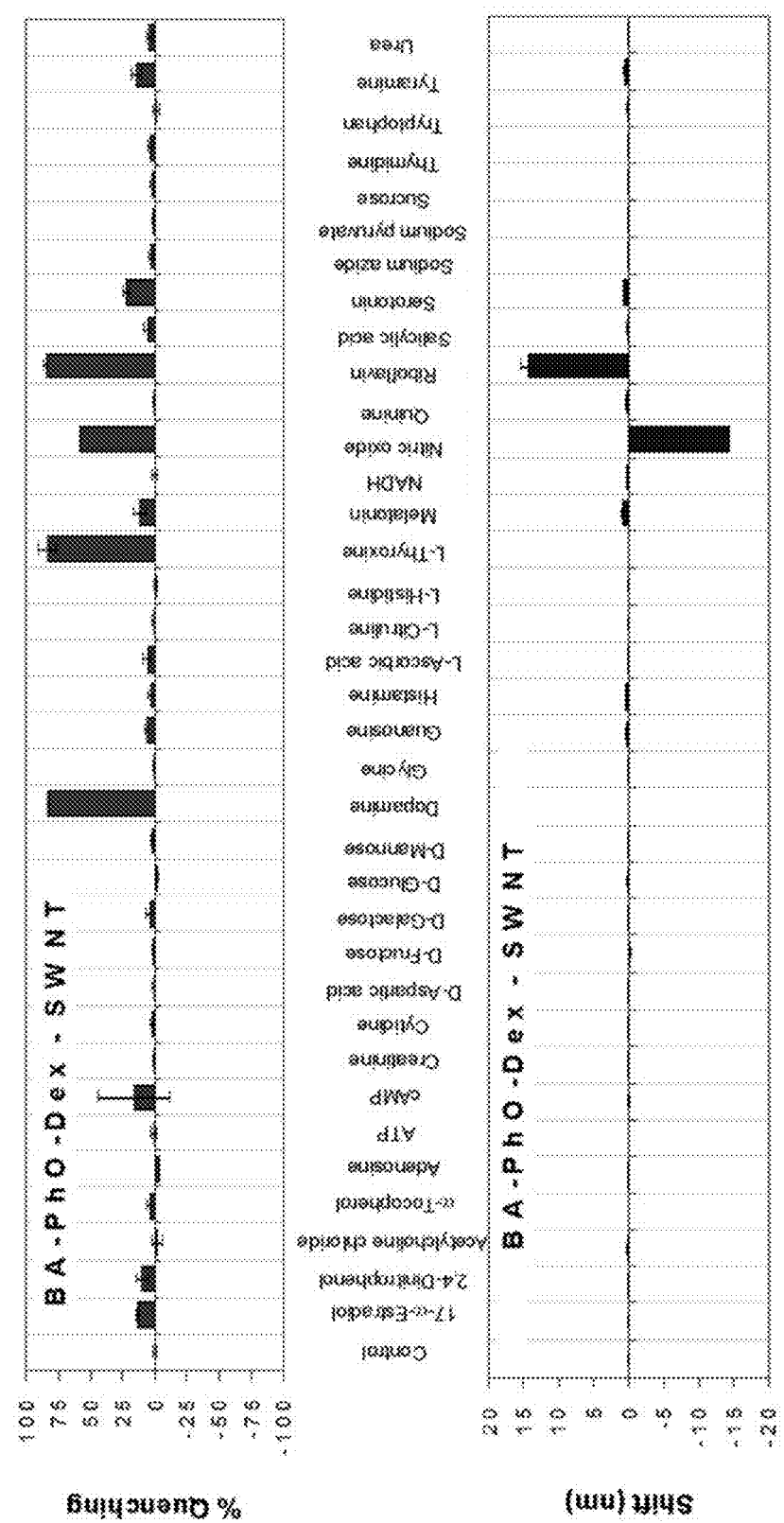
FIG. 6 demonstrates fluorescence quenching and emission maximum shift responses for the (7,5) nanotube from BA-PhO-Dex-SWNT and PhO-Dex-SWNT after being queried with potential analytes.
Figure 6B:
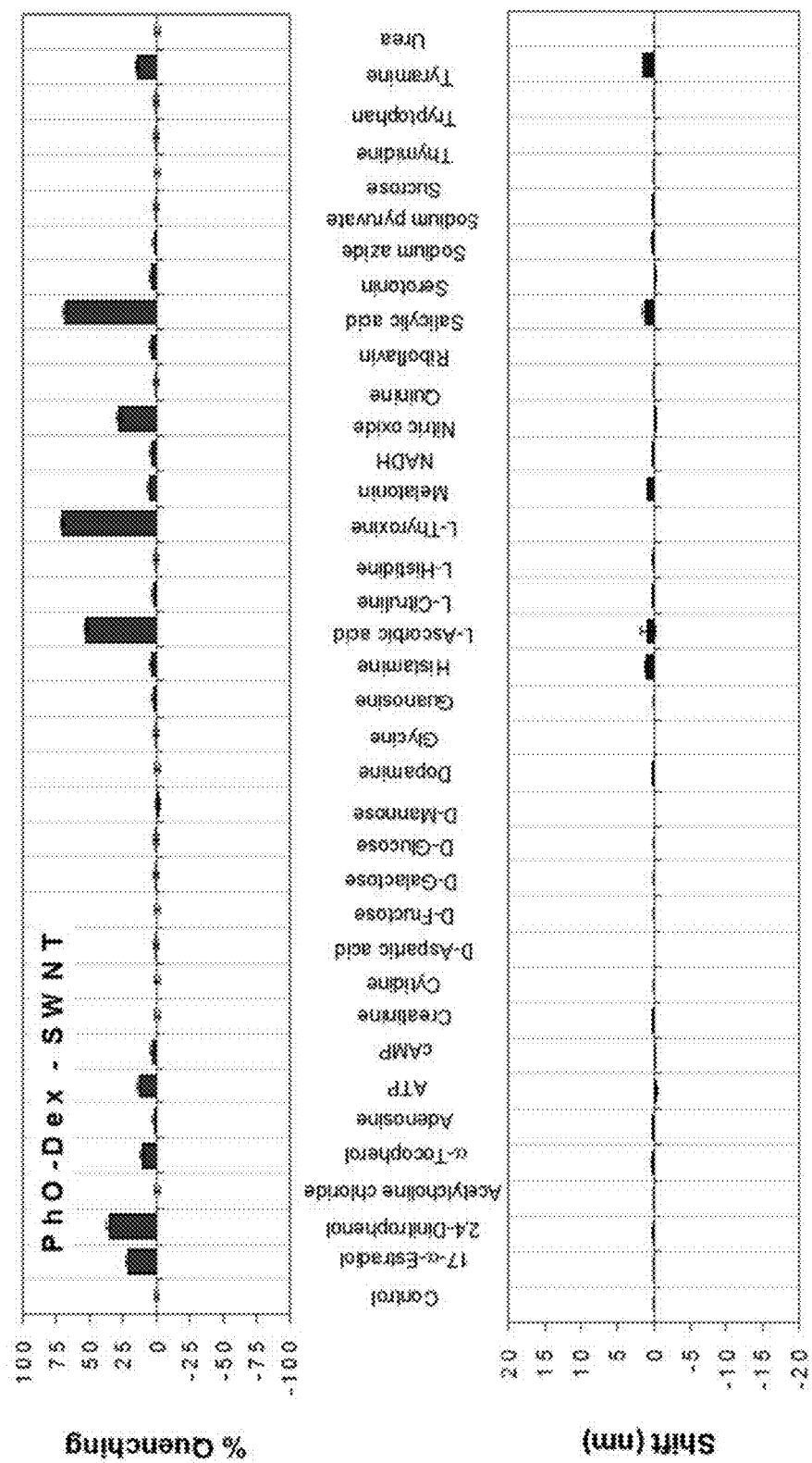
Figure 49A:
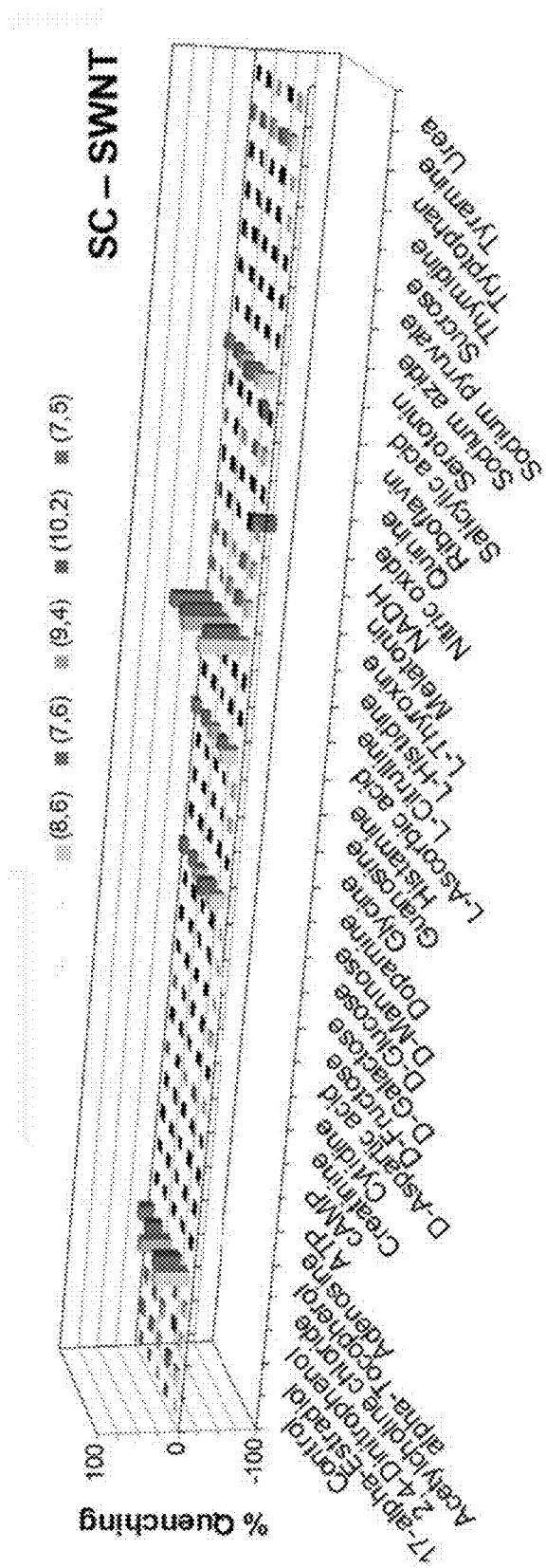
FIG. 49 includes two plots of the nanotube specific fluorescence response of SC-SWNT to different analytes.
Figure 49B:
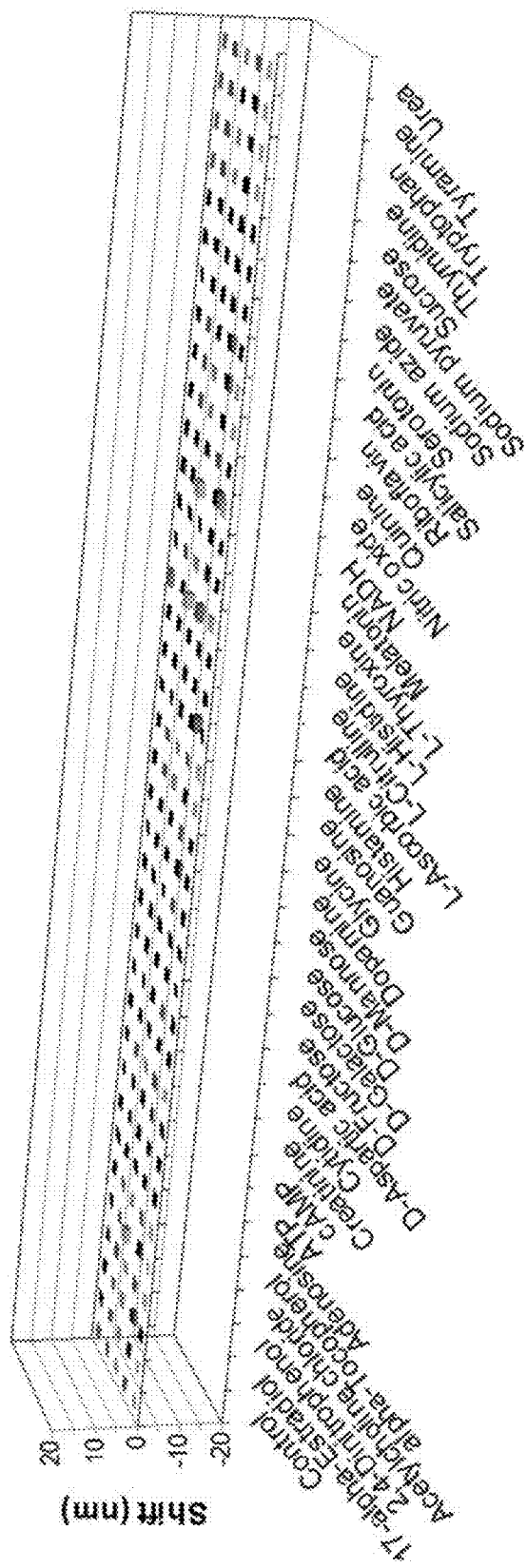
Figure 50:
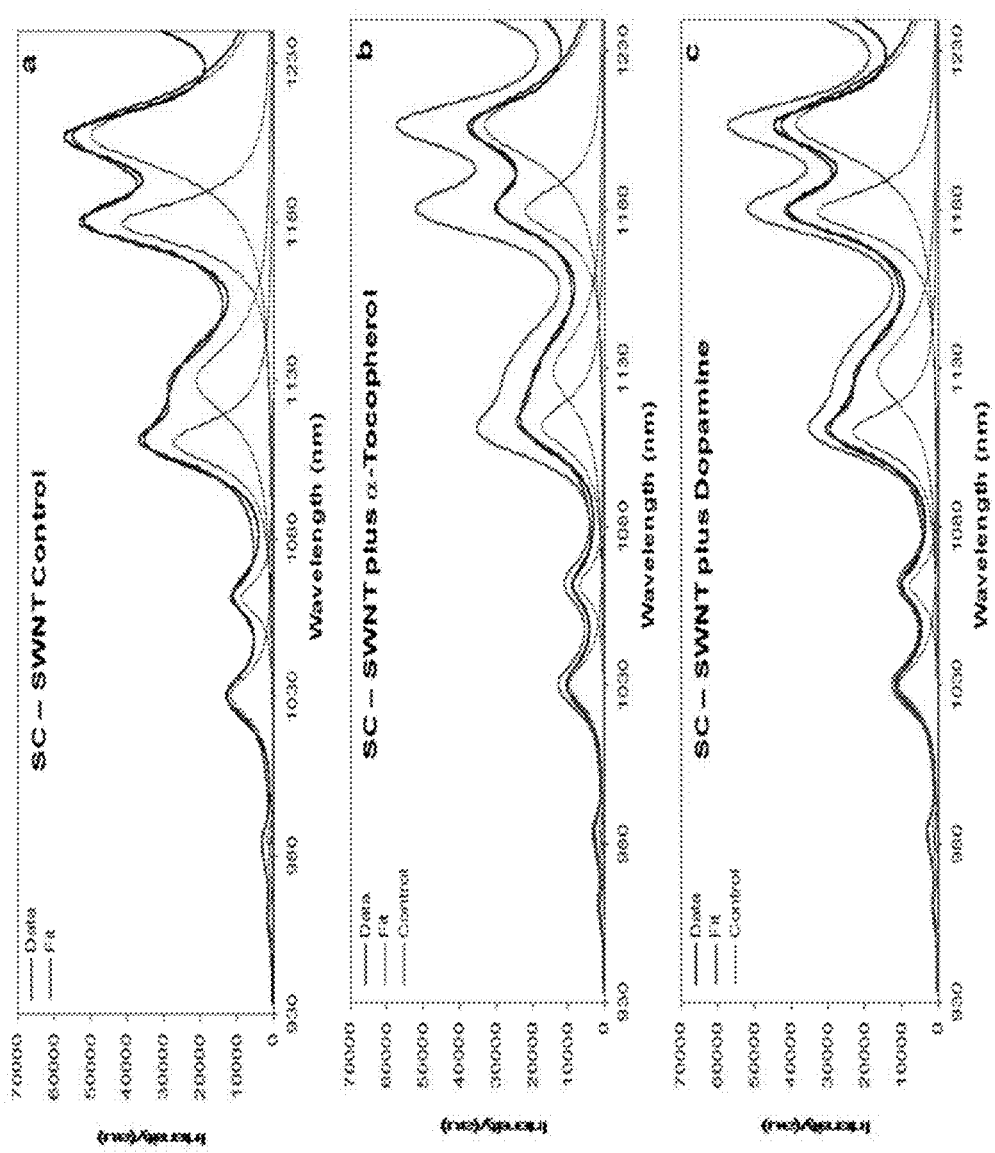
FIGS. 50-51 are deconvoluted spectra of fluorescence response of each nanotube species in SC-SWNT to different analytes.
Figure 51:
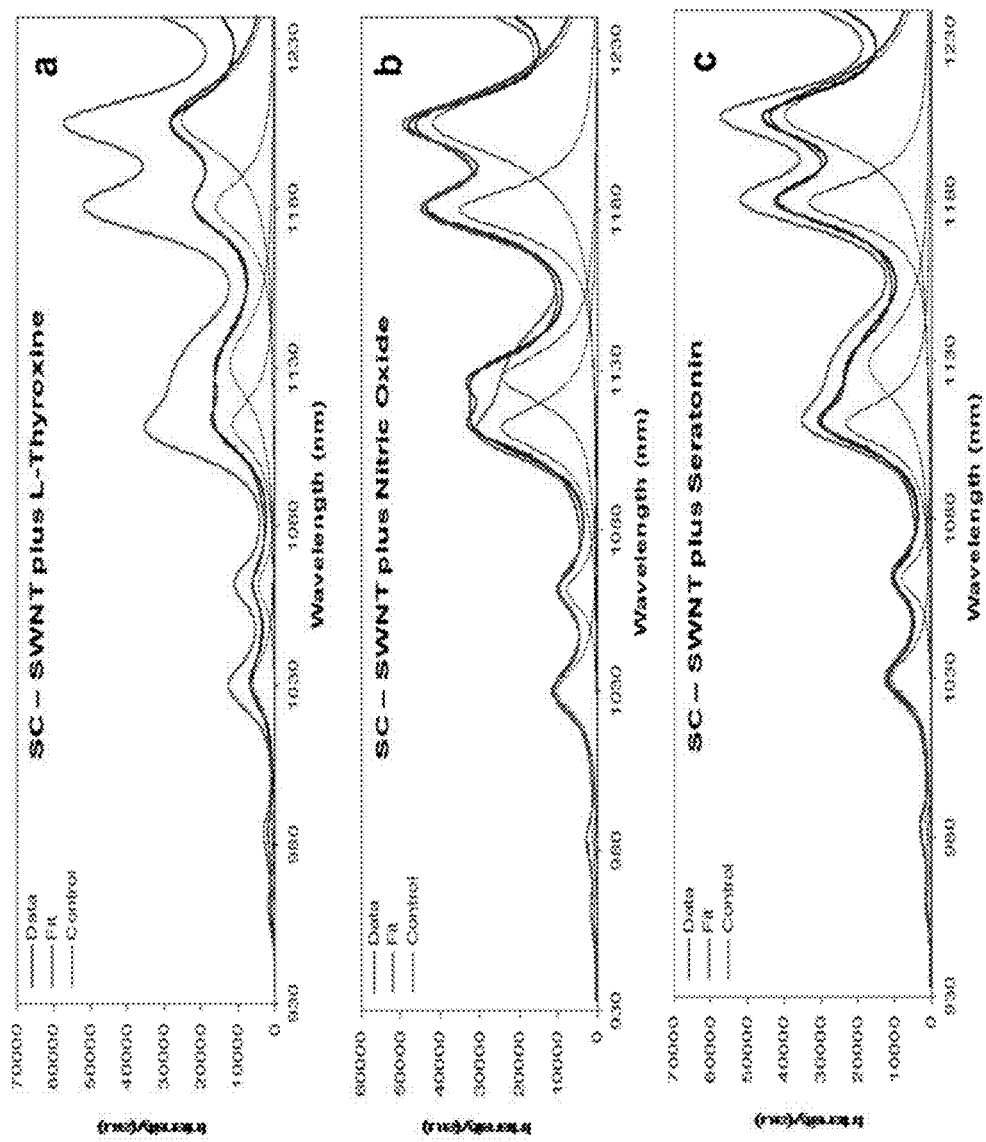
Figure 52A:
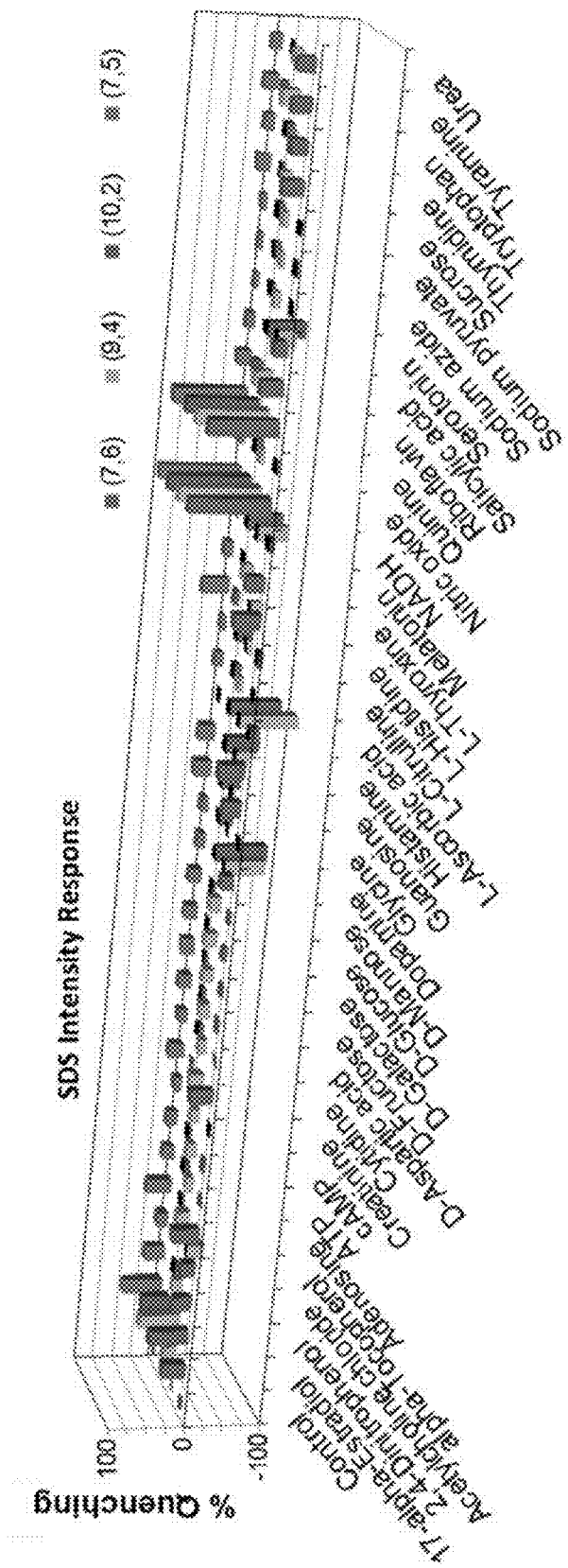
FIG. 52 includes two plots of the nanotube specific fluorescence response of SDS-SWNT to 36 different analytes.
Figure 52B:
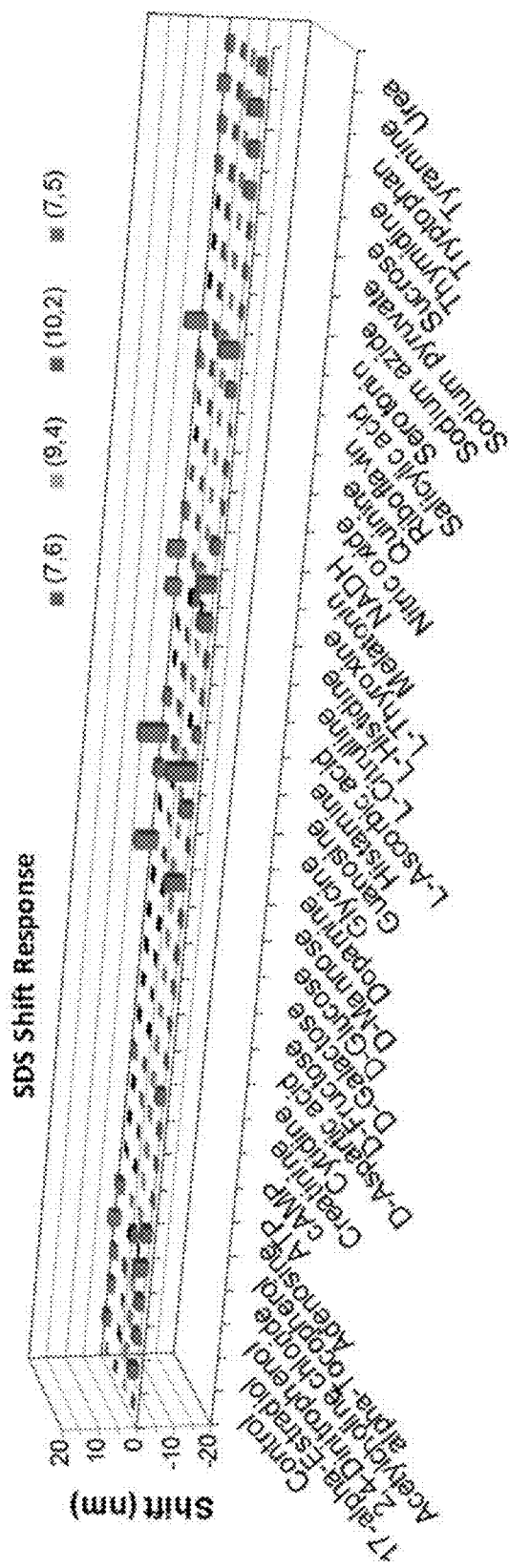
Figure 53:
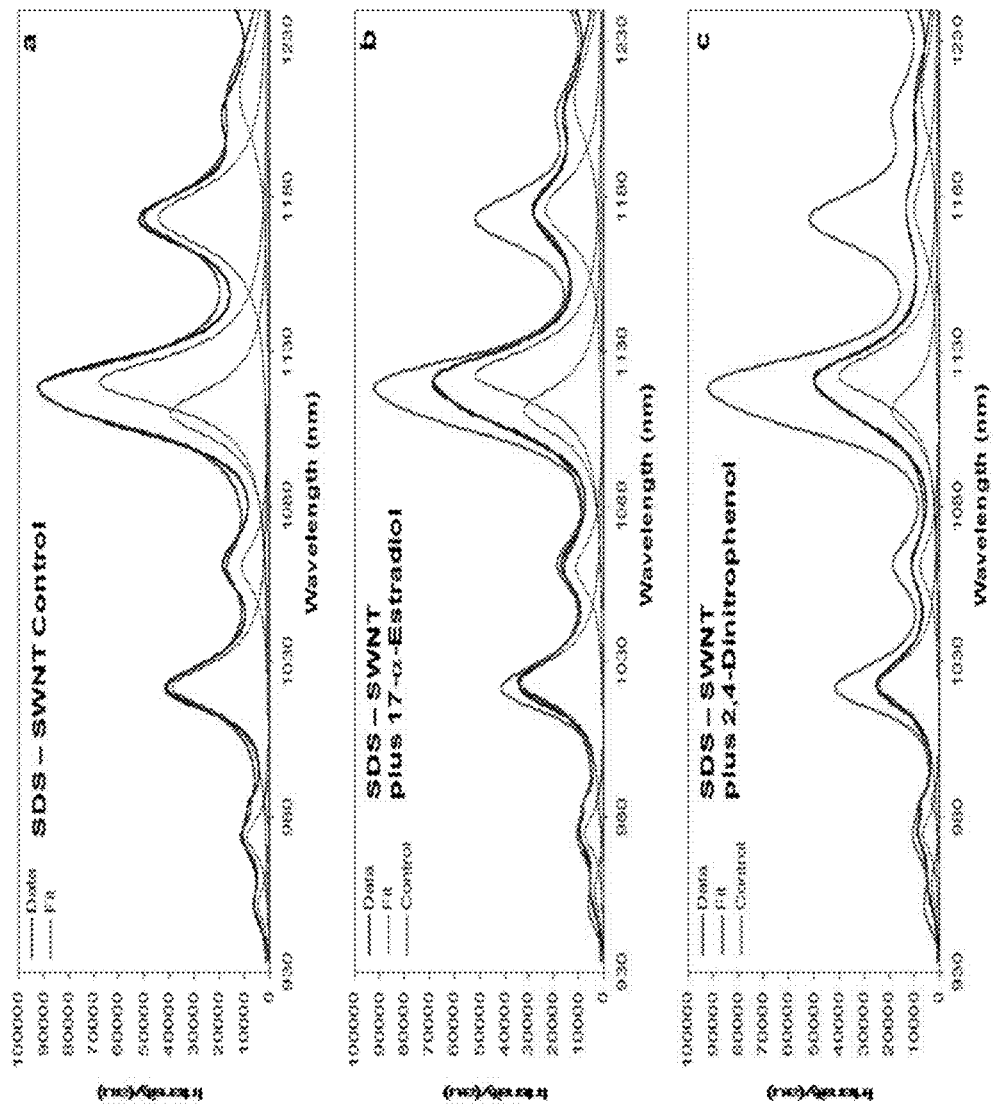
FIGS. 53-57 are deconvoluted spectra of fluorescence response of each nanotube species in SDS-SWNT to different analytes.
Figure 54:
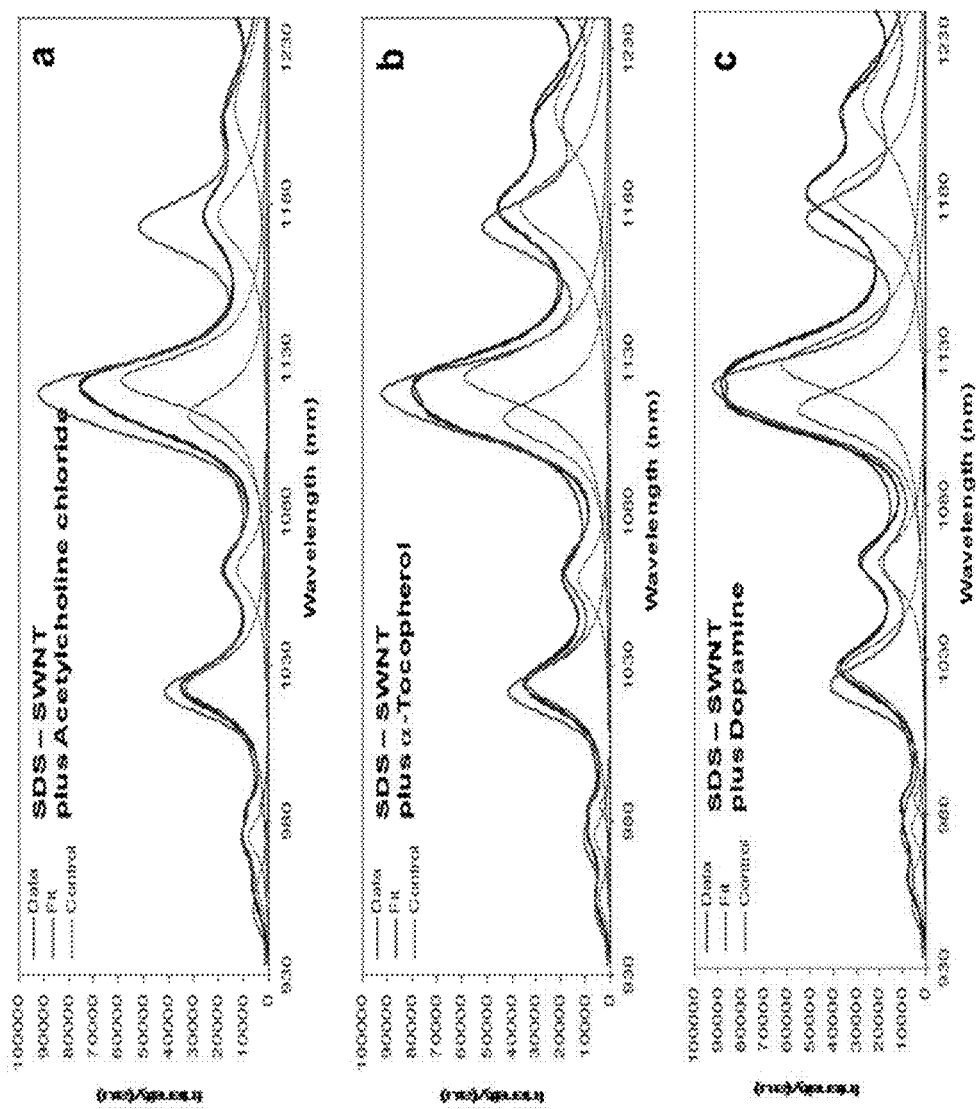
Figure 55:
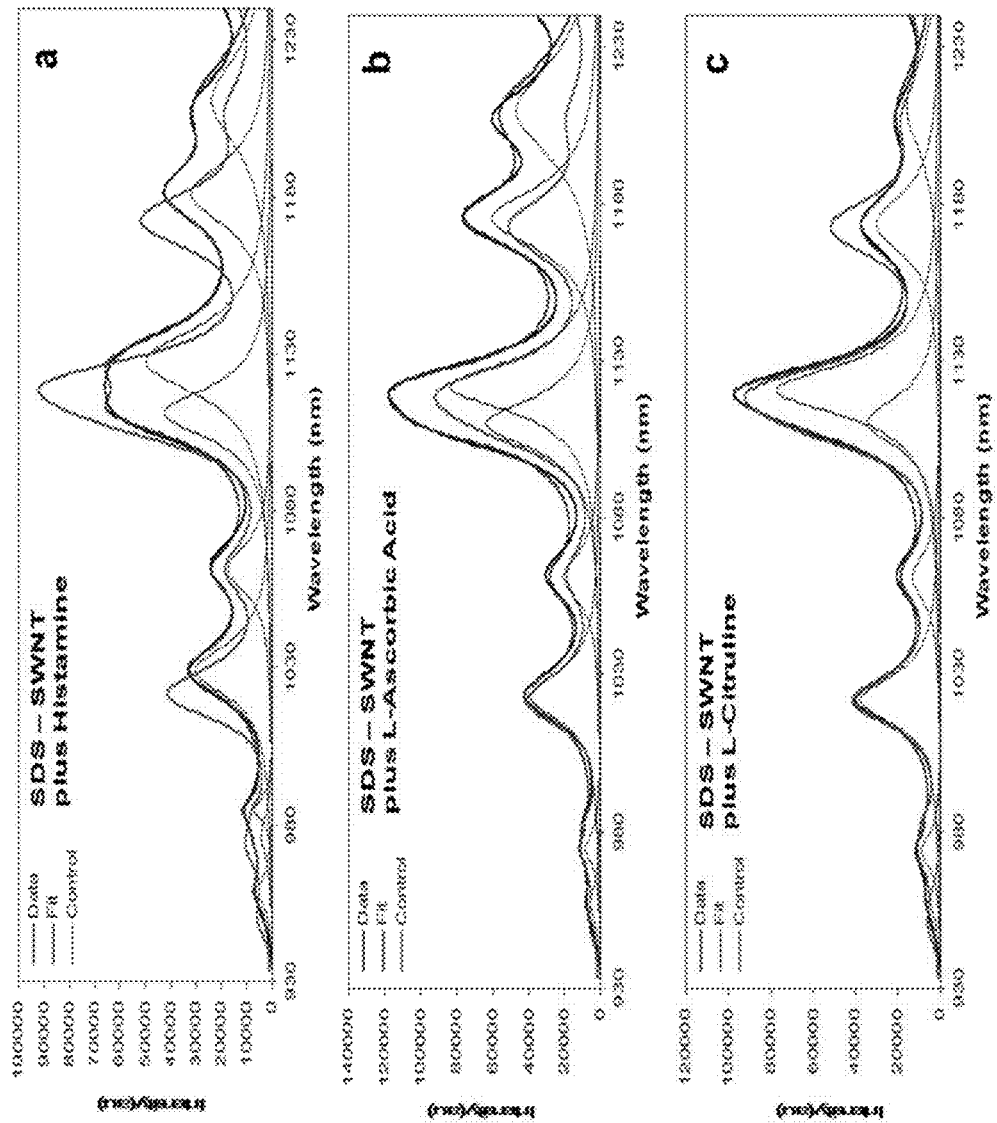
Figure 56:
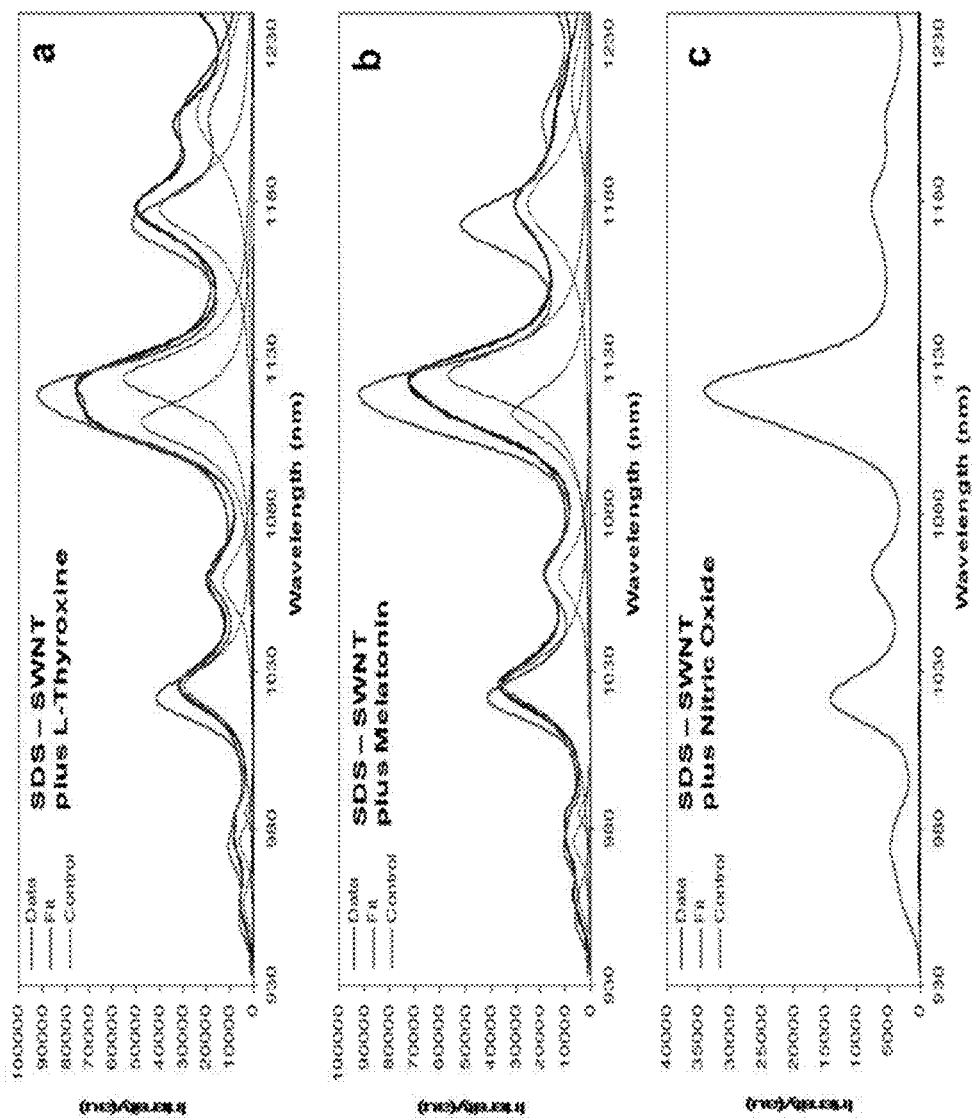
Figure 57:
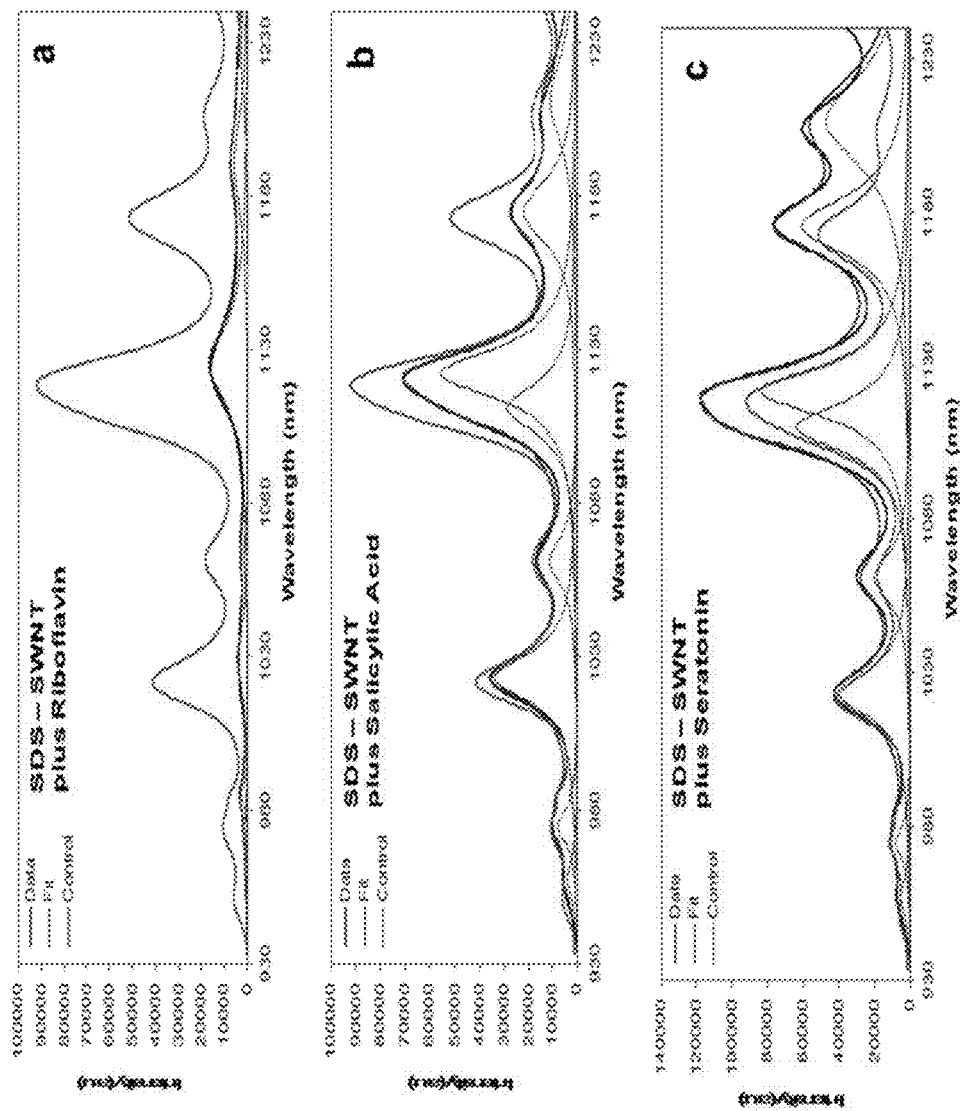

Specific Molecular Recognition:

Molecular recognition was observed from 44.6 wt % boronic acid-substituted phenoxy-dextran wrapped SWNTs (BA-PhO-Dex-SWNT). BA-PhO-Dex-SWNT showed a photoluminescence red-shift of 15 nm, maximum, upon addition of riboflavin (RF) (FIG. 6a). RF was the only analyte with this response (FIG. 4b). In comparison, SWNTs wrapped in unsubstituted phenoxy-dextran (PhO-Dex-SWNT) showed no shift in the presence of RF (FIGS. 4b, 6b). This response was similar to sodium cholate suspended SWNTs (FIG. 49).

Figure 4C:
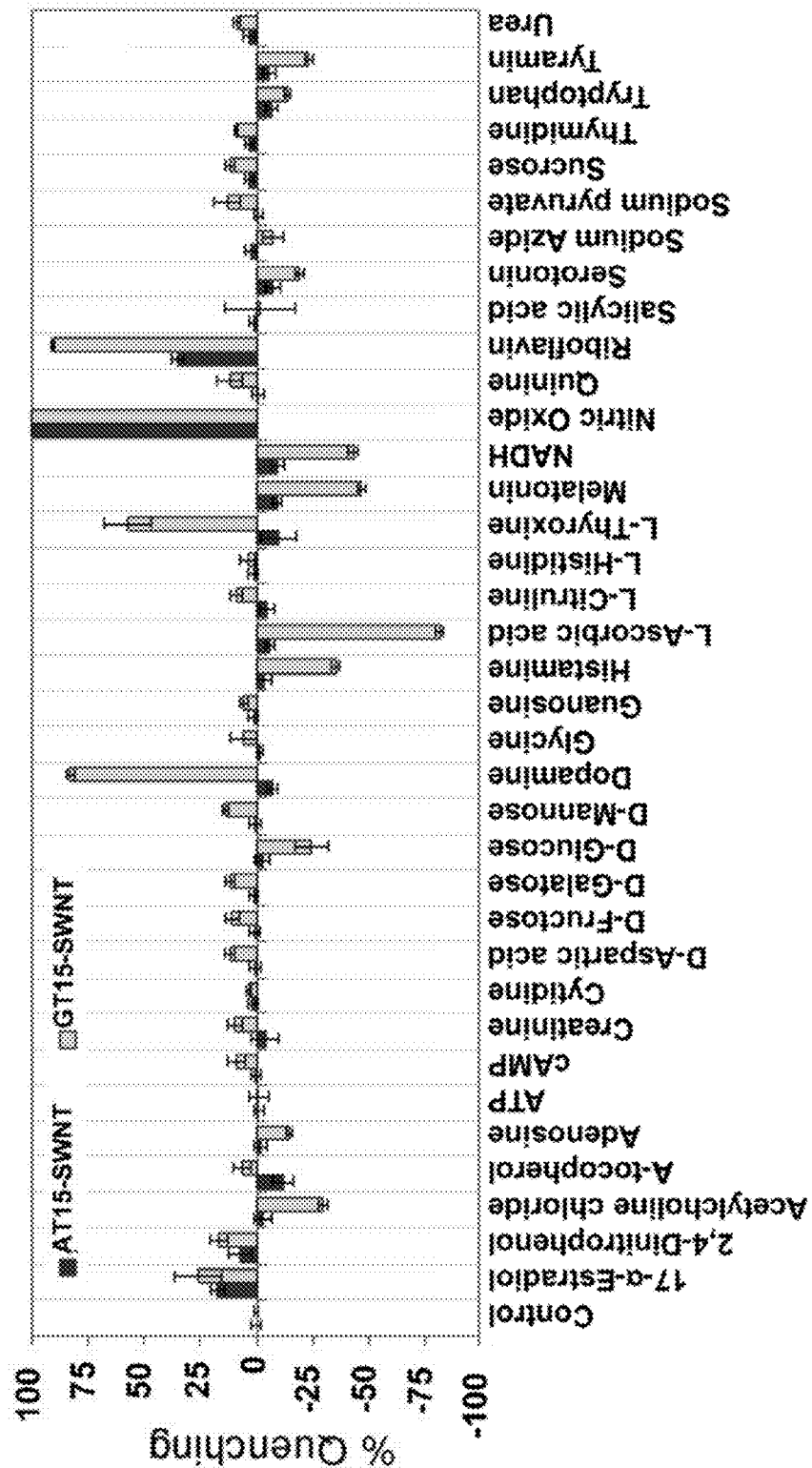

A second example was that $(AT)_{15}$ DNA oligonucleotide-encapsulated SWNTs ($AT_{15}$-SWNT) selectively recognized nitric oxide (NO) by complete photoluminescence quenching (FIG. 4c). Observation of this fingerprint was extremely uncommon, as the majority of polymer-SWNT complexes examined also exhibit photoluminescence quenching with multiple analytes, for example with dopamine and L-thyroxine. For example, $(GT)_{15}$ DNA-SWNTs (FIG. 4c) and polyvinyl alcohol SWNTs (PVA-SWNT, FIG. 21) exhibited complex, multi-analyte quenching. Although NO is a prominent quencher for many organic dyes and most polymer-SWNT constructs, PVA-SWNTs did not quench with NO exposure. Other quenching molecules, such as dopamine, were selectively excluded by the $(AT)_{15}$ DNA wrapping. Therefore, the polymer adsorbed phase appears to be central to molecular recognition.

Figure 4D:
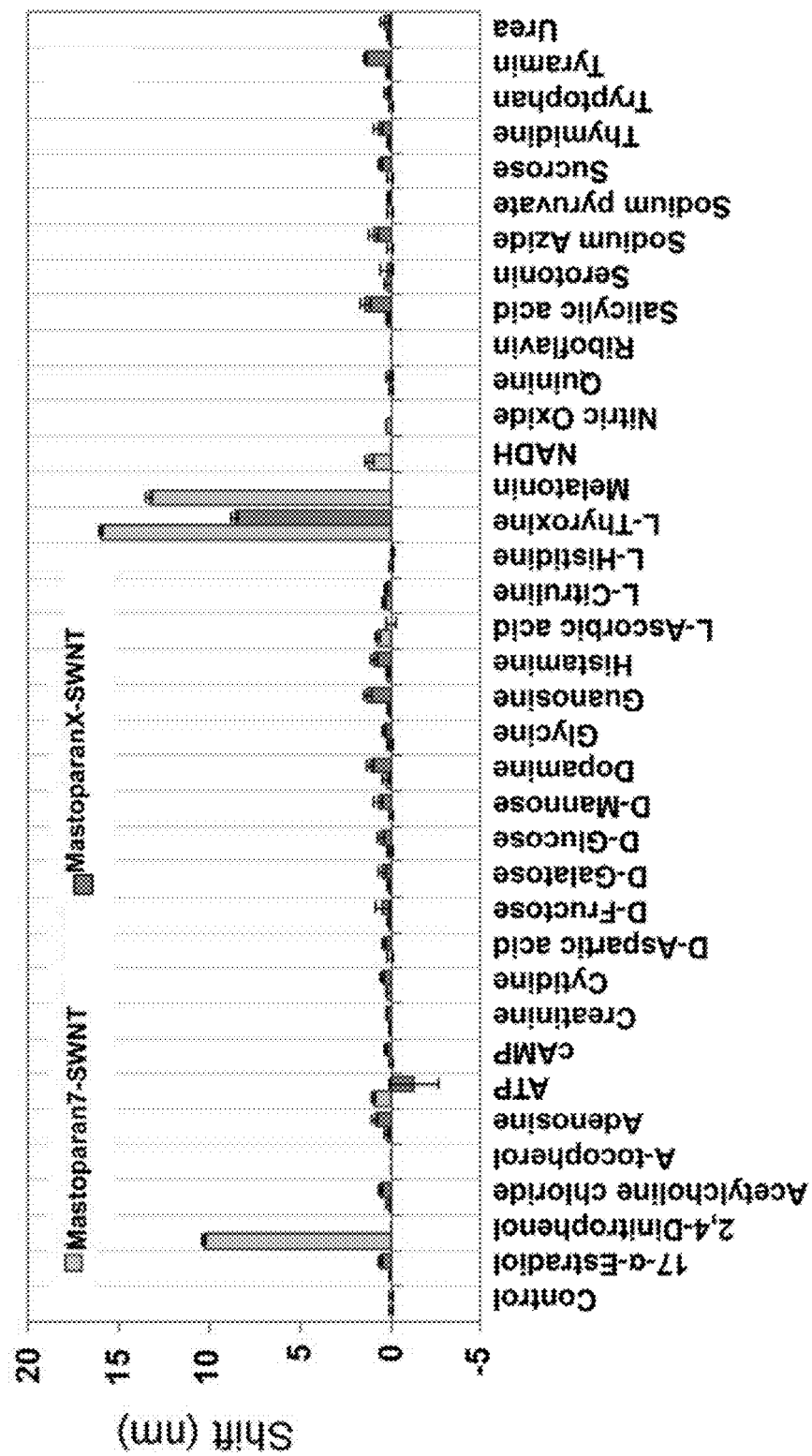
Figure 5A:
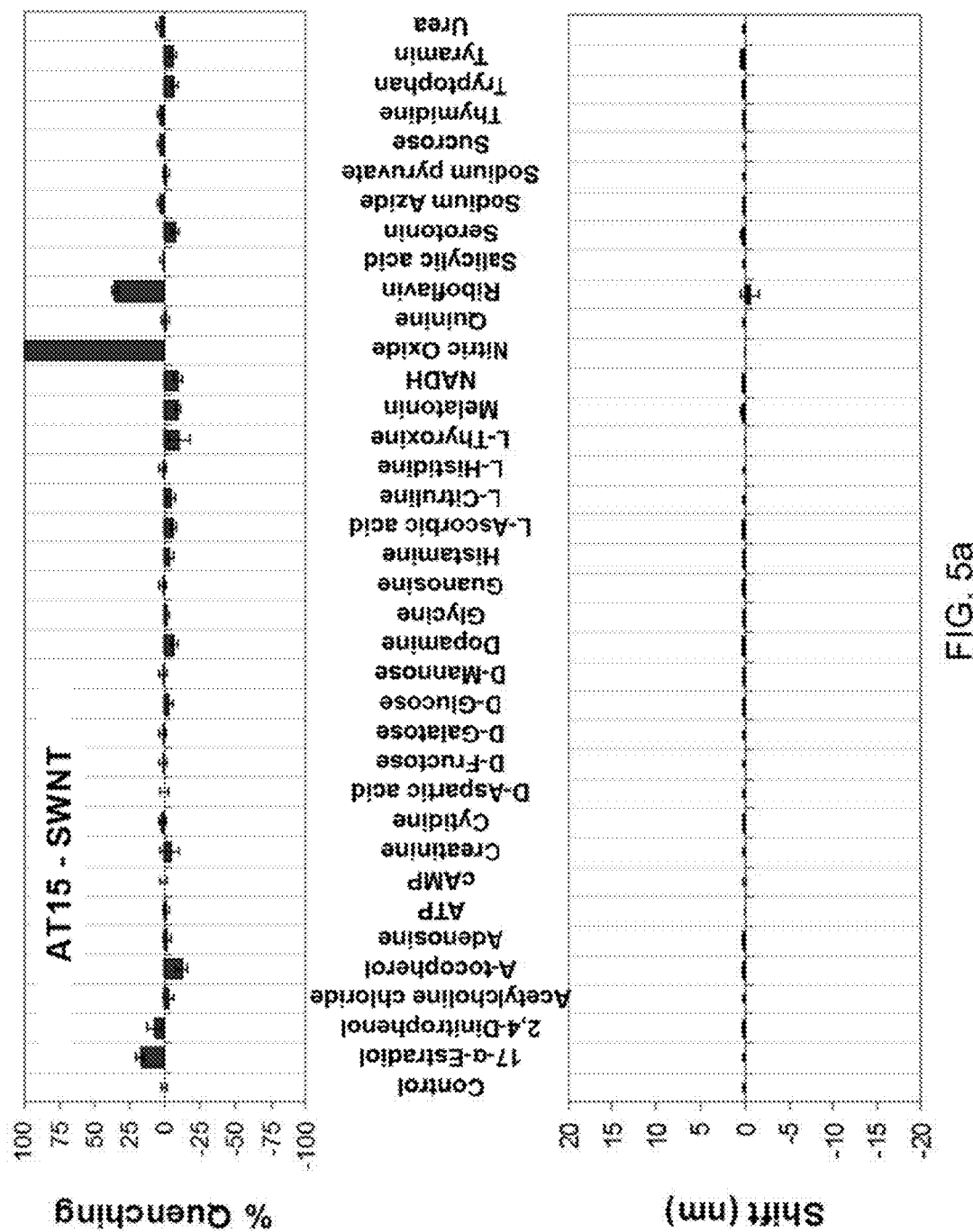
FIG. 5 includes plots demonstrating fluorescence quenching and emission maximum shift responses for the (7,5) nanotube from $AT_{15}$-SWNT and $GT_{15}$-SWNT after being queried with potential analytes.
Figure 5B:
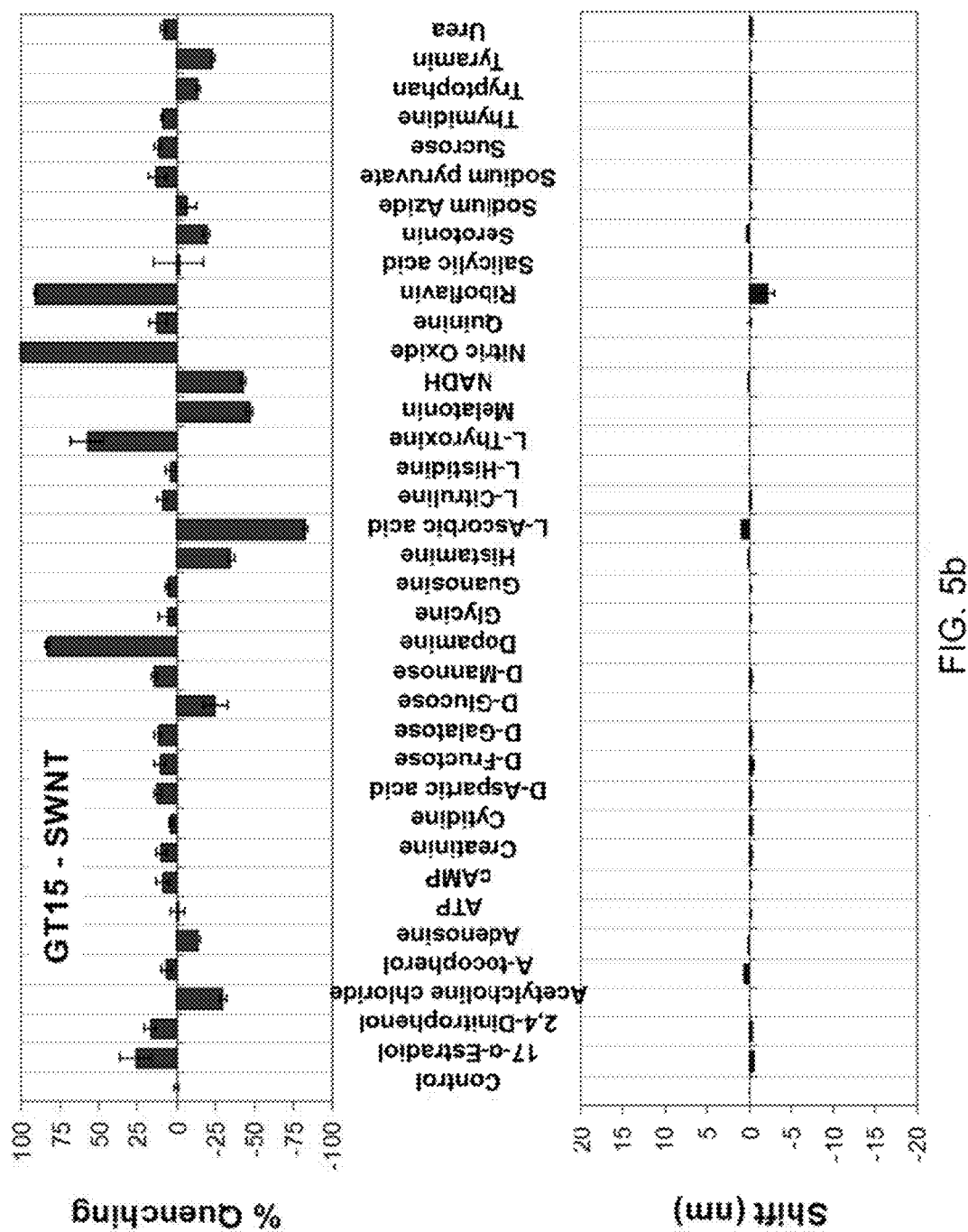

Finally, some peptides showed unusual fingerprints, which allowed for recognition of specific molecules. Mastoparan X-wrapped SWNTs (MastX-SWNT) red-shifted a maximum of 8 nm upon exposure to L-thyroxine, while Mastoparan 7-wrapped SWNTs (Mast7-SWNT) also responded to 2,4-dinitrophenol and melatonin (FIG. 4d).

Figure 36A:
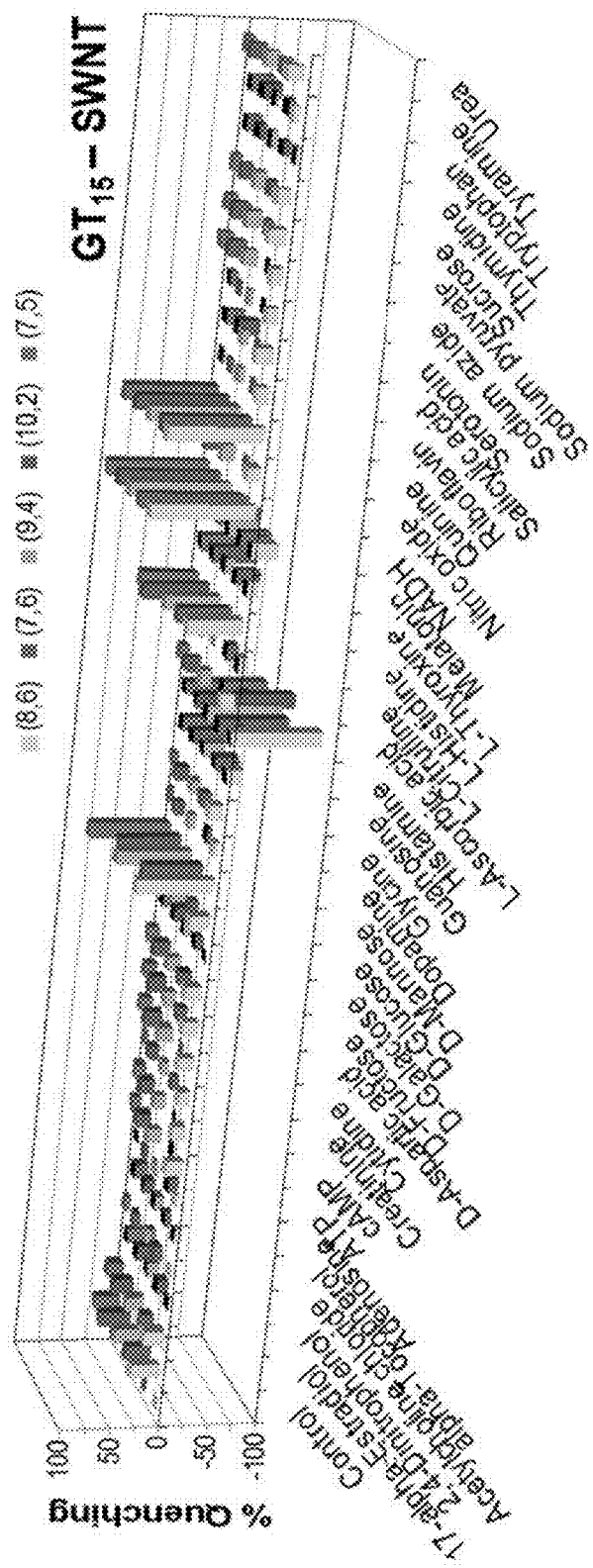
FIG. 36 includes two plots of the nanotube specific fluorescence response of $GT_{15}$-SWNT to different analytes.
Figure 36B:
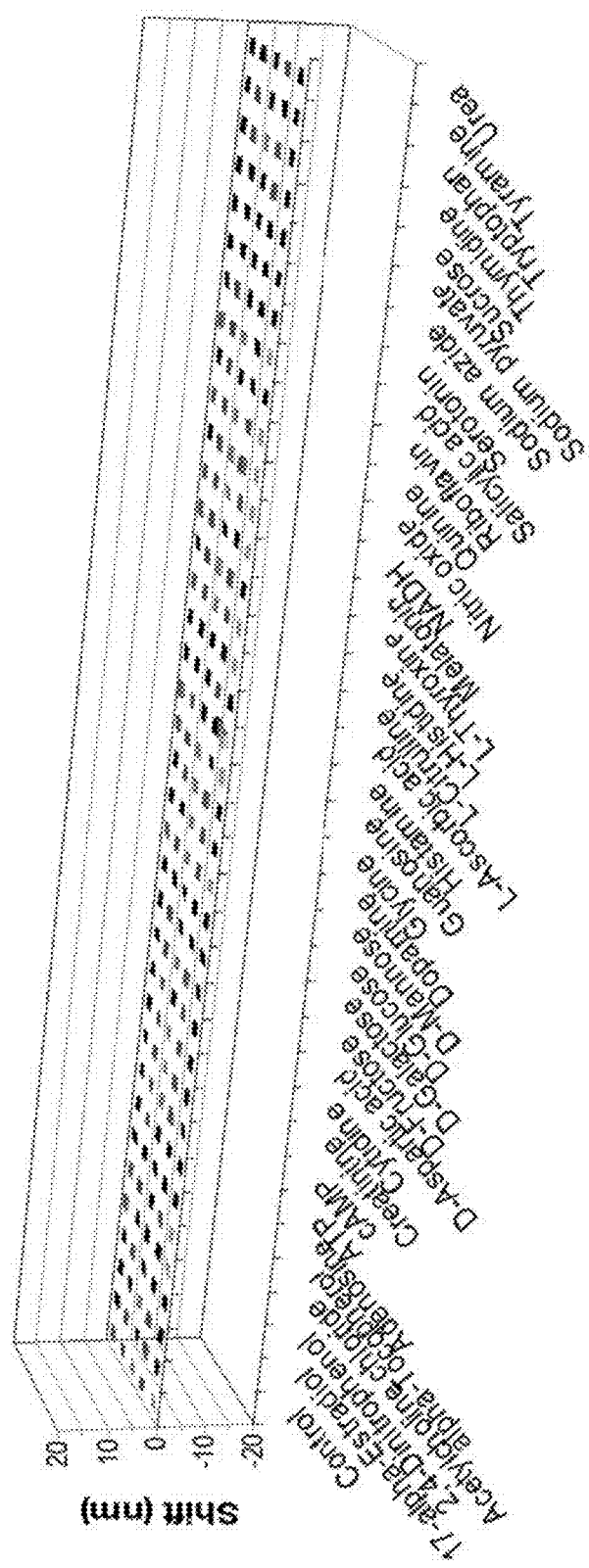
Figure 37:
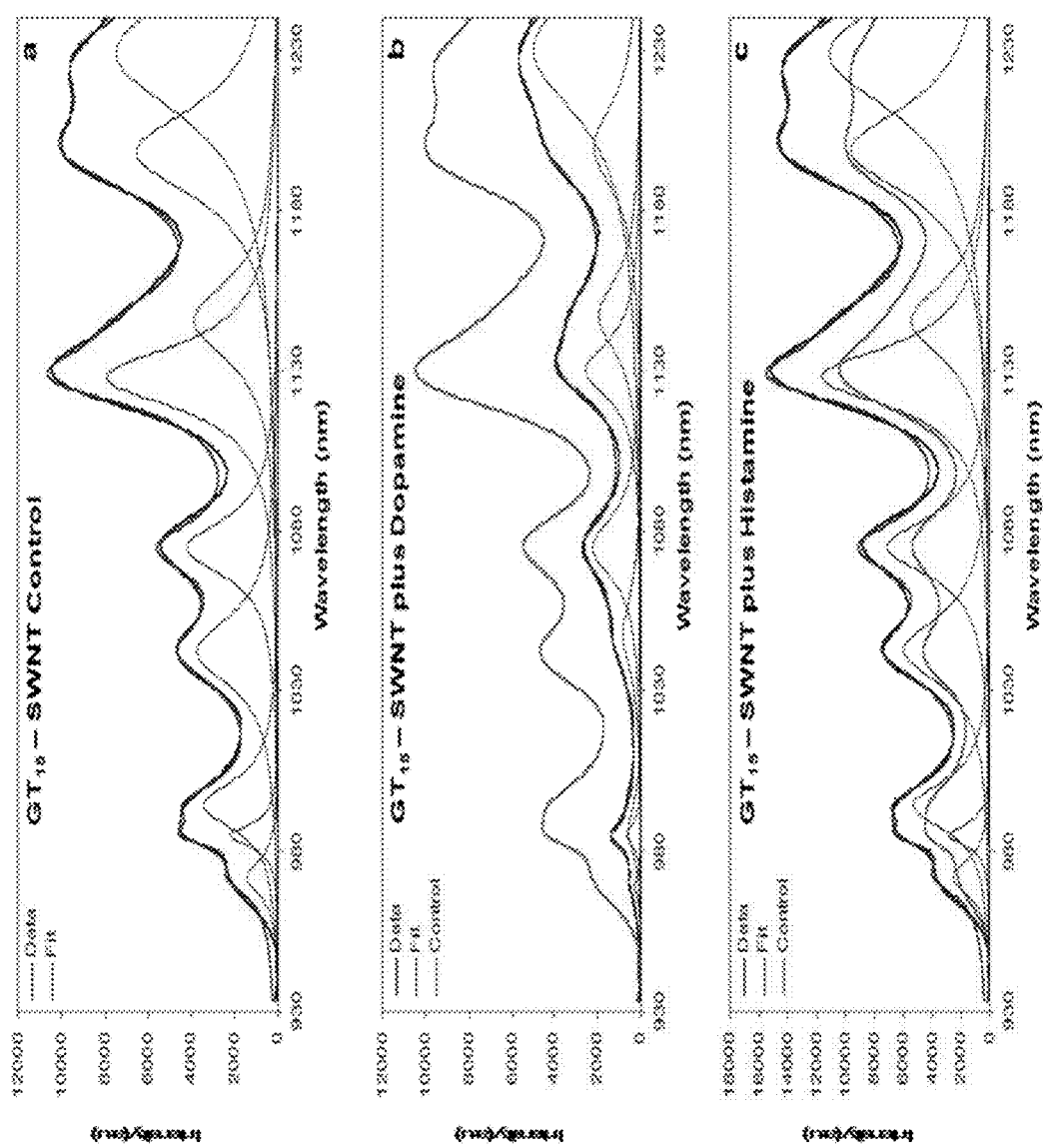
FIGS. 37-39 are deconvoluted spectra of fluorescence response of each nanotube species in $GT_{15}$-SWNT to 36 different analytes.
Figure 38:
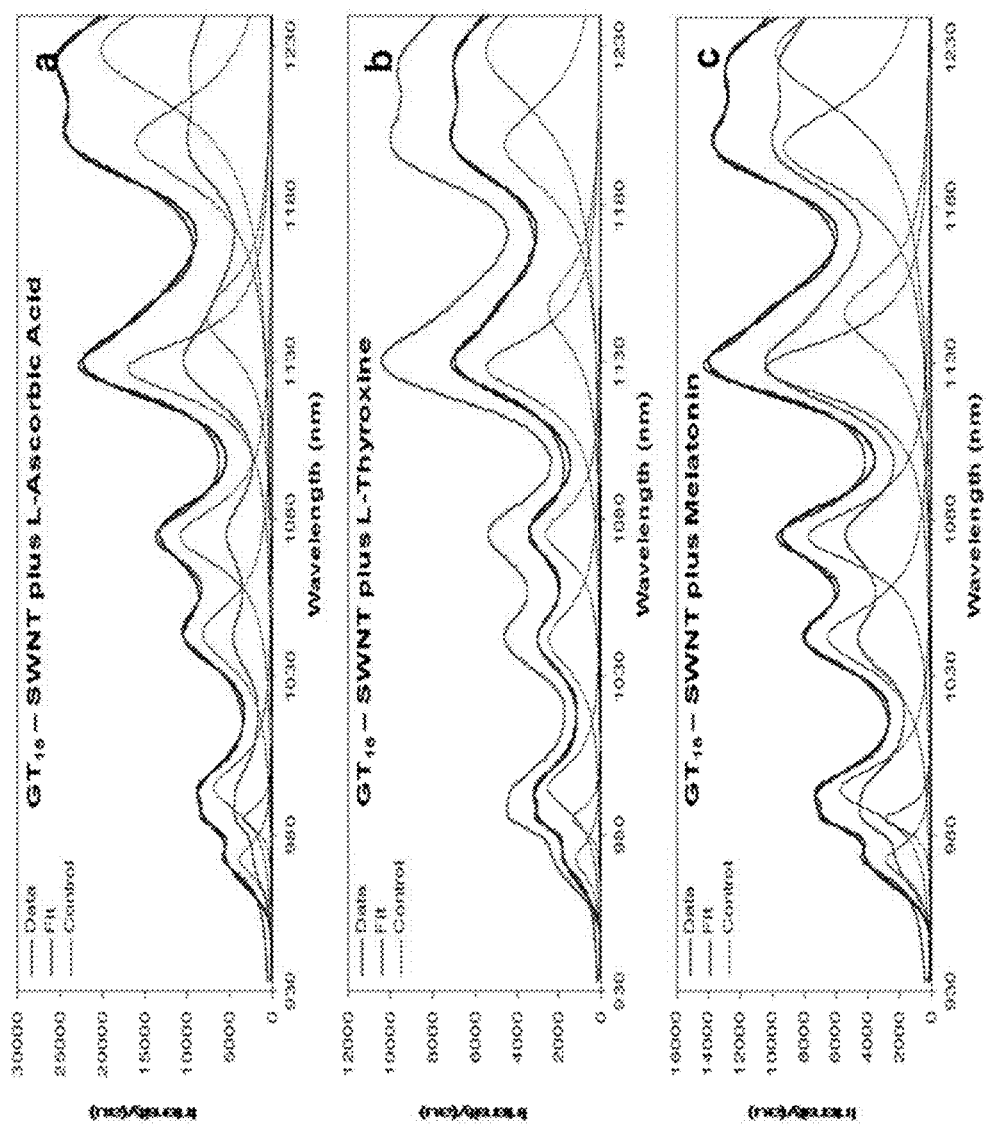
Figure 39:
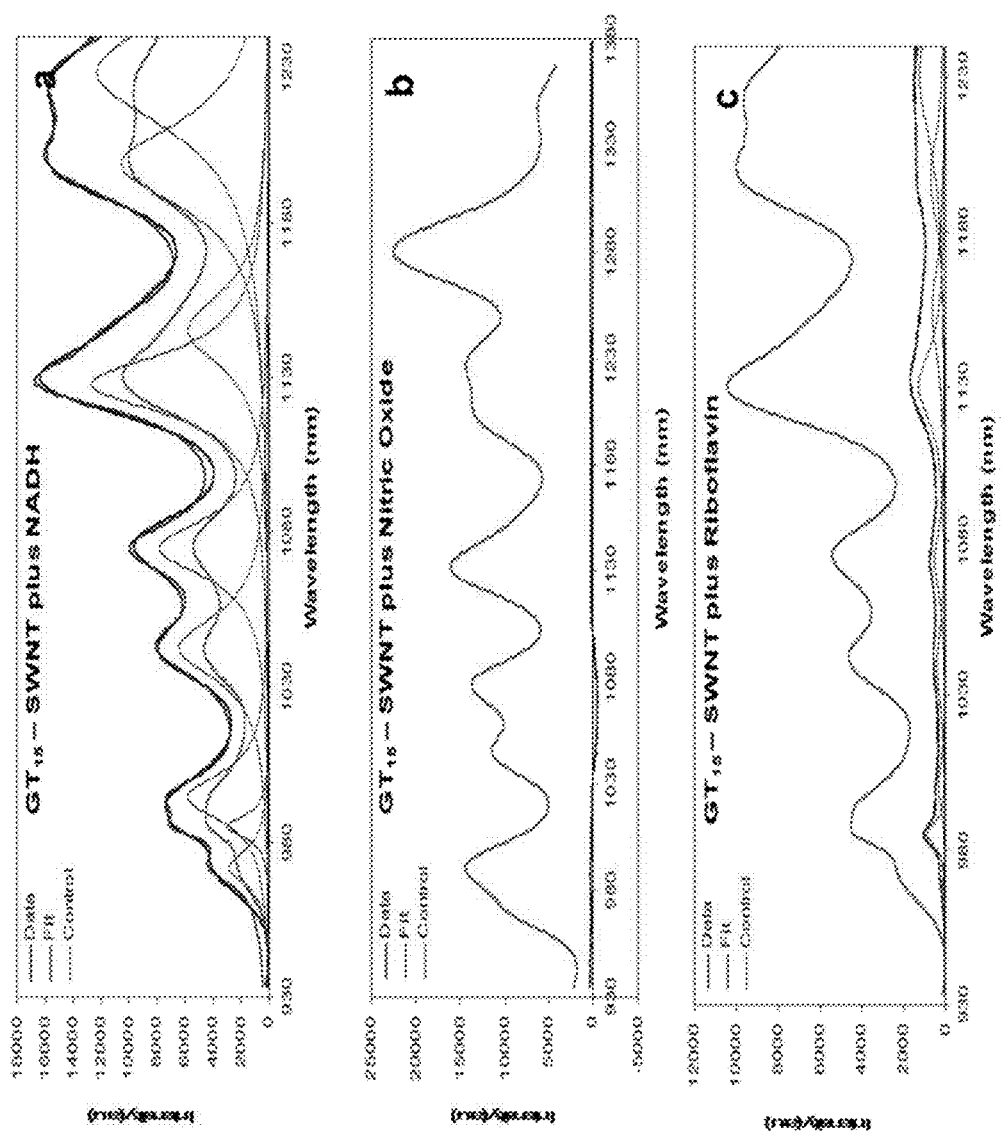
Figure 40A:
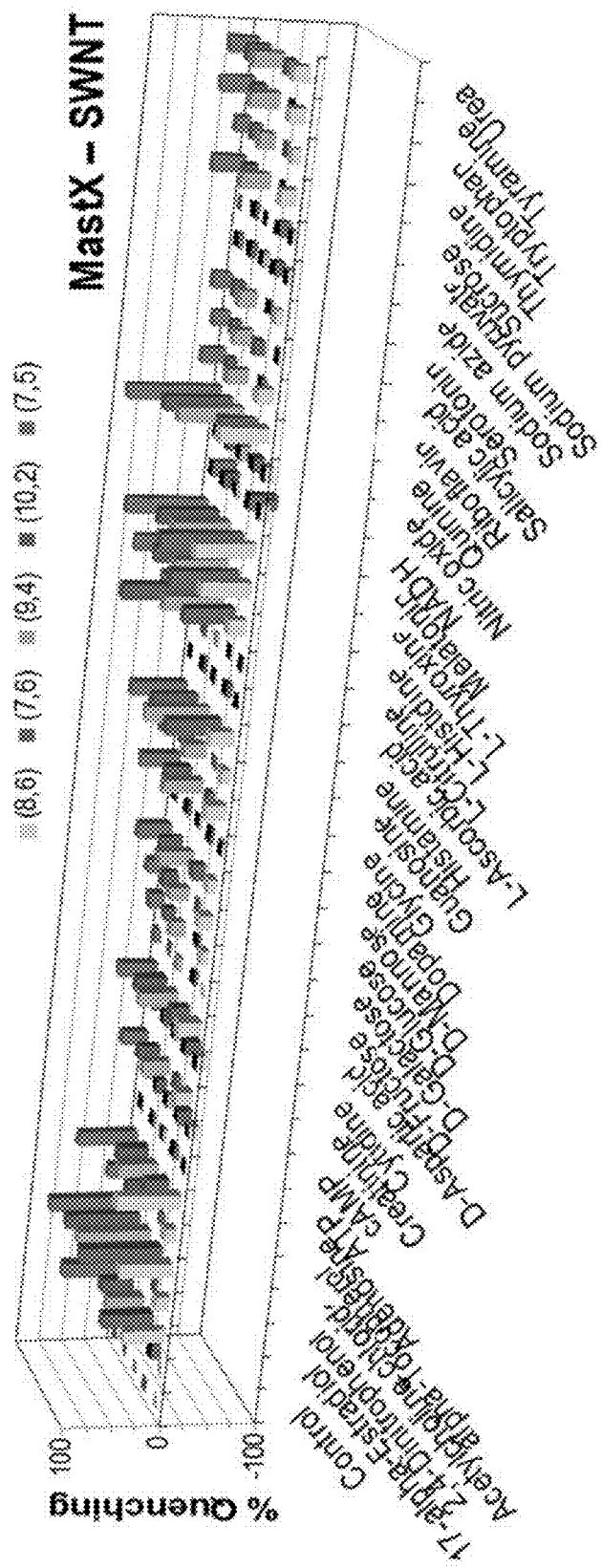
FIG. 40 includes two plots of the nanotube specific fluorescence response of MastX-SWNT to different analytes.
Figure 40B:
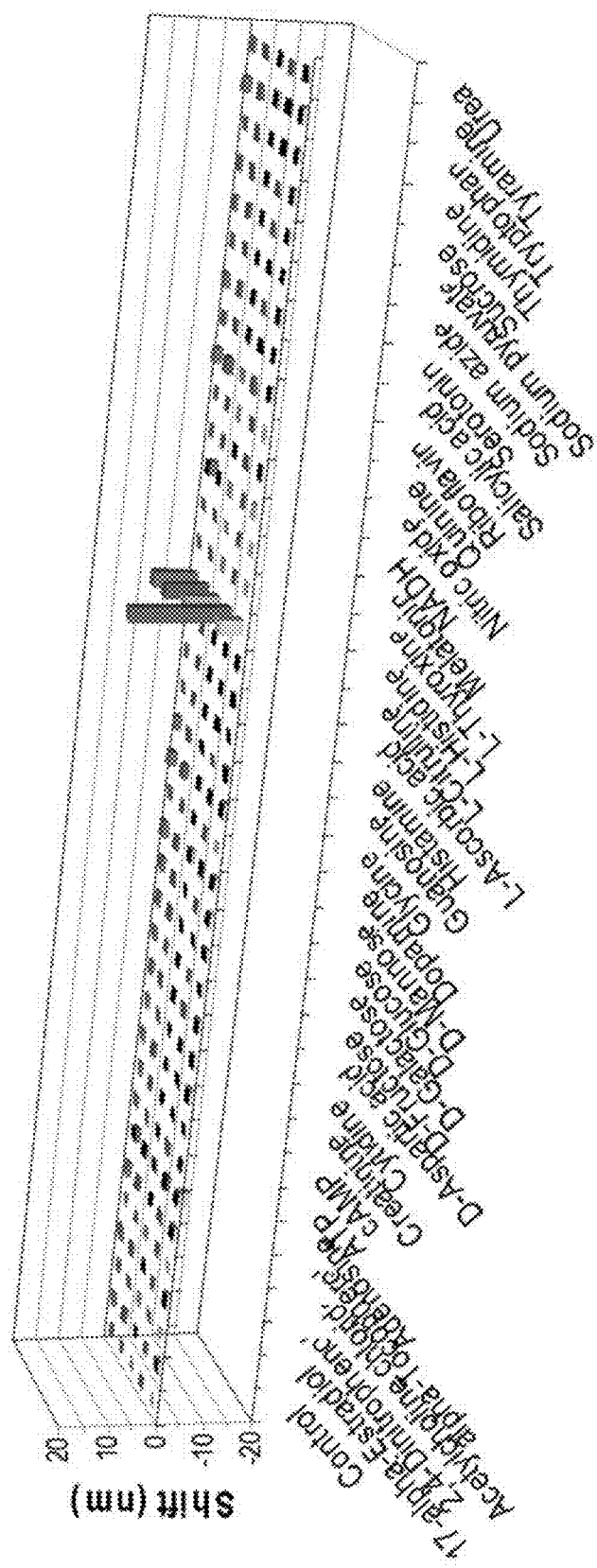
Figure 41:
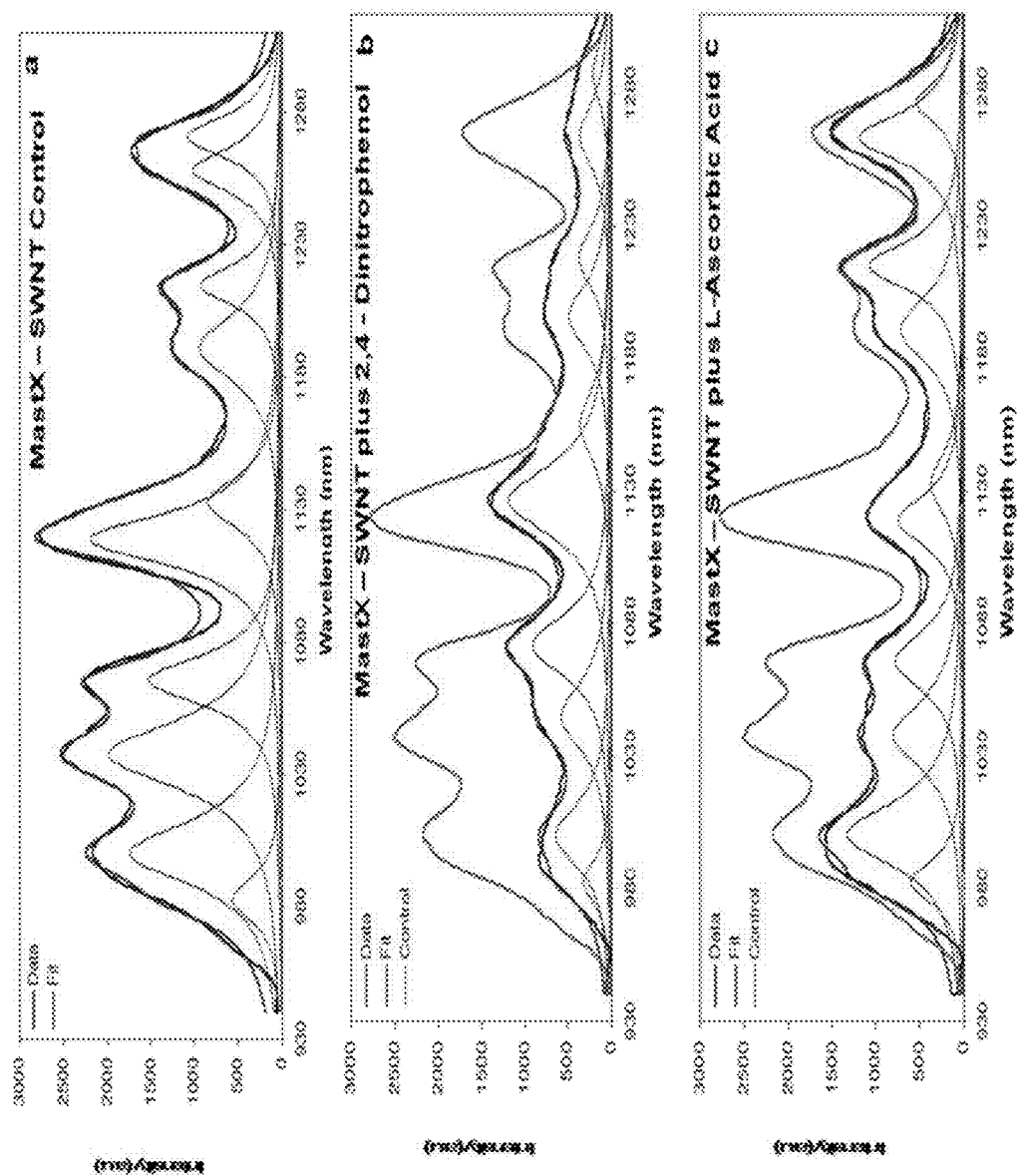
FIGS. 41-43 are deconvoluted spectra of fluorescence response of each nanotube species in MastX-SWNT to different analytes.
Figure 42:
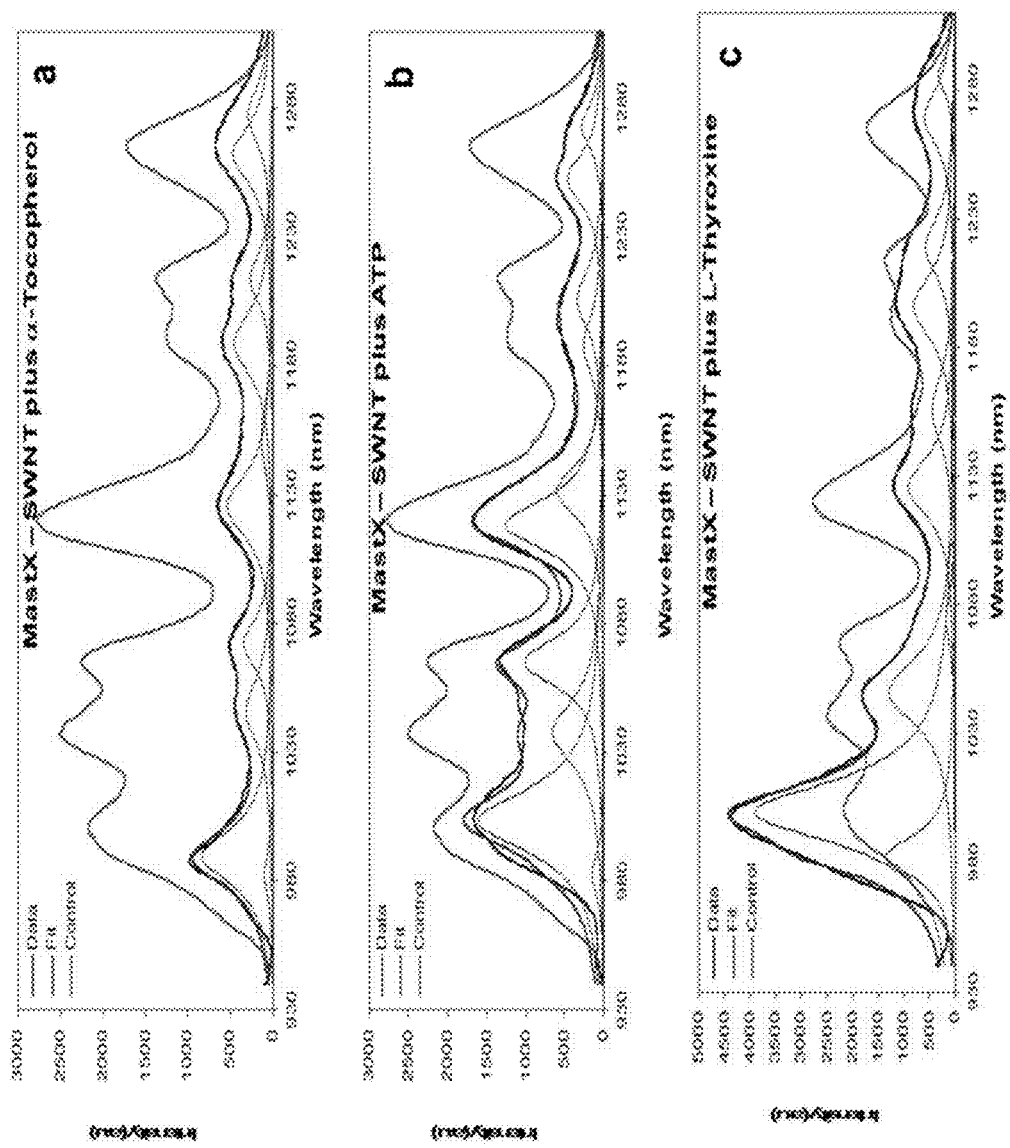
Figure 43:
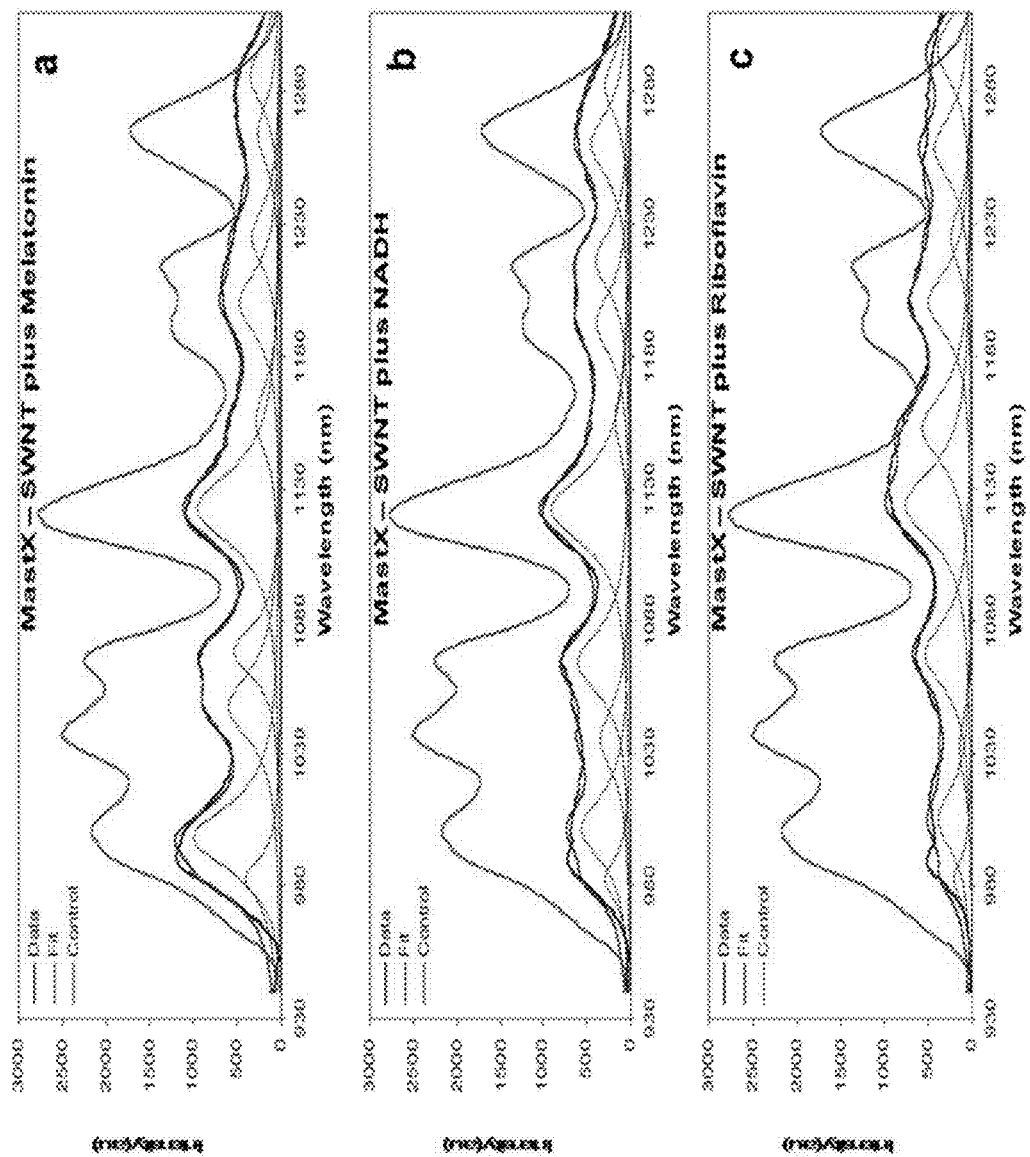
Figure 44A:
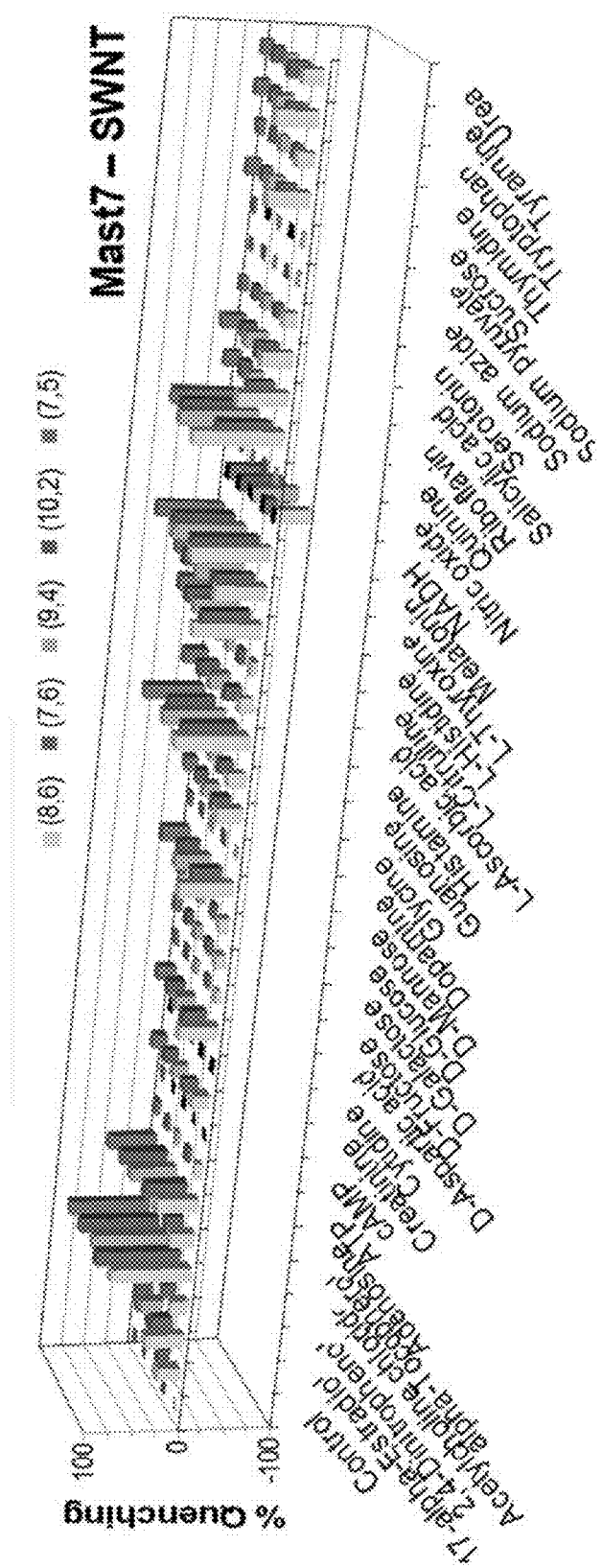
FIG. 44 includes two plots of the nanotube specific fluorescence response of Mast7-SWNT to different analytes.
Figure 44B:
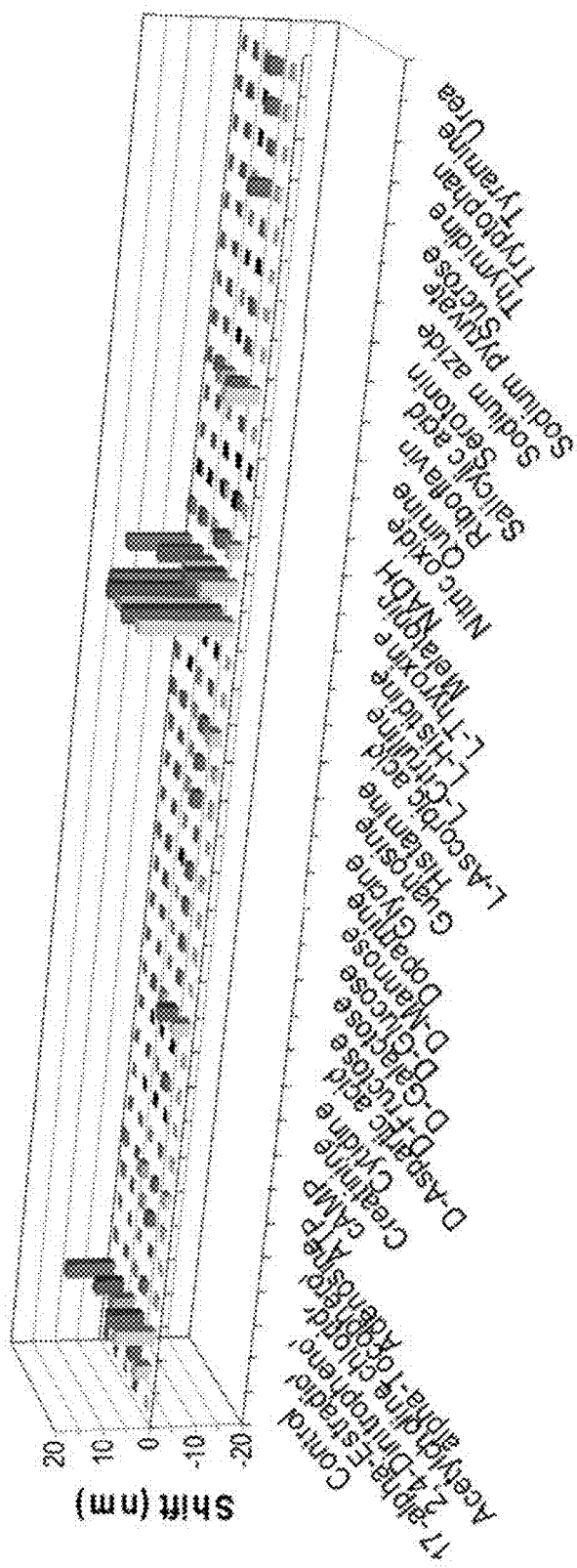
Figure 45:
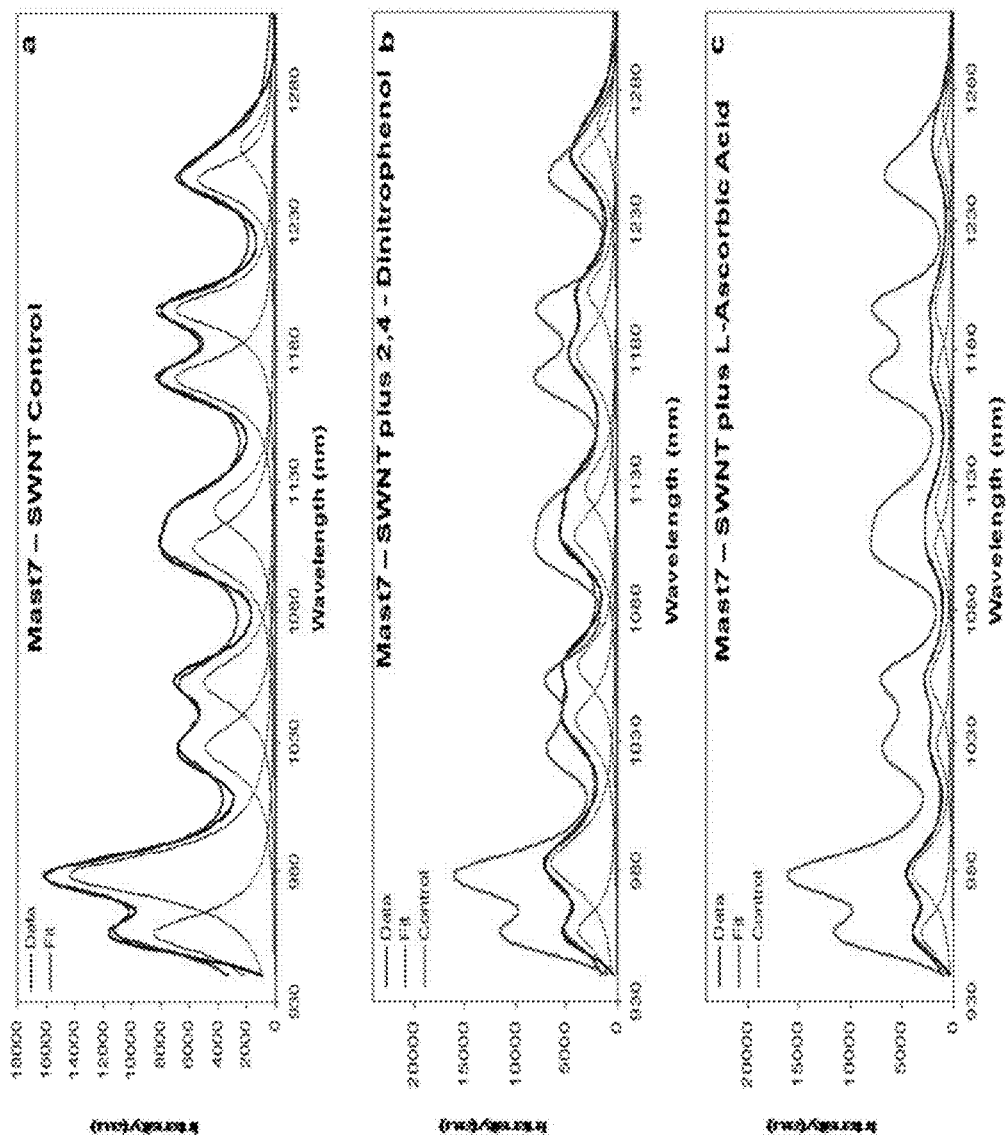
FIGS. 45-48 are deconvoluted spectra of fluorescence response of each nanotube species in Mast7-SWNT to different analytes.
Figure 46:
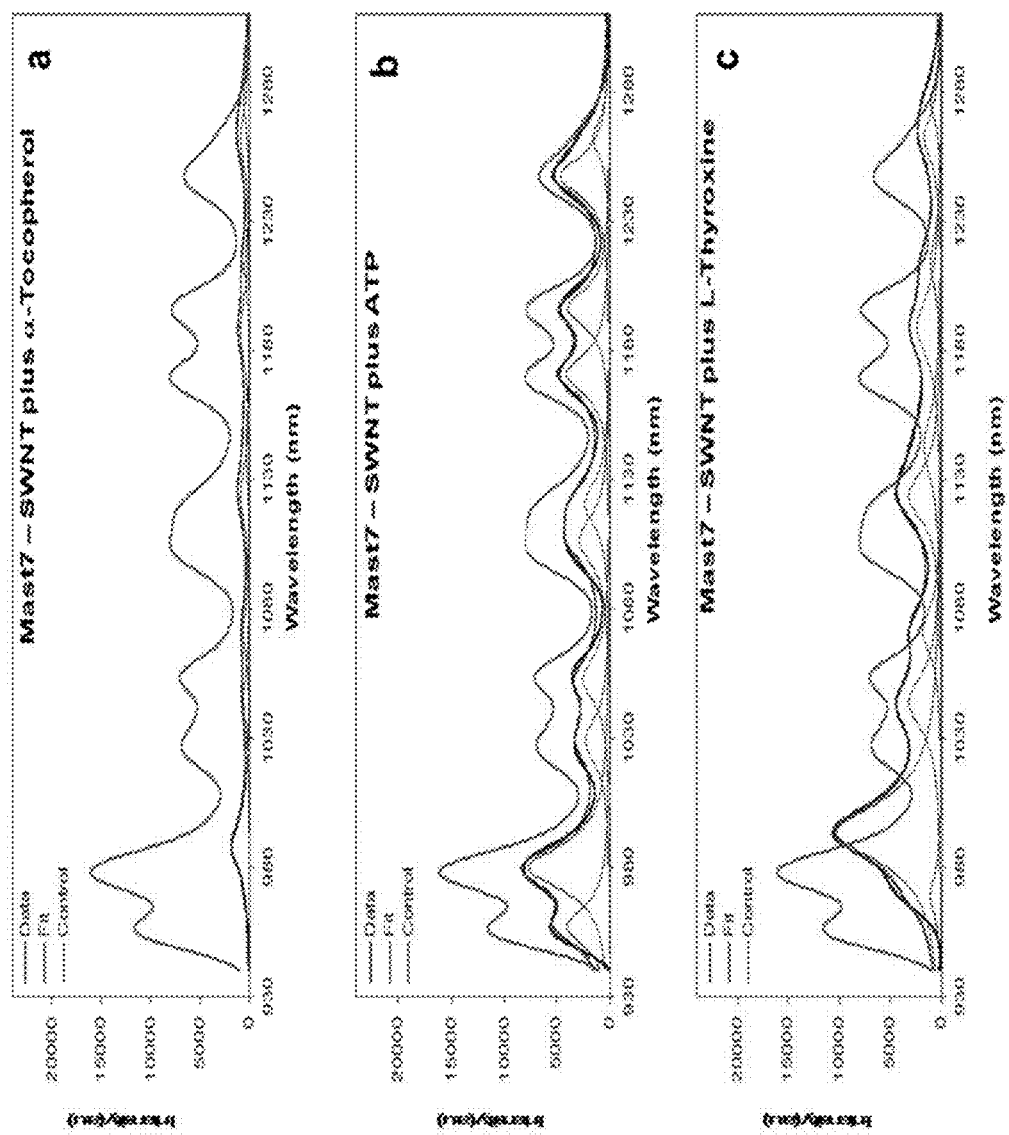
Figure 47:
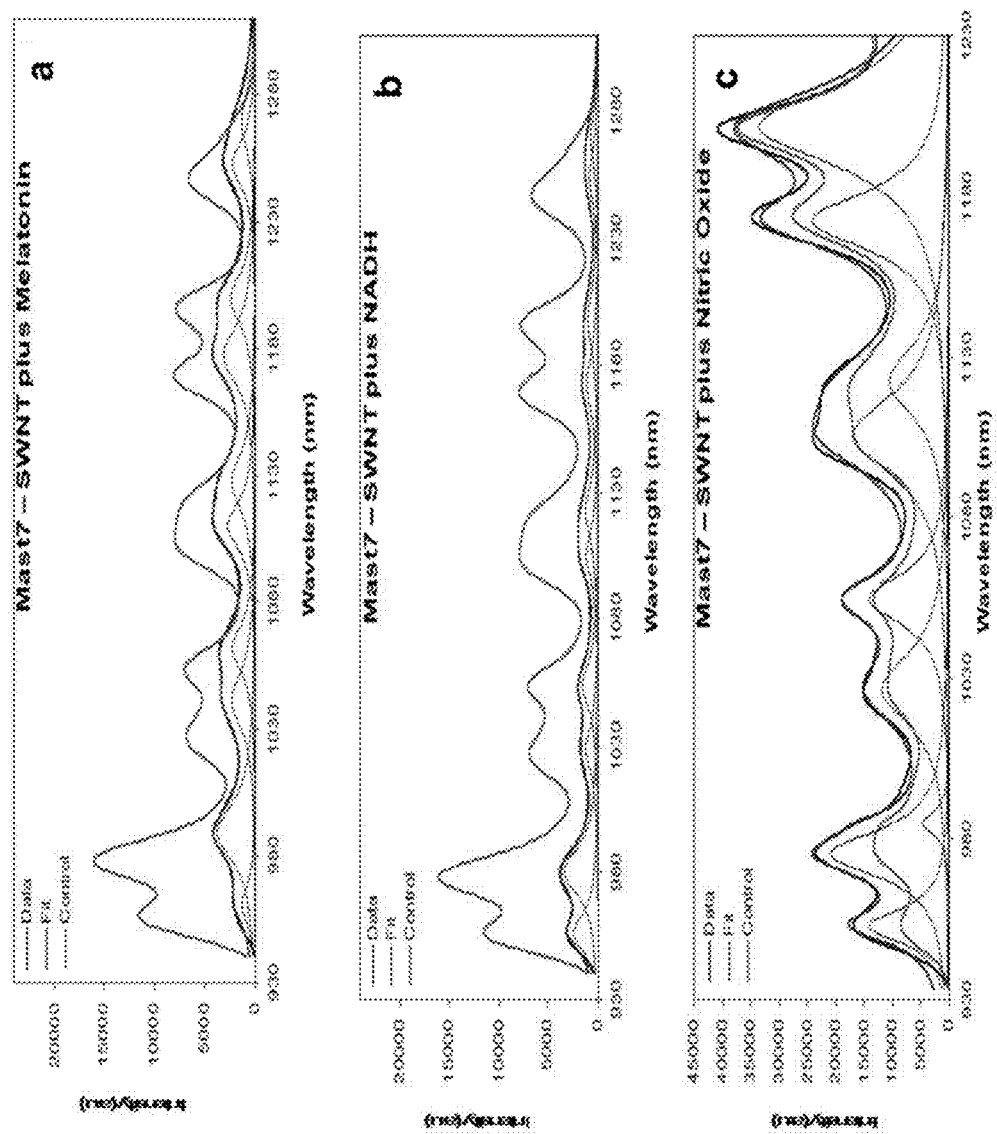
Figure 48:
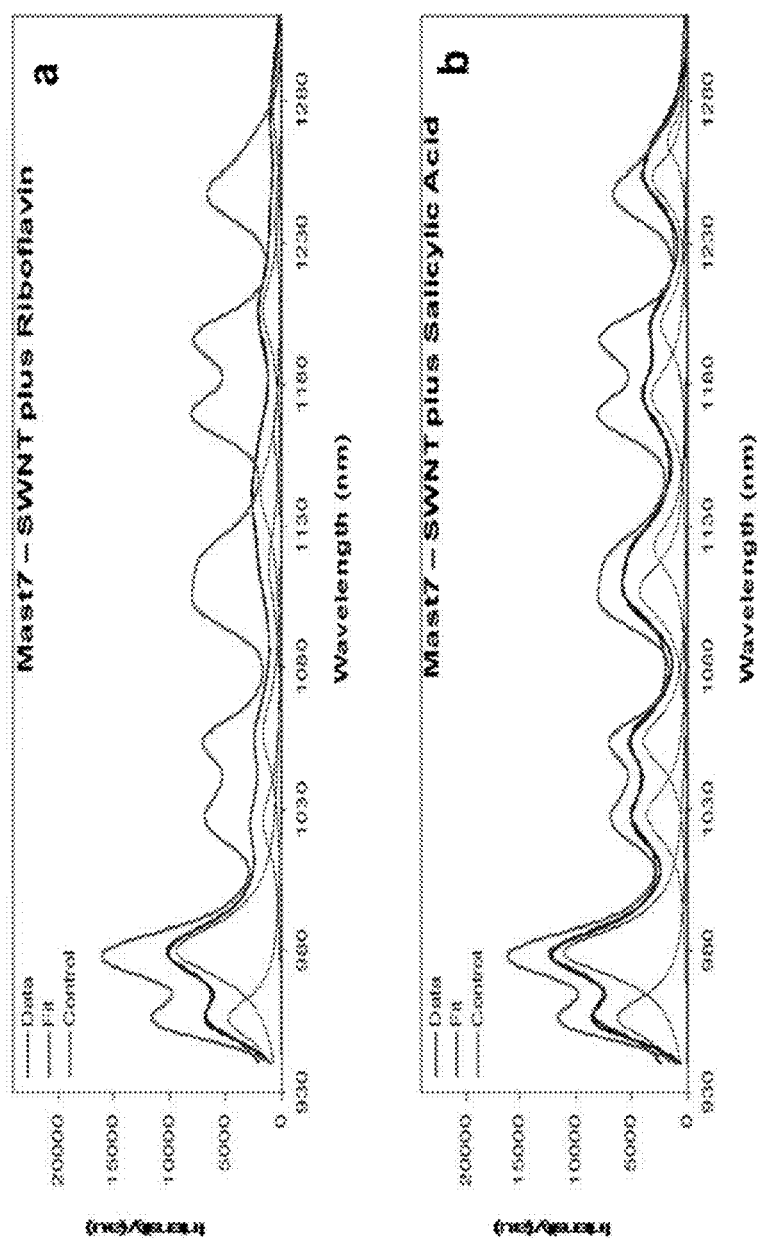

Redox Potential Differences:

One possible explanation for such high selectivity is redox potential differences between the analytes and the SWNTs, with the latter modified by the polymer. For example, $GT_{15}$-SWNT photoluminescence was quenched by NO but increased with melatonin (FIG. 4c and FIGS. 36-37). The former might be partially explained by the reduction potential of NO (−0.5 V NHE) being larger than the valence band of SWNTs (−1 to −0.5 V NHE). (O'Connell, M., et al., Chiral selectivity in the charge-transfer bleaching of single-walled carbon-nanotube spectra. *Nature Materials* 4, 412-418 (2005); Bartberger, M., et al., The reduction potential of nitric oxide (NO) and its importance to NO biochemistry. *Proceedings of the National Academy of Sciences of the United States of America* 99, 10958 (2002), which are incorporated by reference in their entirety). However, the conduction band of SWNTs (0.1 to 0.7 versus NHE) and melatonin oxidation potential (0.95 V versus NHE) are unable to explain the latter. (O'Connell, M., et al., (2005); Mahal, H., et al., Antioxidant properties of melatonin: a pulse radiolysis study. *Free Radical Biology and Medicine* 26, 557-565 (1999), which is incorporated by reference in its entirety). Hence, redox interactions alone do not seem to describe the molecular recognition.

Chirality Dependence:

Many polymers can adsorb and recognize particular SWNT chiralities. This concept has been utilized for separation techniques. (Nish, A., et al., Highly selective dispersion of single-walled carbon nanotubes using aromatic polymers. Nature Nanotechnology 2, 640-646 (2007); Tu, X., et al., DNA sequence motifs for structure-specific recognition and separation of carbon nanotubes. Nature 460, 250-253 (2009); Arnold, M. S., et al., Enrichment of Single-Walled Carbon Nanotubes by Diameter in Density Gradients. Nano Lett. 5, 713-718 (2005); Ju, S. Y., et al., Selection of Carbon Nanotubes with Specific Chiralities using Helical Assemblies of Flamin Mononucleotide. Nature Nanotechnology 3, 356-362 (2008), which are incorporated by reference in their entirety). One possible explanation is that the polymer occupies a specific configuration on the target chirality that can enable manipulation of the species. Experimental efforts, as well as molecular simulation efforts, suggest that specific phases could form on the surface of the SWNT when certain molecules adsorb. (Nish, A., et al., (2007); Zheng, M., et al., DNA-assisted dispersion and separation of carbon nanotubes. Nature Materials 2, 338-342 (2003); Tsyboulski, D. et al., Self-Assembling Peptide Coatings Designed for Highly Luminescent Suspension of Single-Walled Carbon Nanotubes. J. Am. Chem. Soc 130, 17134-17140 (2008); Chen, F., et al., Toward the extraction of single species of single-walled carbon nanotubes using fluorene-based polymers. Nano Lett 7, 3013-3017 (2007), which are incorporated by reference in their entirety).

Figure 7A:
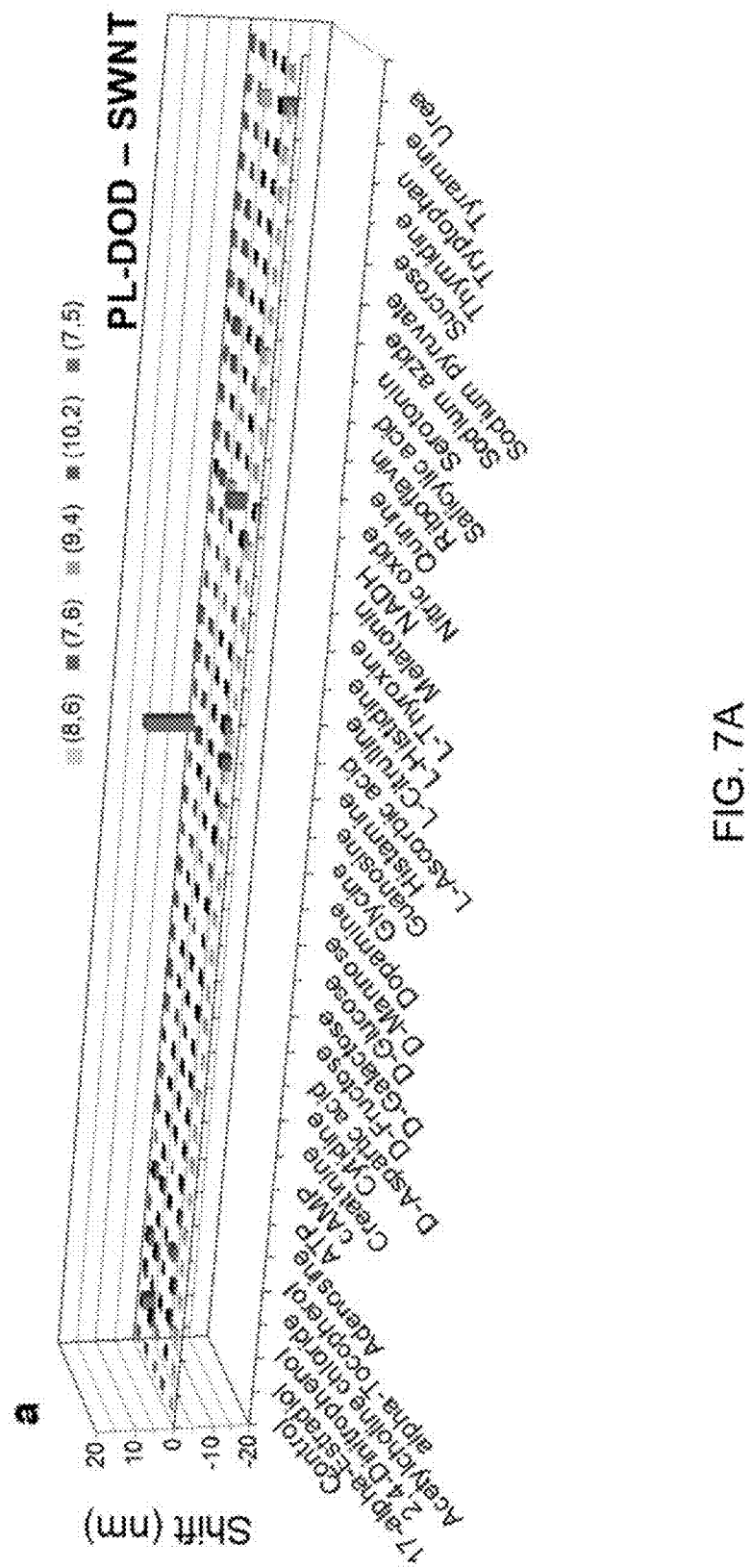
FIG. 7 includes two plots of the nanotube specific fluorescence response of polymer wrapped SWNTs to different analytes.
Figure 7B:
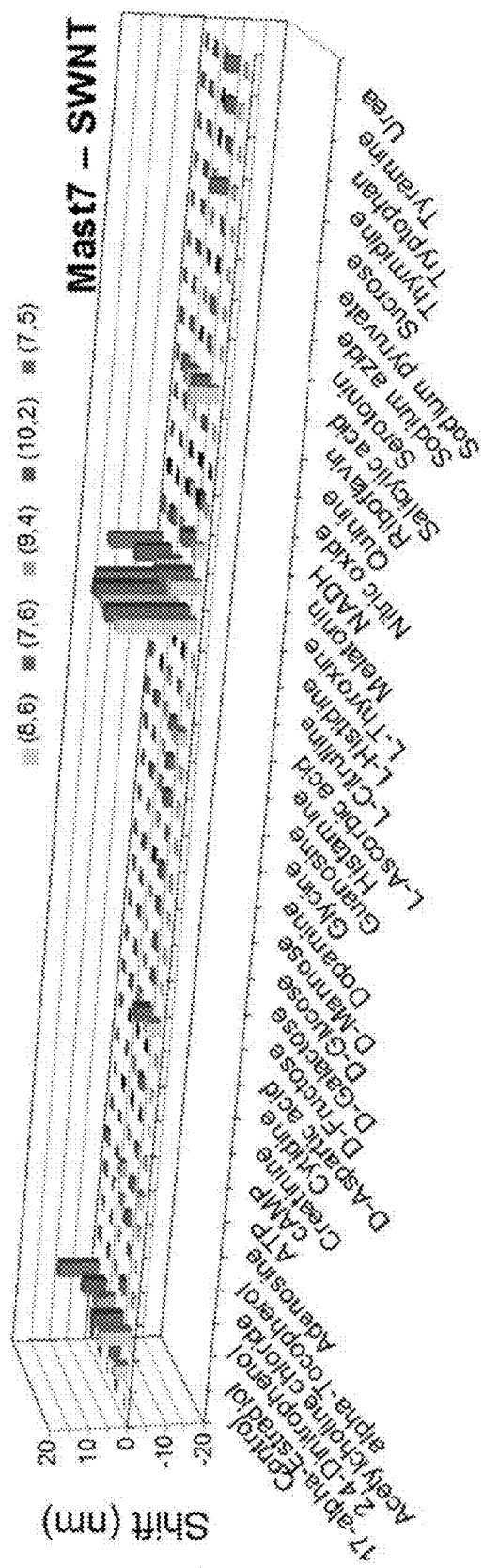

Similarly, recognition of an external analyte might be chirality dependent. Only the (7, 5) species of 1,2-dipalmitoyl-sn-glycero-3-phosphoethanolamine-N-(lauroyl) suspended SWNTs (PL-DOD-SWNT) showed a 12 nm red-shift in emission energy in response to histamine, whereas other chiralities did not respond (FIG. 7a). In contrast, an almost uniform emission shift was observed for all chiralities after exposure to L-thyroxine on Mast7-SWNTs (FIG. 7b). Salicylic acid recognition with the same construct favored larger diameter SWNTs (FIG. 7b).

Figure 8A:
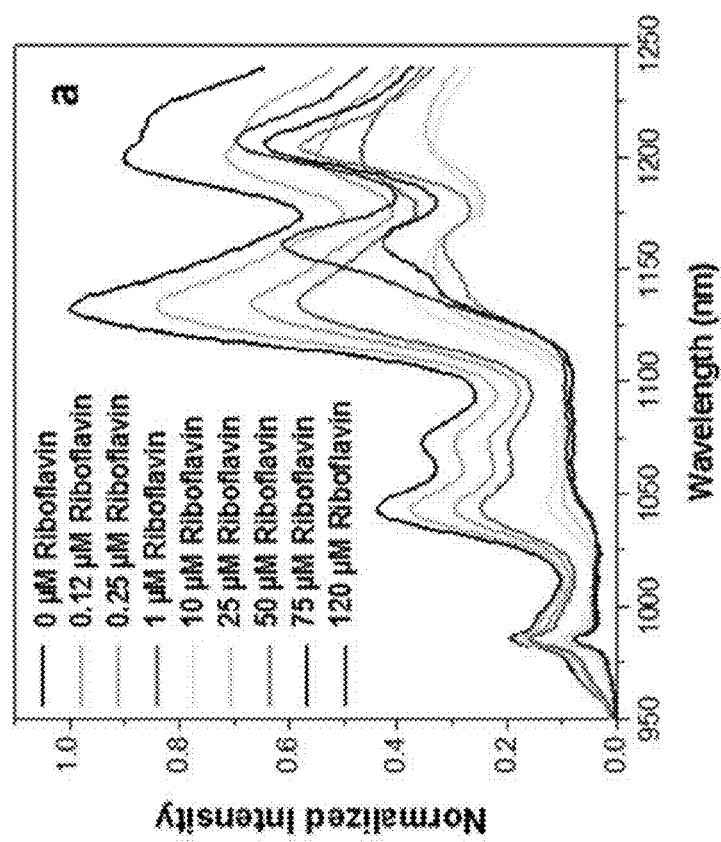
FIG. 8 illustrates the tunable $K_a$ of BA-PhO-Dex-SWNTs to riboflavin.
Figure 16:
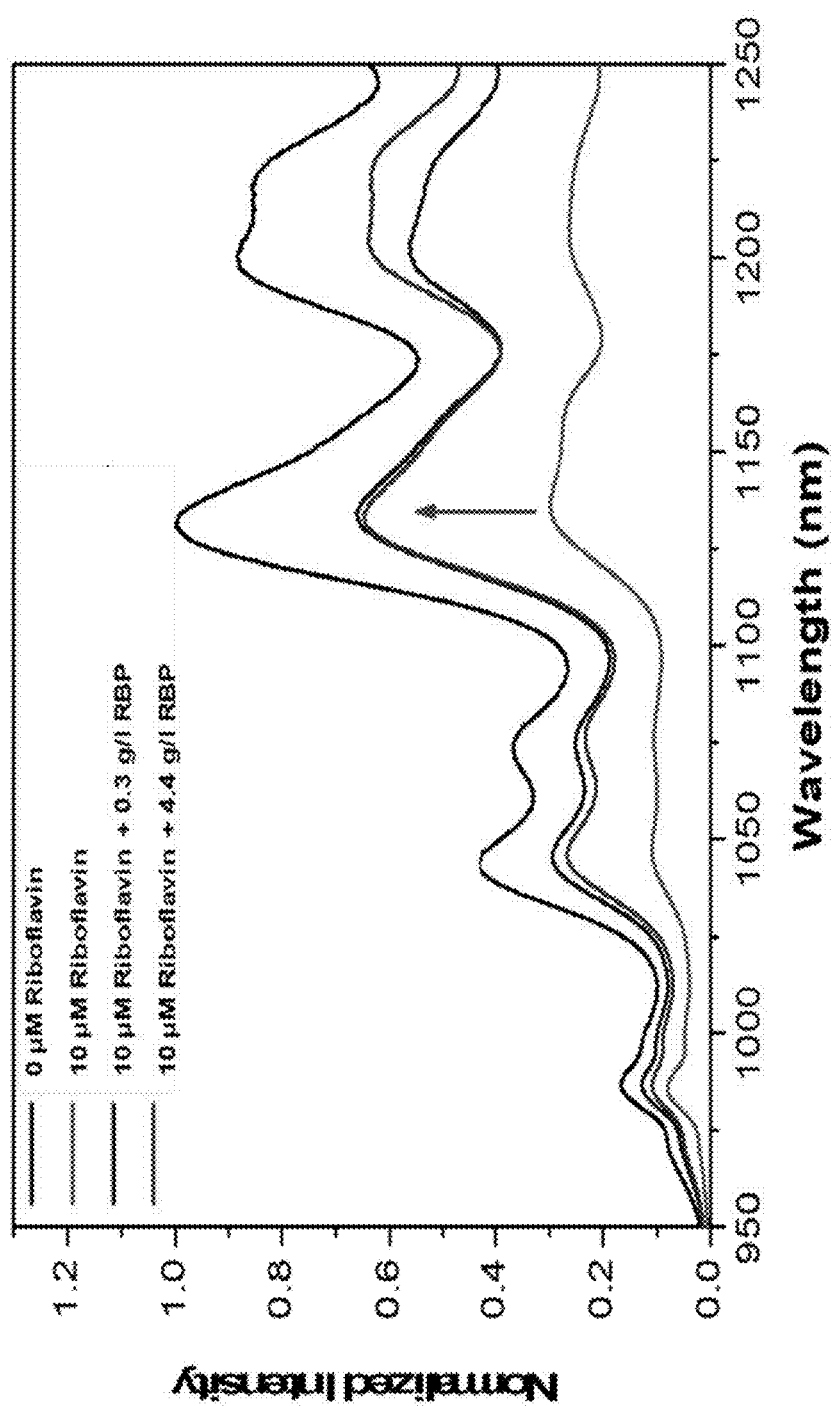
FIG. 16 is a plot demonstrating reversible quenching of BA-PhO-Dex-SWNT photoluminescence in response to riboflavin.
Figure 17A:
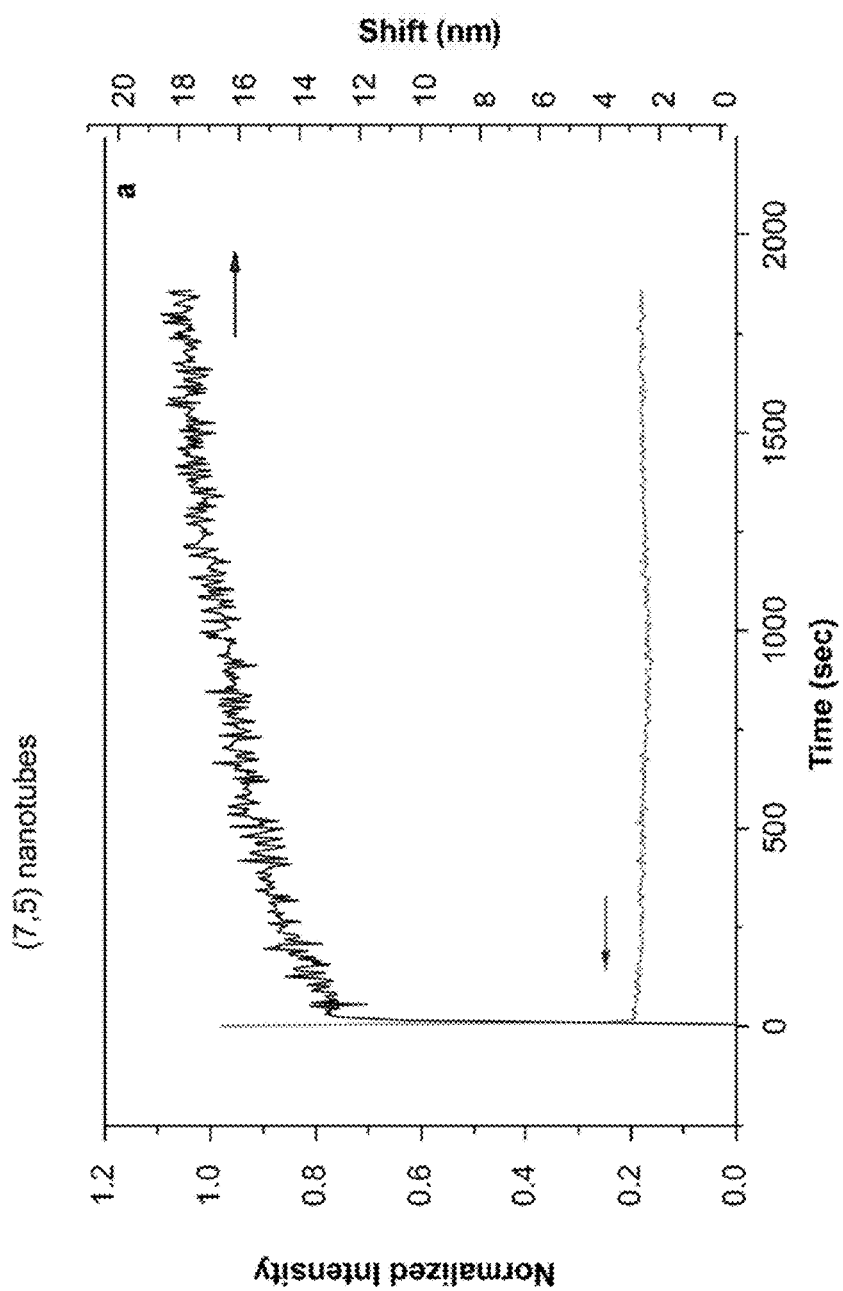
FIG. 17 demonstrates diameter dependence of transient response of BA-PhO-Dex-SWNT to riboflavin.
Figure 17B:
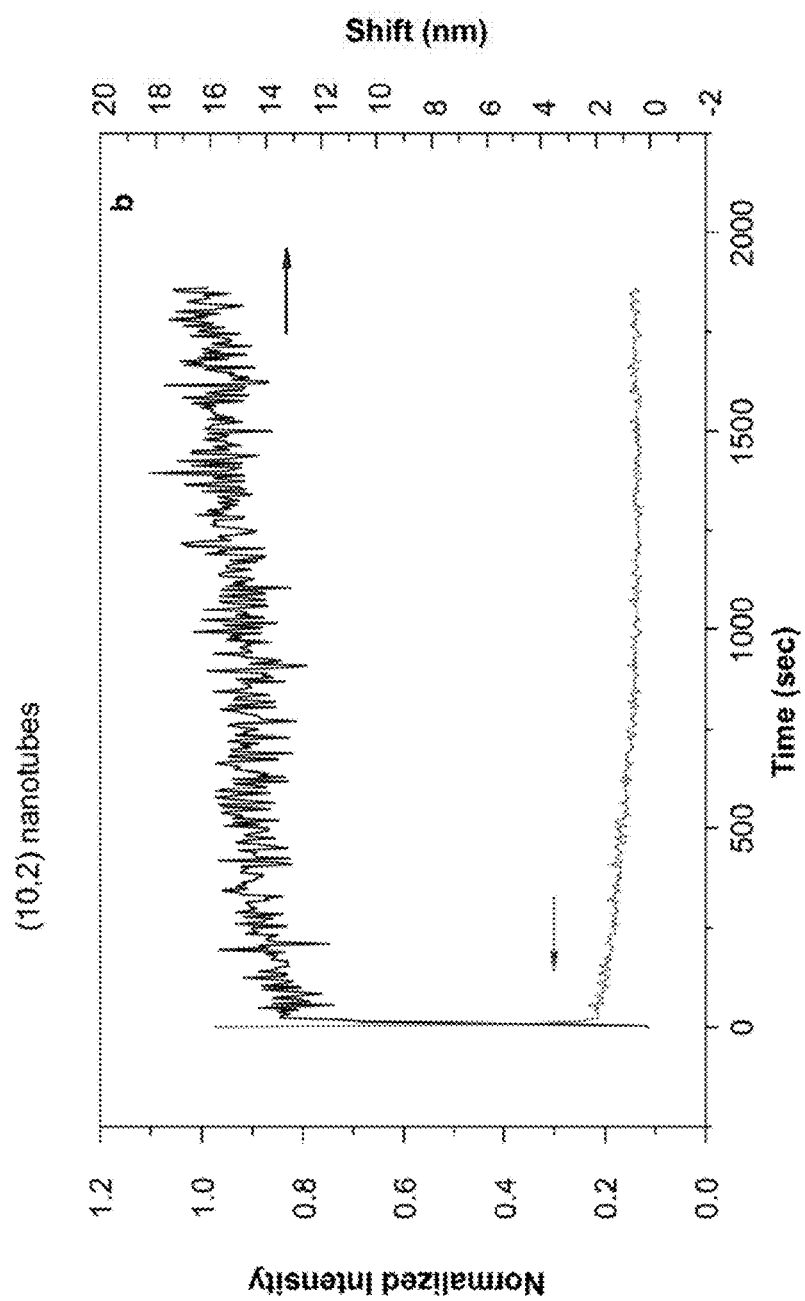
Figure 17C:
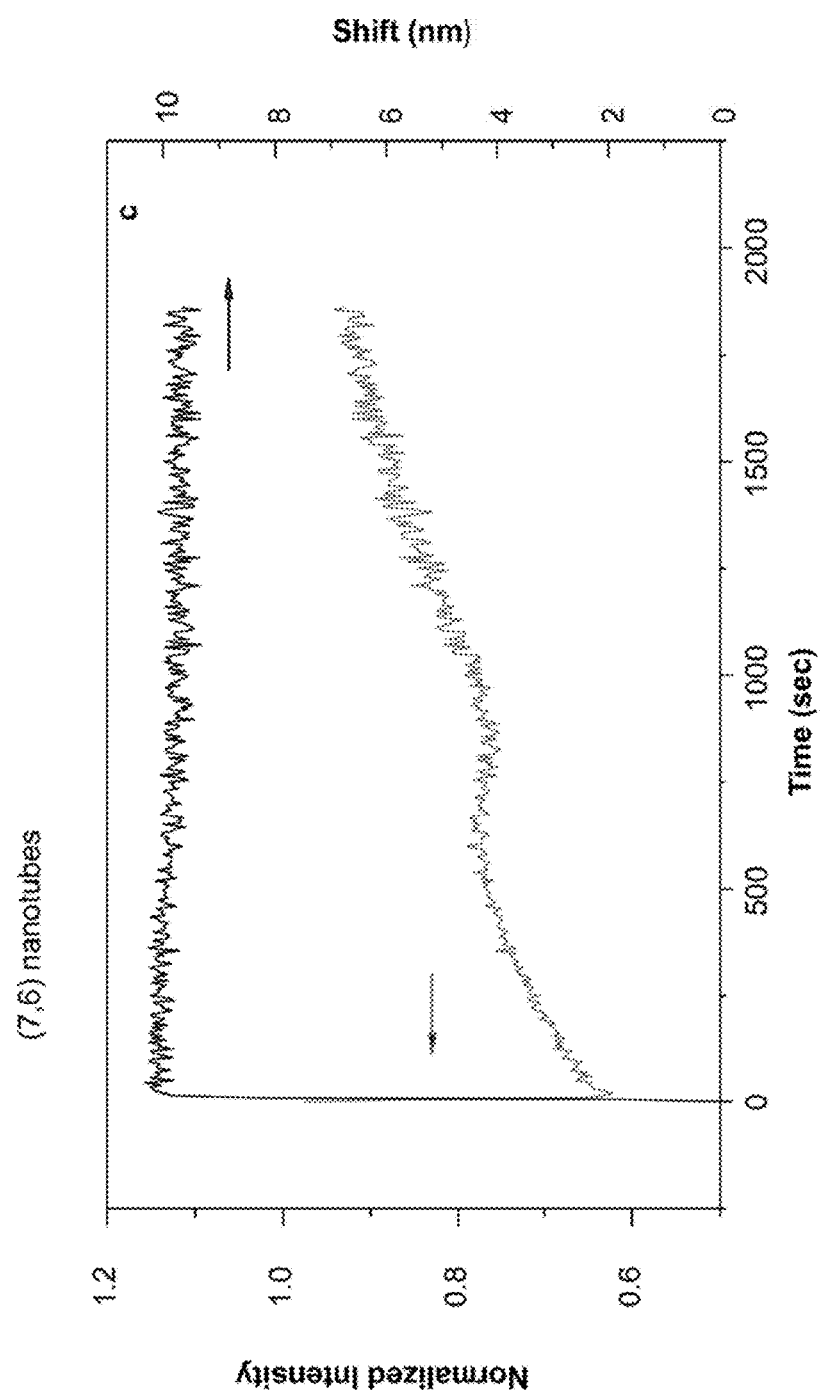
Figure 17D:
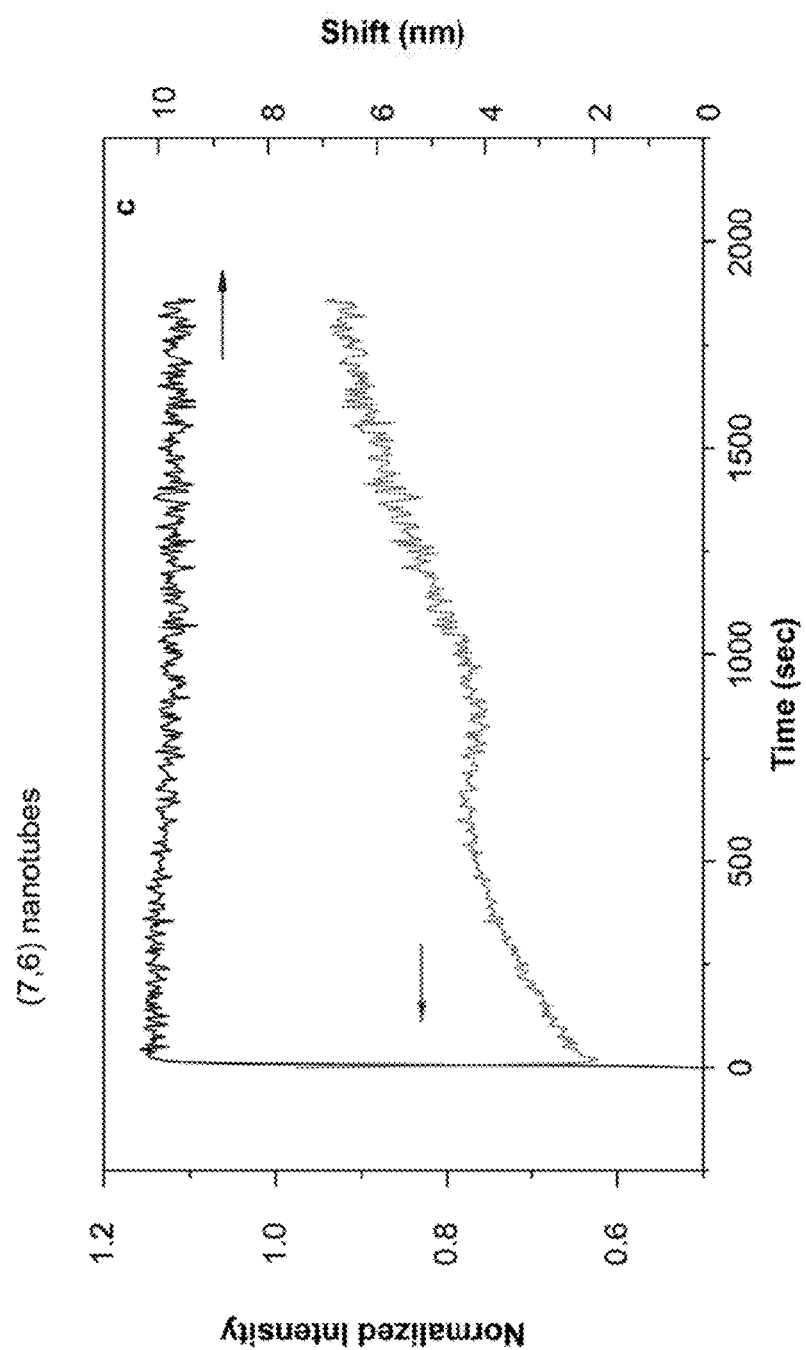

Tunable Affinity:

Biological recognition elements can demonstrate tunable affinity with compositional changes. (Scrutton, N. S., et al., Redesign of the Coenzyme Specificity of a Dehydrogenase by Protein Engineering. Nature 343, 38-43 (1990); Lindberg, R. L. P., et al., Alteration of Mouse Cytochrome P450coh Substrate Specificity by Mutation of a Single Amino-acid Residue. Nature 339, 632-634 (1989), which are incorporated by reference in their entirety). The selective photoluminescence response of BA-PhO-Dex-SWNTs to riboflavin was used to observe tunable affinity (FIG. 8a). In this case, the (7, 5) nanotube red-shifted and decreased in intensity with increasing riboflavin concentration (FIG. 8b-c) in a reversible manner (FIG. 16). The shifting and intensity changes were used to calculate a detection limit (125 and 540 nM, respectively). Likewise, affinity equilibrium constants $K_{a,quench}$ and $K_{a,shift}$ were calculated as 1.66 and 0.00748 $\mu M^{-1}$, respectively. The affinity equilibrium constants suggested that differing mechanisms may account for the intensity and wavelength modulations.

The affinity of recognition was tuned by modifying the polymer composition, in a manner analogous to site directed-mutagenesis. (Scrutton, N. S., et al., (1990); Lindberg, R. L. P., et al., (1989)). Both $K_{a,quench}$ and $K_{a,shift}$ increased with decreasing phenoxy:dextran ratio or increasing boronic acid:dextran ratio (FIG. 8d-e) for BA-PhO-Dex-SWNT recognition of riboflavin. However, dextran alone did not suspend SWNTs. One possible explanation is that the phenoxy groups created attachment sites to the SWNT backbone via 7E-stacking. (Zheng, M. et al., (2003); Zorbas, V. et al. Preparation and characterization of individual peptide-wrapped single-walled carbon nanotubes. J. Am. Chem. Soc 126, 7222-7227 (2004), which is incorporated by reference in its entirety). The number of attachments may have affected the polymer configuration and therefore $K_a$. Modifying the content of phenoxy and boronic acid on the dextran polymer and selecting the (7, 6) nanotube may have resulted in a 170- and 1600-fold of $K_{a,quench}$ and $K_{a,shift}$, respectively (Table 2), with maximum values of 9.9 $\mu M^{-1}$ 0.97 $\mu M^{-1}$. This value of $K_a$ was similar to or greater than those commonly observed for analyte binding proteins, such as riboflavin carrier protein, $K_a$=7.0 $\mu M^{-1}$, glucose binding protein, $K_a$=2.5 $\mu M^{-1}$, and certain DNA aptamers, $K_a$=5-40 $\mu M^{-1}$. (Mason, C. W., et al., Recognition, Cointernalization, and Recycling of an Avian Riboflavin Carrier Protein in Human Placental Trophoblasts. Journal of Pharmacology and Experimental Therapeutics 317, 465 (2006); Ge, X., et al., Dual-labeled glucose binding protein for ratiometric measurements of glucose. Anal. Chem. 76, 1403-1410 (2004); Bock, L. C., et al., Selection of single-stranded DNA molecules that bind and inhibit human thrombin. Nature 355, 564-566 (1992), which are incorporated by reference in their entirety). The strength of the binding affinity exhibited by these nanotube-antibodies was comparable to natural biocatalysts and bio-recognition sites. In FIG. 8f, an optimum in $K_{a,quench}$ was observed at 62.6 wt % BA for the (11, 3) SWNT. This suggests the polymer composition may control analyte recognition to a greater extent than SWNT band-gap, for example.

TABLE 2

Tabulation of $K_{a, quench}$ and $K_{a, shift}$ values. BA-PhO-Dex-SWNT with phenoxy:dextran ratio of 5.75 and boronic acid:dextran ratio of 53.3 was reported in FIG. 8d-e.

| Phenoxy/Dextran (mol/mol) | Boronic Acid/Dextran (mol/mol) | $K_{a, quench}$ ($\mu M^{-1}$) | | | | |
|---|---|---|---|---|---|---|
| SWNT Species | | (7.5) | (10.2) | (9.4) | (7.6) | (8.6) |
| 5.75 | 0 | 0.057 | 0.074 | 0.043 | 0.060 | 0.101 |
| 5.75 | 24.18 | 0.555 | 0.681 | 0.394 | 1.083 | 0.713 |
| 9.93 | 47.49 | 0.474 | 0.884 | 0.446 | 0.614 | 1.251 |
| 8.75 | 49.66 | 0.477 | 0.919 | 0.653 | 0.655 | 1.554 |

TABLE 2-continued

Tabulation of $K_{a,\ quench}$ and $K_{a,\ shift}$ values. BA-PhO-Dex-SWNT with phenoxy:dextran ratio of 5.75 and boronic acid:dextran ratio of 53.3 was reported in FIG. 8d-e.

| 5.75 | 53.3 | 1.660 | 2.510 | 2.078 | 3.655 | 4.992 |
|---|---|---|---|---|---|---|
| 0 | 80.91 | 4.130 | 7.160 | 5.040 | 9.902 | 8.780 |

| Phenoxy/Dextran (mol/mol) | Boronic Acid/Dextran (mol/mol) | $K_{a,\ shift}$ ($\mu M^{-1}$) | | | | |
|---|---|---|---|---|---|---|
| SWNT Species | | (7.5) | (10.2) | (9.4) | (7.6) | (8.6) |
| 5.75 | 0 | — | — | — | — | — |
| 5.75 | 24.18 | 2.6717E-06 | 0.0018 | 0.0072 | 0.1522 | 0.1564 |
| 9.93 | 47.49 | 0.0019 | 0.0049 | 0.0430 | 0.0371 | 0.0105 |
| 8.75 | 49.66 | 0.0006 | 0.0028 | 0.0280 | 0.0243 | 0.0072 |
| 5.75 | 53.3 | 0.0075 | 0.0096 | 0.2455 | 0.5033 | 0.1310 |
| 0 | 80.91 | 0.0059 | 0.0122 | 0.0663 | 0.9684 | 0.0497 |

Molecular Recognition of Riboflavin:

A platform for riboflavin was constructed. Riboflavin (RF) is an essential vitamin for eukaryotic organisms necessary for cell survival and its transport can be facilitated by riboflavin carrier protein (RCP). (Mason, C. W., et al., (2006)). Elevated RCP levels may predict late stage (stage III or IV) breast cancer with a high accuracy. (Rao, P. N., et al., Elevation of serum riboflavin carrier protein in breast cancer. *Cancer Epidemiology Biomarkers & Prevention* 8, 985 (1999), which is incorporated by reference in its entirety).

Figure 11:
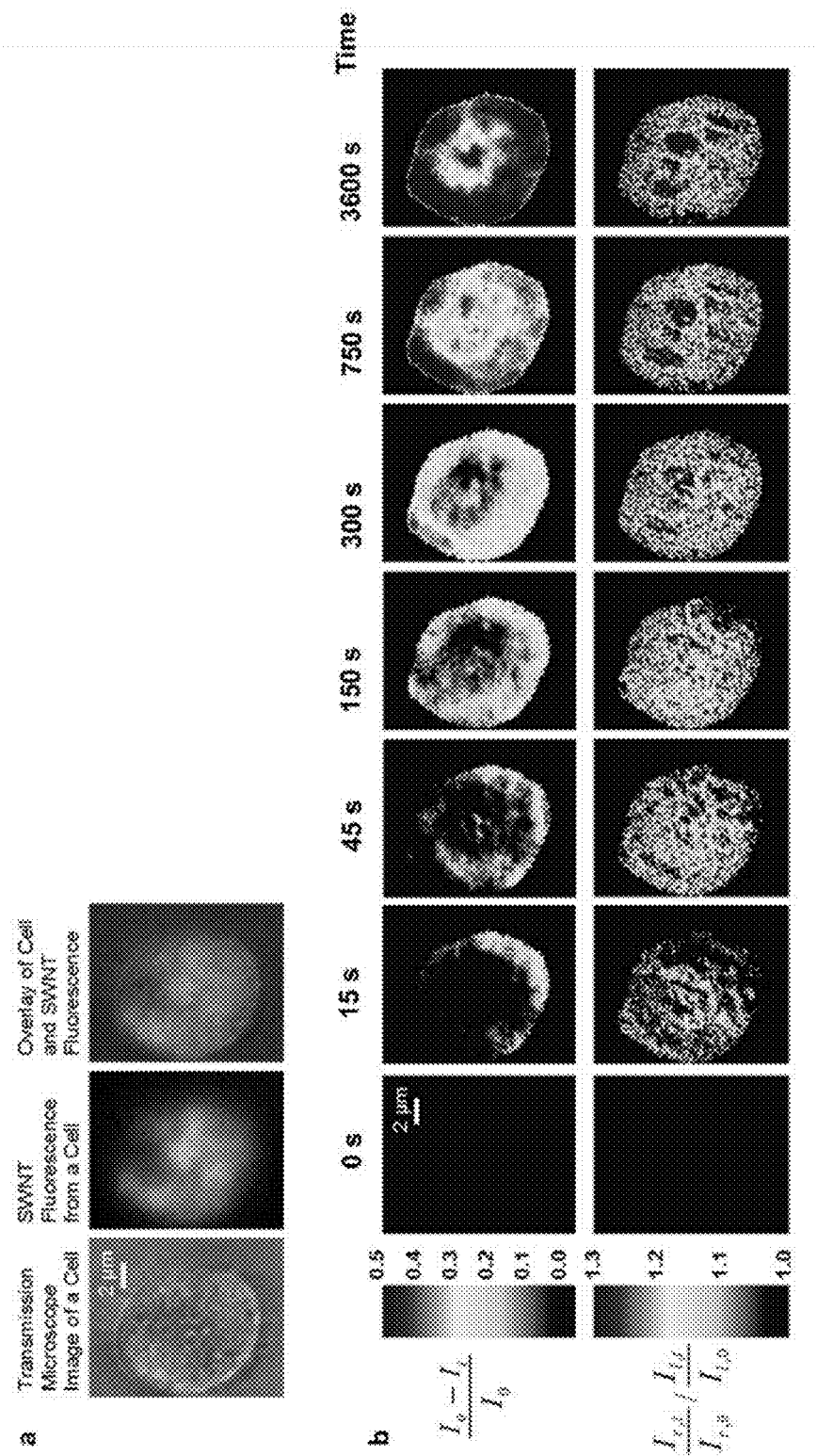
FIG. 11 illustrates application of the composition sensors for RF detection.

BA-PhO-Dex-SWNT was incubated with Raw 264.7 macrophage cells in a riboflavin free medium overnight (FIG. 11a). (Kim, J., et al., (2009)). A home-built nIR, dual-channel imaging microscope was used to spatially image the wavelength shifts of the (7,6) SWNT, $\lambda_{max}=1147$ nm, upon riboflavin binding (FIG. 9).

Following addition of riboflavin to extracellular media, the photoluminescence of SWNTs inside the cell red-shifted systematically over time (FIG. 11b) in response to the diffusion of riboflavin into the cell. Using these results, it was possible to detect riboflavin concentration gradients inside the cell dynamically and with high resolution.

Figure 8B:
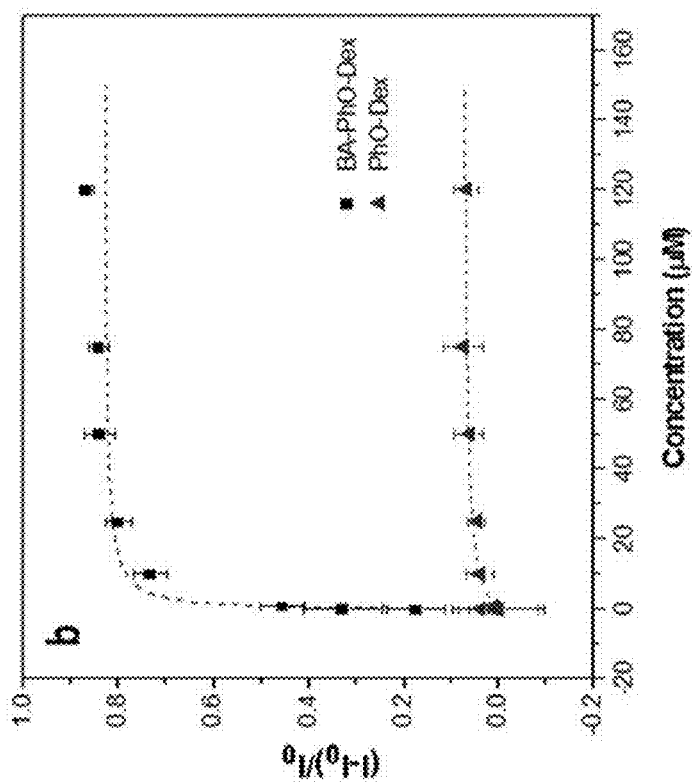
Figure 8C:
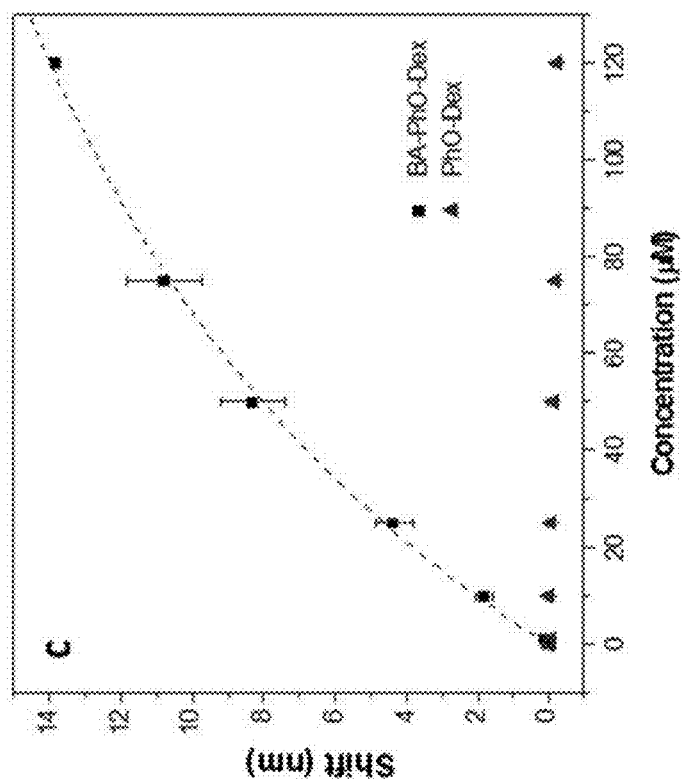
Figure 8D:
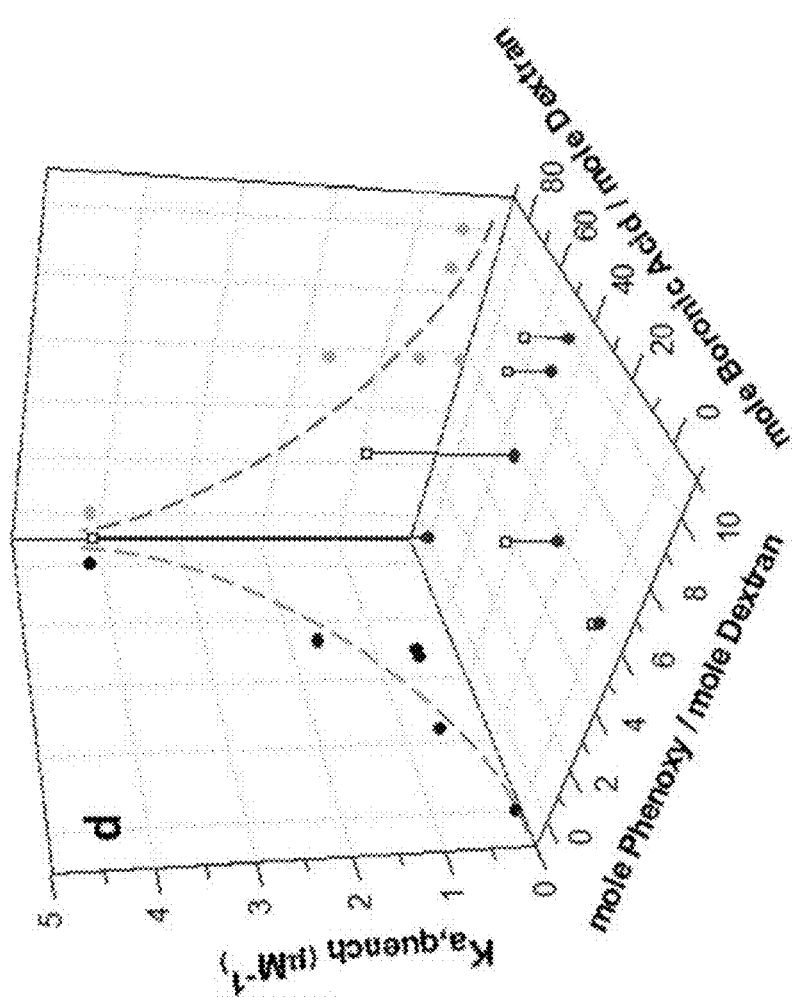
Figure 8E:
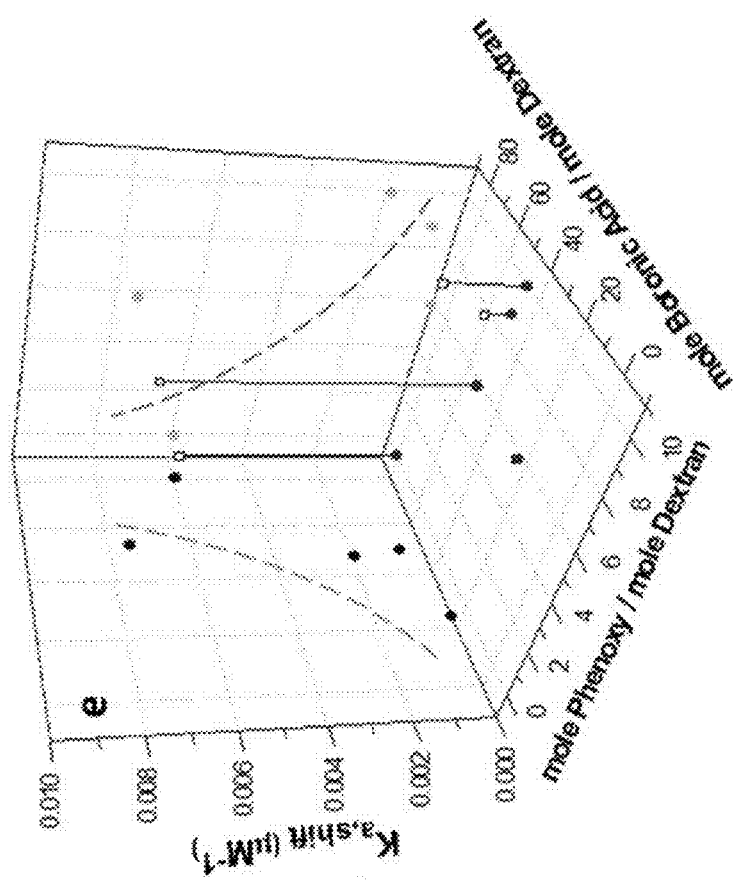
Figure 8F:
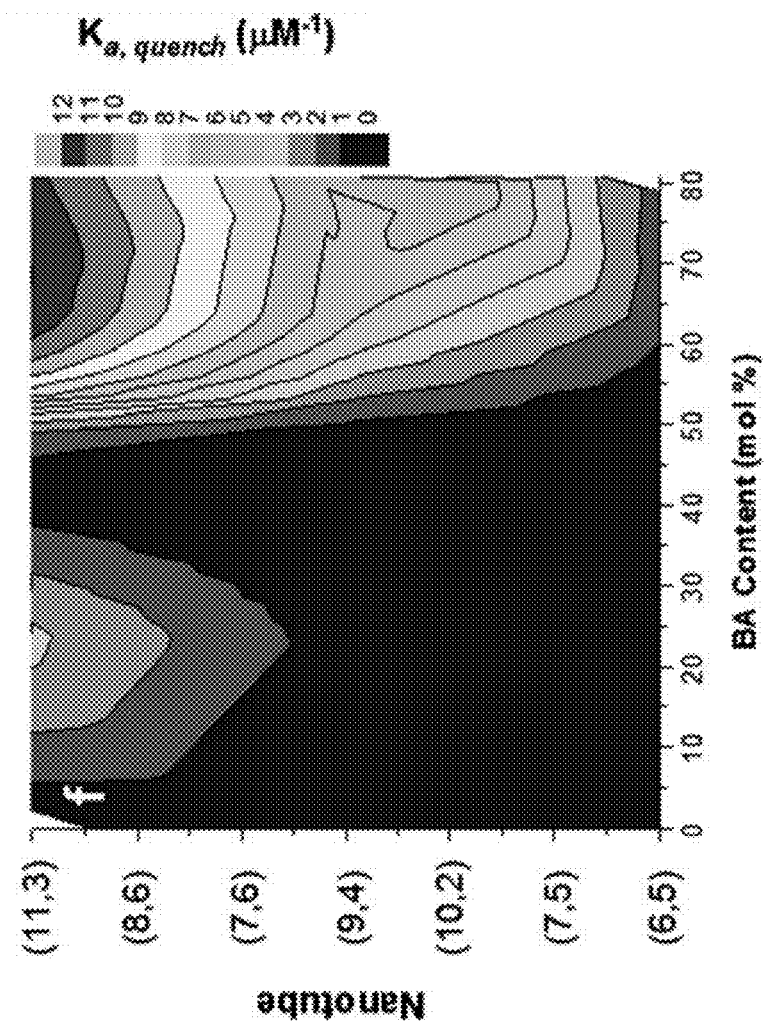
Figure 8G:
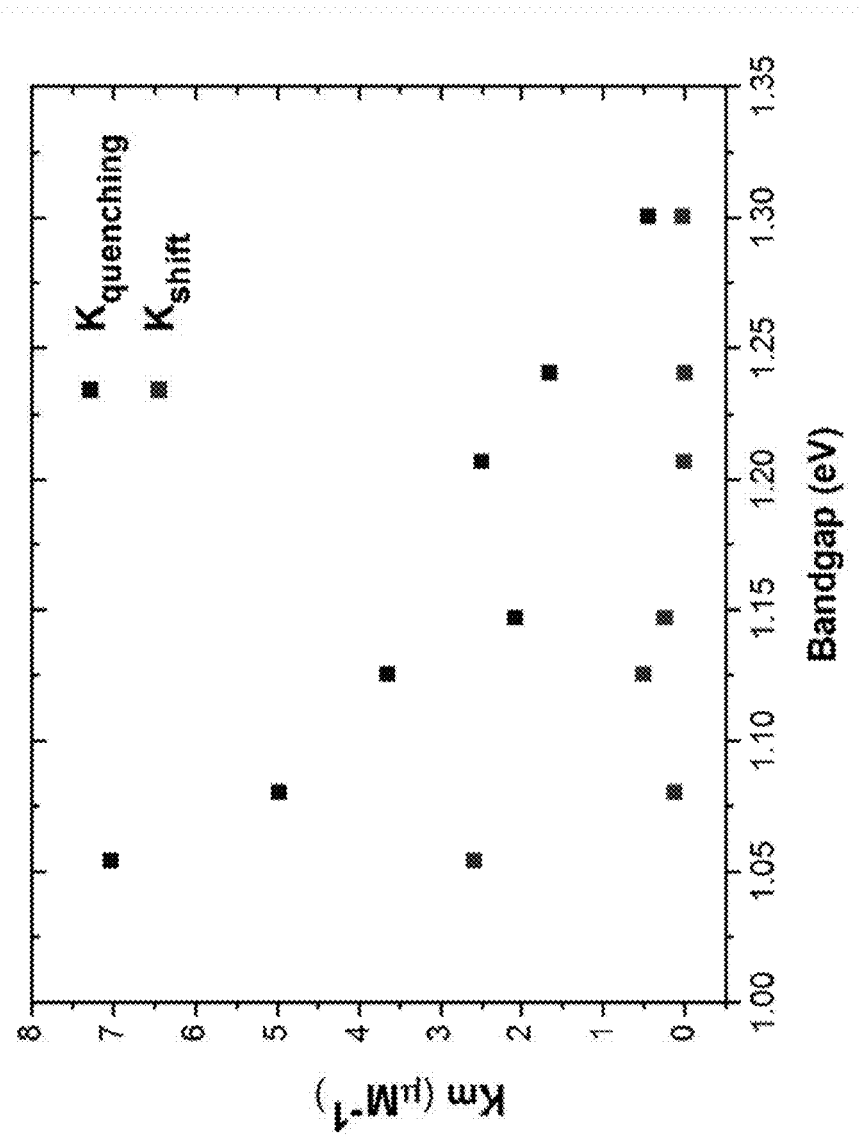

Additionally, for small diameter nanotubes, such as the (7,5) nanotube, the photoluminescence of BA-PhO-Dex SWNT red-shifted and decreased as RF concentration increases (FIG. 8b-c). The response function indicated that the quenching response might be more sensitive at a smaller concentration, whereas the shifting response did not seem to saturate even at the highest concentration range examined. For larger diameter species in the sample, such as the (7,6) and (8,6) nanotubes, the photoluminescence shifting response appeared to be similar to that of the small diameter species, although with a significantly larger $K_{a,shifting}$. At RF concentrations less than 25 μM, the photoluminescence intensity of the large diameter nanotubes also decreased as the RF concentration increased; however, at higher RF concentrations (>25 μM) the quenched intensity recovered with increasing amounts of RF (FIG. 8a). Transient data (FIG. 17) showed similar photoluminescence responses, where the emission intensity for small diameter species only decreased upon exposure to 120 μM RF and large diameter species showed an initial decrease followed by a later restoration of the photoluminescence. Both the steady-state and transient data suggest that the quenching and shifting modes might rely on different, but related mechanisms.

One possible explanation of these results is that the observed quenching of SWNT photoluminescence might be due to RF adsorption to unoccupied SWNT surface sites and the SWNT photoluminescence shift could be from the competitive replacement of adsorbed phenoxy groups with RF. It has been suggested that BA-PhO-Dex polymer wraps SWNT with phenoxy groups adsorbed on the surface of the SWNT through π-stacking. (Zorbas, V., et al., (2004); Zheng, M., et al., (2003)). The RF might be recognized by BA-PhO-Dex-SWNT, and might either adsorb directly onto empty sites of the SWNT surface or compete with phenoxy-occupied sites for binding. The data above suggests that both phenoxy and RF occupied sites yield similar emission intensity, with the intensity lower than that of an empty site. The replacement of adsorbed phenoxy groups with RF might cause a change in the local dielectric environment and might result in an emission maximum shift. (Perebeinos, V., et al., (2004); Walsh, A. G., et al., (2007)). As a result, photoluminescence quenching of BA-PhO-Dex-SWNT could be viewed solely as an outcome from RF adsorption onto an empty site and the competitive adsorption of RF onto phenoxy-occupied sites could be responsible for photoluminescence shift.

A competitive binding model can be formulated with phenoxy being an inhibitor of RF binding to the SWNT surface. With this, the RF binding constant, $K_{RF}$, can be directly equated to the $K_{a,quenching}$. The binding constant of the inhibitor (phenoxy), or $K_{Phe}$, can be inferred from typical competitive binding equilibrium equations with $K_{a,shifting}$ equating $K_{RF}/(1+K_{phe}[\text{Phenoxyl}])$ in the Type I Langmuir formula. Different nanotube species have a different affinity to either RF or phenoxy. For instance, for (7,5) SWNT species $K_{RF}$ is calculated to be 1.66 $\mu M^{-1}$ and $K_{phe}$ 1.25 $\mu M^{-1}$. In other words, 50% of the maximum observed quenching occurs when approximately 350 molecules of RF are adsorbed per SWNT and approximately 470 pre-adsorbed phenoxy molecules would decrease the shift equilibrium constant by half.

Figure 10:
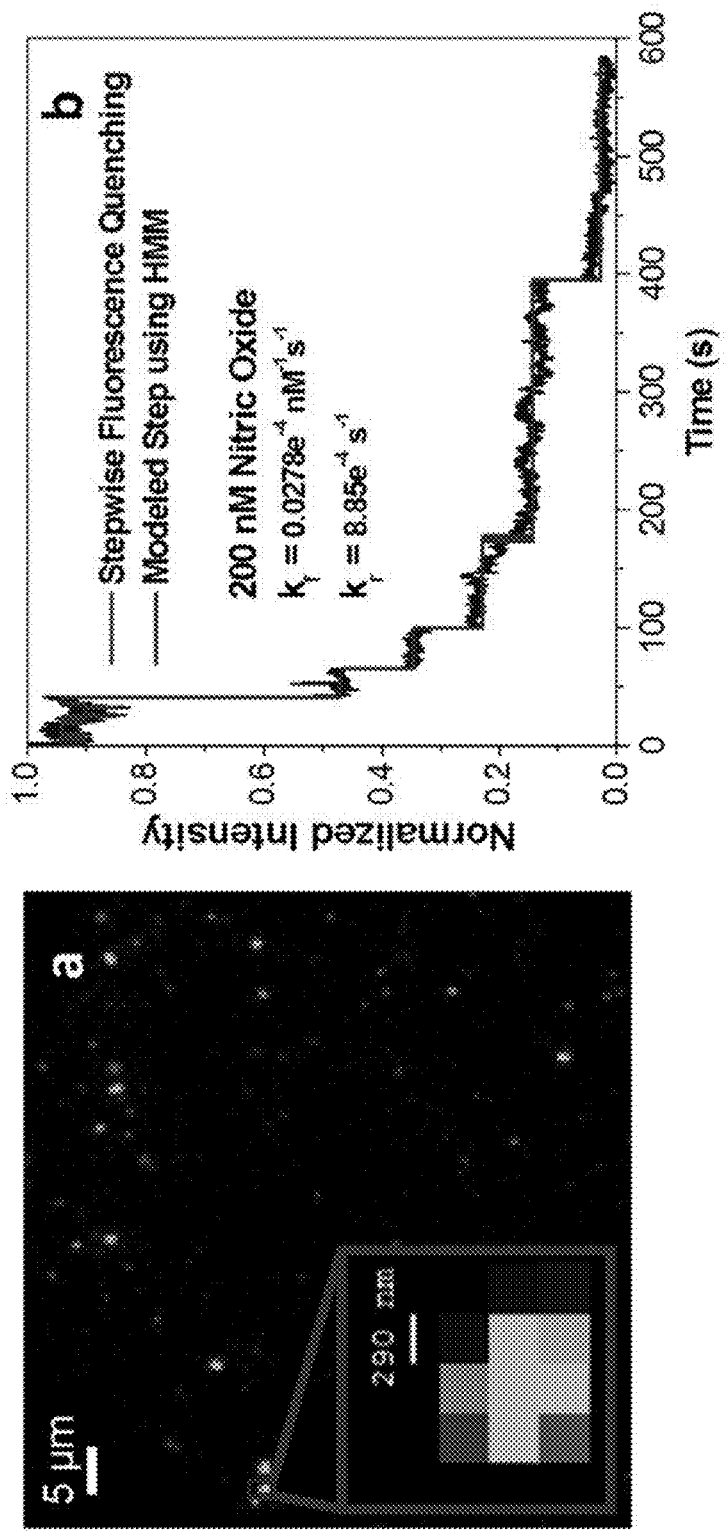
FIG. 10 illustrates application of the composition sensors for NO detection.

Molecular Recognition of NO:

In another example, NO, an important biological signaling molecule, was imaged using $AT_{15}$-SWNTs, with the above defined selectivity, at the single molecule level. (Davis, K. L., et al., Novel effects of nitric oxide. *Annu. Rev. Pharmacol. Toxicol.* 41, 203-236 (2001), which in incorporated by reference in its entirety). Individual nanotubes were immobilized on an aminopropyltriethoxysilane modified cell culture dish via a charged interaction (FIG. 18), resulting in stable photoluminescence intensity (FIG. 10a). Upon exposure to NO, stepwise quenching and de-quenching were observed. This is consistent with single NO molecules adsorbing and desorbing in real time (FIG. 10b and FIG. 19), at concentrations below 200 nM NO. The AT$_{15}$-SWNT construct demonstrated the ability to detect low concentrations of NO selectively and at cellular interfaces.

Figure 58:
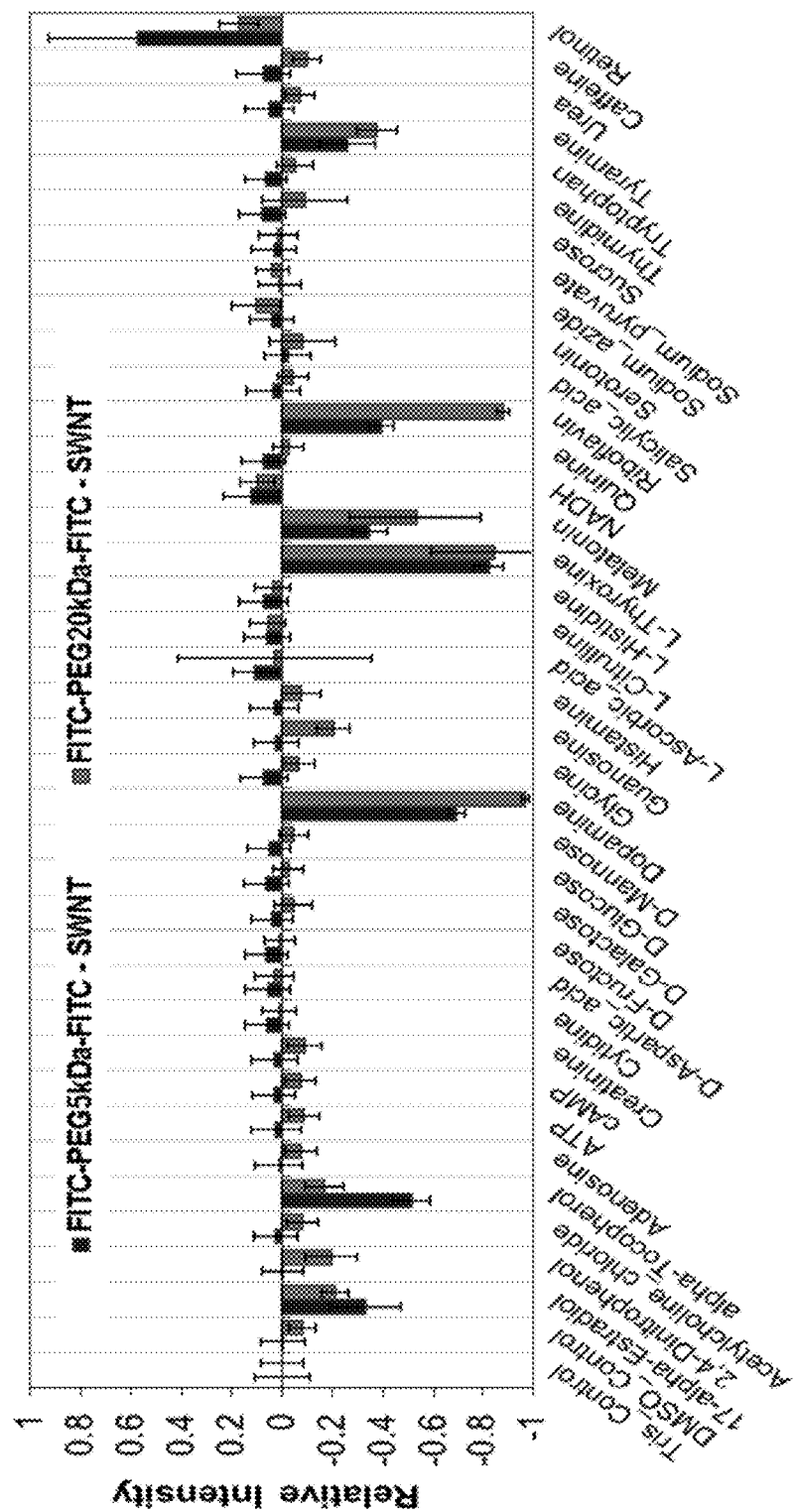
FIG. 58 is a plot of the nanotube specific fluorescence response of SWNT complexes to different analytes.

Dye Conjugates:

In another example, polymers were designed that would allow for distinct fluorescence responses for different molecules, while enabling us to understand those polymer-SWNT complexes with using either molecular dynamics simulation or mean-field based model. Two equivalents of fluorescein isothiocyanate or Rhodamine B isothiocyanate were added to the end of polyethylene glycol polymer with various molecular weights (FITC-PEG-FITC, Equation 1 and RITC-PEG-RITC, Equation 2), ranging from 1 kDa to 20 kDa. UV-vis absorption and FTIR spectroscopy verified the success of the chemistry. These polymers were designed such that the fluorophores on the polymers can assist identifying structural information of the polymer-SWNT complexes. Hydrophilic regions of the polymer were expected to be extended into water, while hydrophobic regions will be interacting with SWNT surface; therefore, the length of the hydrophilic region was tuned by the molecular weights of the PEG. This simple but well-designed polymer structure will allow us to study the basics of the interactions between the SWNT and the polymer. Preliminary high-throughput screening results indicate FITC-PEG-FITC-SWNT constructs with different molecular weights impart SWNT with similar selectivity but different degrees of quenching responses towards the panel of the molecules. See FIG. 58, which shows the relative intensity change in emission maximum of a (7, 5) nanotube in FITC-PEG5kDa-FITC-SWNTs (dark bars) and FITC-PEG20 kDa-FITC-SWNTs (light bars), after exposure to 36 analytes.

Equation 1

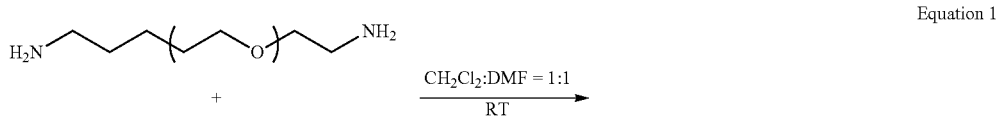

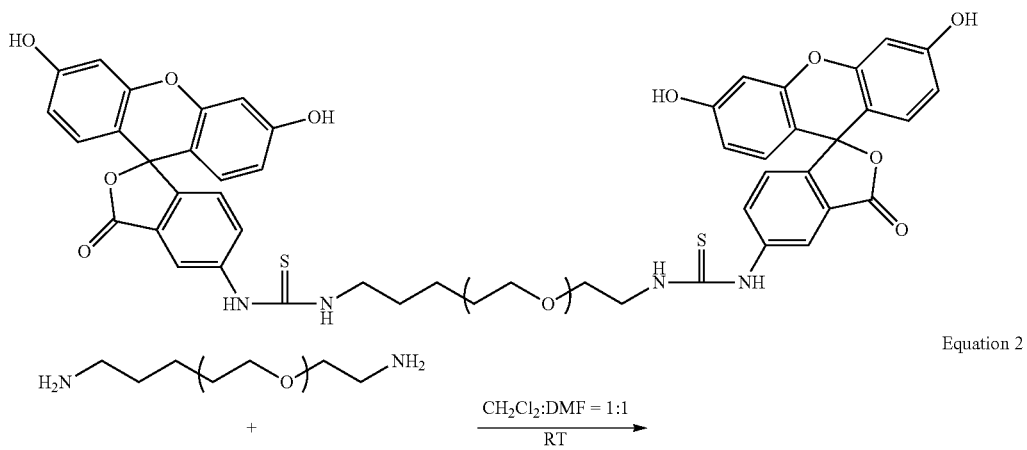

Equation 2

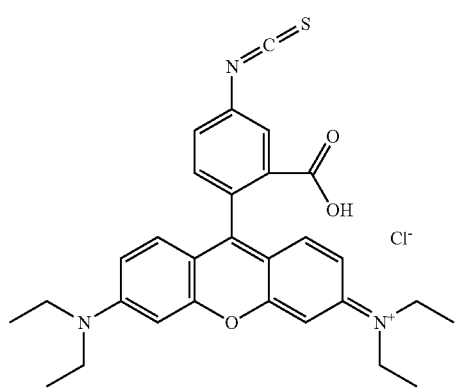

-continued

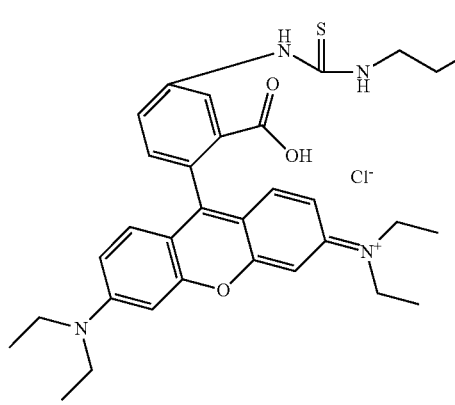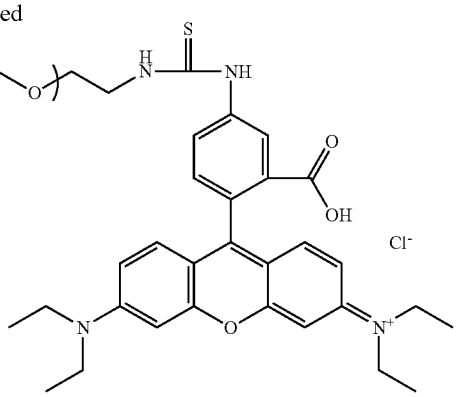

Figure 59:
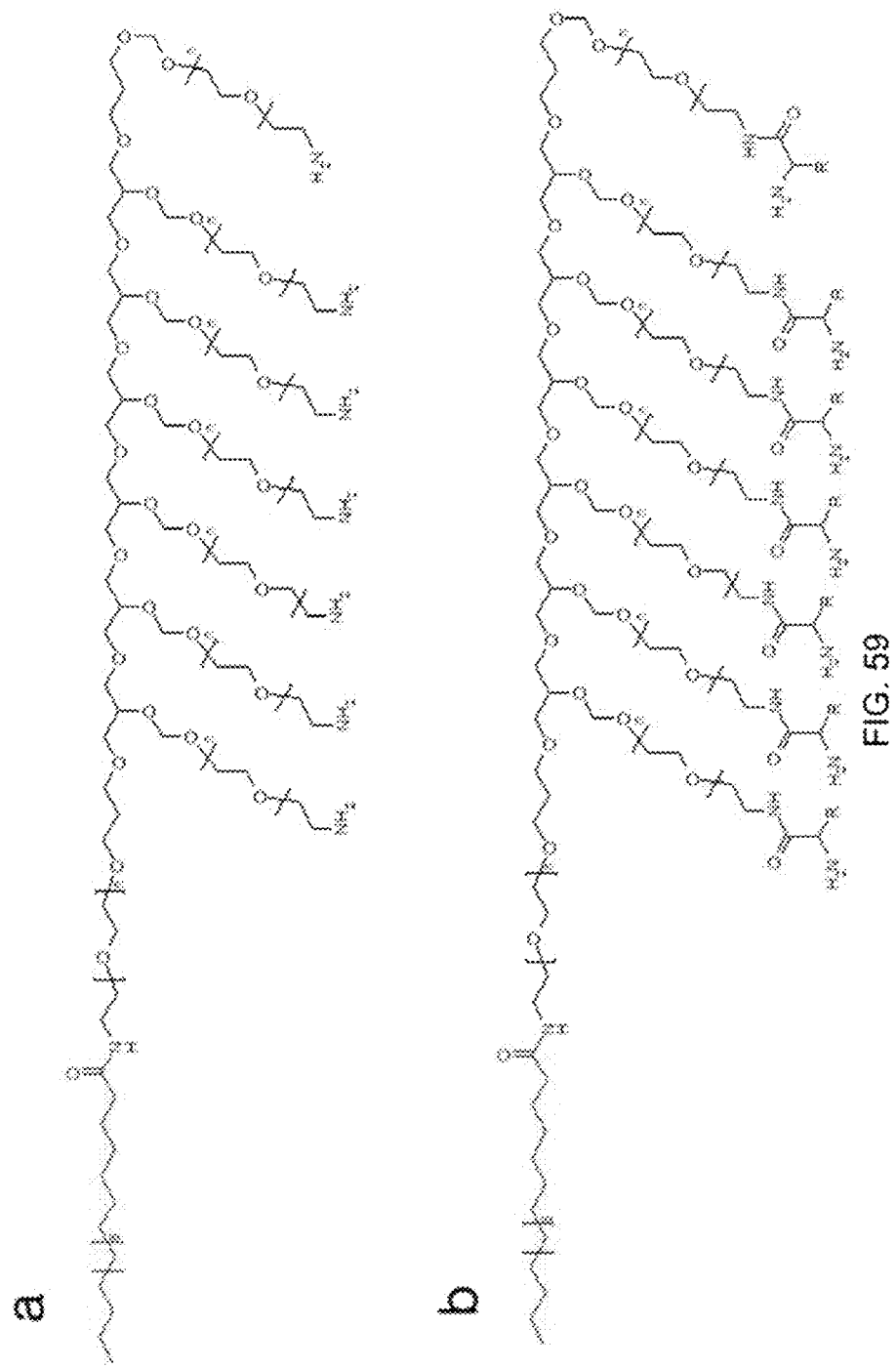
FIG. 59 is a diagram of copolymer structures.

Branched Polymers:

In another example, a systematically designed system was developed using branched polymer. Branched PEG polymers having 2, 4 and 8 arms were modified with a hydrophobic palmitoyl group, and the resulting synthetic polymers (PPEG2-NH$_2$, PPEG4-NH$_2$, PPEG8-NH$_2$) were characterized by NMR, FT-IR and UV. Examples of the compounds are shown in FIG. 59. Those PPEG derivatives were able to suspend single-walled carbon nanotubes in aqueous solution, showing intense and stable nIR fluorescence. Then, PPEG/SWNT sensors were screened for 33 different kinds of proteins, and their fluorescence responses were analyzed using the high throughput analyzing program. It was found that each PPEG/SWNT sensor showed a different response to proteins. The PPEG2-NH$_2$/SWNT sensor showed a more specific response to insulin and MSP1 while the PPEG8-NH$_2$/SWNT showed quenching response to many proteins, indicating specific molecular recognition. A polymer library from the PPEG mother polymer was generated, such as Fmoc-Phe-coupled PPEG8 (PPEG8-Phe-Fmoc), PPEG4 (PPEG4-Phe-Fmoc) and PPEG2 (PPEG2-Phe-Fmoc). PPEG8-Phe-Fmoc was also able to suspend SWNT in aqueous solution, and the sensor was screened for proteins. The PPEG8-Phe-Fmoc/SWNT sensor did not respond to any protein, which is very different from the PPEG8-NH$_2$/SWNT sensor. The PEGs included 5kDa and 20 kDa polymers.

A number of embodiments of the invention have been described. Nevertheless, it will be understood that various modifications may be made without departing from the spirit and scope of the invention. It should also be understood that the appended drawings are not necessarily to scale, presenting a somewhat simplified representation of various preferred features illustrative of the basic principles of the invention.

What is claimed is:

1. A composition, comprising:
   a complex, wherein the complex includes:
   a nanostructure, wherein the nanostructure is a photoluminescent nanostructure,
      wherein the photoluminescent nanostructure is a single-walled carbon nanotube; and
   a polymer, the polymer adsorbed on the nanostructure and the polymer being free from selective binding to an analyte in the absence of being adsorbed on the nanostructure,
      wherein the polymer is a boronic acid functionalized phenoxy dextran; and
   a selective binding site for the analyte on the complex.

2. The composition of claim 1, wherein the analyte is a monosaccharide, a polysaccharide, an amino acid, a nucleotide, an oligonucleotide, a lipid, a polylipid, a steroid, a peptide, a protein, riboflavin, or nitric oxide.

3. The composition of claim 1, wherein the analyte is 17-α-estradiol, 2,4-dinitrophenol, acetylcholine chloride, α-tocopherol, adenosine, adenosine-5'-triphosphate, cyclic adenosine monophosphate, creatinine, cytidine, D-aspartic acid, D-fructose, D-galactose, D-glucose, D-mannose, dopamine, glycine, guanosine, histamine, L-ascorbic acid, L-citrulline, L-histidine, L-thyroxine, melatonin, NADH, quinine, salicylic acid, serotonin, sodium azide, sodium pyruvate, sucrose, thymidine, tryptophan, tyramin or urea.

4. The composition of claim 1, further comprising an amount of the analyte.

5. The composition of claim 4, wherein the analyte is a therapeutic.

6. A system comprising:
   the composition of claim 1;
   an electromagnetic radiation source having an excitation wavelength directed at the composition; and
   a detector configured to receive an emission wavelength from the composition.

* * * * *